(12) United States Patent
Schmidt et al.

(10) Patent No.: US 10,293,330 B2
(45) Date of Patent: May 21, 2019

(54) CRYSTALLINE GERMANOSILICATE MATERIALS OF NEW CIT-13 TOPOLOGY AND METHODS OF PREPARING THE SAME

(71) Applicant: CALIFORNIA INSTITUTE OF TECHNOLOGY, Pasadena, CA (US)

(72) Inventors: Joel E. Schmidt, Utrecht (NL); Mark E. Davis, Pasadena, CA (US); Ben W. Boal, Pasadena, CA (US); Jong Hun Kang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/169,816

(22) Filed: Jun. 1, 2016

(65) Prior Publication Data

US 2016/0346771 A1 Dec. 1, 2016

Related U.S. Application Data

(60) Provisional application No. 62/169,310, filed on Jun. 1, 2015.

(51) Int. Cl.
| | |
|---|---|
| *B01J 29/04* | (2006.01) |
| *C01B 39/00* | (2006.01) |
| *B01J 20/10* | (2006.01) |
| *B01J 20/30* | (2006.01) |
| *C07C 5/41* | (2006.01) |
| *C07C 5/22* | (2006.01) |
| *C07C 2/66* | (2006.01) |
| *C07C 2/10* | (2006.01) |
| *C07C 7/13* | (2006.01) |
| *C10G 47/04* | (2006.01) |
| *C10G 2/00* | (2006.01) |
| *C07D 301/12* | (2006.01) |
| *C10G 29/20* | (2006.01) |
| *C10G 35/06* | (2006.01) |
| *C10G 45/04* | (2006.01) |
| *C10G 45/60* | (2006.01) |
| *C10G 45/68* | (2006.01) |
| *C10G 50/00* | (2006.01) |
| *C10G 3/00* | (2006.01) |
| *C10G 11/02* | (2006.01) |
| *C07C 1/20* | (2006.01) |
| *C07C 6/12* | (2006.01) |
| *B01J 35/00* | (2006.01) |
| *B01D 53/94* | (2006.01) |

(52) U.S. Cl.
CPC ............ *B01J 29/047* (2013.01); *B01J 20/10* (2013.01); *B01J 20/3057* (2013.01); *B01J 35/002* (2013.01); *C01B 39/00* (2013.01); *C07C 1/20* (2013.01); *C07C 2/10* (2013.01); *C07C 2/66* (2013.01); *C07C 5/2213* (2013.01); *C07C 5/412* (2013.01); *C07C 6/12* (2013.01); *C07C 7/13* (2013.01); *C07D 301/12* (2013.01); *C10G 2/33* (2013.01); *C10G 3/44* (2013.01); *C10G 11/02* (2013.01); *C10G 29/205* (2013.01); *C10G 35/06* (2013.01); *C10G 45/04* (2013.01); *C10G 45/60* (2013.01); *C10G 45/68* (2013.01); *C10G 47/04* (2013.01); *C10G 50/00* (2013.01); *B01D 53/9418* (2013.01); *B01D 2255/30* (2013.01); *C07C 2529/04* (2013.01)

(58) Field of Classification Search
CPC ............ C07C 2/10; C07C 2/66; C07C 5/2213
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 3,140,253 A | 7/1964 | Plank et al. |
| 3,904,738 A | 9/1975 | Robson |
| 4,016,245 A | 4/1977 | Plank et al. |
| 4,061,717 A | 12/1977 | Kerr et al. |
| 4,483,835 A | 11/1984 | Zones |
| 4,503,024 A | 3/1985 | Bourgogne et al. |
| 4,544,538 A | 10/1985 | Zones |
| 4,873,067 A | 10/1989 | Valyocsik et al. |
| 4,910,006 A | 3/1990 | Zones et al. |
| 4,925,548 A | 5/1990 | Rubin |
| 5,316,753 A | 5/1994 | Nakagawa |
| 5,614,166 A | 3/1997 | Gies et al. |
| 5,958,370 A | 9/1999 | Zones et al. |
| 6,508,860 B1 | 1/2003 | Kulkarni et al. |

(Continued)

FOREIGN PATENT DOCUMENTS

| | | |
|---|---|---|
| WO | WO 1999/008961 A1 | 2/1999 |
| WO | WO 2005/063624 | 7/2005 |

(Continued)

OTHER PUBLICATIONS

Yannick (Journal of Solid State Chemistry; 182, 2009, 622-629).*
Accardo, et al., "Peptide-based Targeting Strategies for Simultaneous Imaging and Therapy with Nanovectors" Polymer J., May 2013, 45, 481-93.
Agadjanian et al, "Specific Delivery of Corroles to Cells via Noncovalent Conjugates with Viral Proteins", Pharmaceutical Research, Feb. 2006, 23(2), 367-377.
Aina, et al., "Therapeutic Cancer Targeting Peptides", Biopolymers, Oct. 2002, 66(3), 184-99.

(Continued)

*Primary Examiner* — Pancham Bakshi
(74) *Attorney, Agent, or Firm* — BakerHostetler

(57) ABSTRACT

The present disclosure is directed to novel crystalline germanosilicate compositions and methods of producing the same. In particular, the crystalline germanosilicate compositions are extra-large-pore compositions, designated CIT-13 possessing 10- and 14-membered rings. The disclosure describes methods of preparing these compositions using substituted benzyl-imidazolium organic structure-directing agents (OSDAs). Also disclosed are methods of using these crystalline compositions.

25 Claims, 22 Drawing Sheets

(56) References Cited

U.S. PATENT DOCUMENTS

| | | | |
|---|---|---|---|
| 6,605,267 | B1 | 8/2003 | Lee |
| 6,676,732 | B2 | 1/2004 | Lee et al. |
| 6,827,843 | B2 | 12/2004 | Elomari |
| 6,841,063 | B2 | 1/2005 | Elomari |
| 6,960,327 | B2 | 11/2005 | Navrotsky et al. |
| 7,008,610 | B2 | 3/2006 | Cao et al. |
| 7,083,714 | B2 | 8/2006 | Elomari |
| 7,138,099 | B1 | 11/2006 | Zones et al. |
| 7,527,782 | B2 | 5/2009 | Corma et al. |
| 7,713,512 | B2 | 5/2010 | Zones et al. |
| 8,105,481 | B2 | 1/2012 | Driver et al. |
| 8,444,952 | B2 | 5/2013 | Dodin et al. |
| 9,278,344 | B2 | 3/2016 | Jothimurugesan et al. |
| 2003/0206844 | A1 | 11/2003 | Lee et al. |
| 2005/0154244 | A1 | 7/2005 | Cao et al. |
| 2005/0197519 | A1 | 9/2005 | Cao et al. |
| 2006/0110321 | A1 | 5/2006 | Corma et al. |
| 2009/0005600 | A1 | 1/2009 | Bosch et al. |
| 2010/0260665 | A1 | 10/2010 | Archer et al. |
| 2010/0305335 | A1 | 12/2010 | Palmer et al. |
| 2010/0324320 | A1 | 12/2010 | Caullet et al. |
| 2012/0041210 | A1 | 2/2012 | Dodin et al. |

FOREIGN PATENT DOCUMENTS

| | | |
|---|---|---|
| WO | WO 2006/033470 A2 | 3/2006 |
| WO | WO 2008/016423 A1 | 2/2008 |
| WO | WO 2010/118377 A2 | 10/2010 |

OTHER PUBLICATIONS

Allen, "Ligand-Targeted Therapeutics in Anticancer Therapy", Nature Rev. Cancer, Oct. 2, 2002, 2(10), 750-63.

Almadhoun et al, "Nanocomposites of Ferroelectric Polymers With Surface-Hydroxylated BaTiO3 Nanoparticles for Energy Storage Applications", Chem., May 2012, 22, 11196.

Arkles, "Silane Coupling Agents Connecting Across Boundaries", 2006, Version 2.0, 60 pages.

Autret et al, "Synthesis and Electrochemistry of Iron (111) Corroles Containing a Nitrosyl Axial Ligand. Spectral Characterization of [(OEC)FeTll(NO)]nW here n=0, 1, 2, or −1 and OEC is the Trianion of 2,3,7,8,12,13,17,18-Octaethylcorrol", J. Am. Chem. Soc., 1994, vol. 116, 9141-9149.

Aviv et al, "Corrole-Based Applications", Chemical Communications, May 28, 2007, 1987-1999.

Baerlocher, et al., "Charge Flipping Combined with Histogram Matching to Solve Complex Crystal Structures from Powder Diffraction Data", 2007, vol. 222, 47-53.

Barata et al., "Corrole-Silica Hybrid Particles: Synthesis and Effects on Singlet Oxygen Generation", RSC Adv., Oct. 24, 2012, vol. 3, 274-80.

Barbe et al, "Metallocorroles As Sensing Components for Gas Sensors: Remarkable Affinity and Selectivity of Cobalt(III) Corroles for CO vs. O2 and N2", The Royal Society of Chemistry, Mar. 23, 2004, 1208-1214.

Basabe, et al., "Locattion of Extra-Framework Co2, Ni2, Cu2, and Zn2 Cations in Natural and Dealuminated Clinoptilolite", Micro and Meso Materials, 2012, vol. 155, 233-239.

Bleken, et al., "The Effect of Acid Strength on the Conversion of Methanol to Olefins Over Acidic Microporous Catalysts with the CHA Topology", Top. Catal. Jan. 2009, vol. 52, 218-228.

Blumenfeld et al, "Decorating Metal Oxide Surfaces with Fluorescent Chlorosulfonated Corroles", Inorganic Chemistry, Apr. 2013, vol. 52, 4774-4776.

Boal et al., "Synthesis of Germanosilicate Molecular Sieves from Mono- and Di-Quaternary Ammonium OSDAs Constructed from Benzyl Imidazolium Derivatives: Stabilization of Large Micropore Volumes Including New Molecular Sieve CIT-13", Chemistry of Materials, Mar. 2016, 28, 2158-2164.

Bravo-Suarez, et al., "Design of Heterogeneous Catalysts for Fuels and Chemicals Processing: An Overview", Amen. Chem. Society, 2013, Chapter 1, 1-66.

Burton, et al., "Organic Molecules in Zeolite Synthesis: Their Preparation and Structure-Directing Effects", Zeolite Science and Practice, 2007, vol. 3, 137-179.

Camblor et al., "Synthesis of all-silica and high-silica molecular sieves in fluoride media", Topics in Catalysis, 1999, 9, 59-76.

Cartlidge, et al. "Hydrothermally Stable Chabazites for the Selective Preparation of Olefins from Methanol", In Zeolites: Facts, Figures, Future, Jacobs, Eds. Elsevier: Amsterdam, 1989, 1151-1161.

Corma, "State of the Art and Future Challenges of Zeolites as Catalysts", Journal of Catalysis, 2003, vol. 216, 298-312.

Corma, et al., "Zeolites and Catalysis" Wiley-VCH Verlag GmbH & Co., Czech Republic, 2010, 911 pgs.

Davis, "Ordered porous materials for emerging applications", Nature, 2002, 417, 813-821.

Davis, et al., "Zeolite and Molecular Sieve Synthesis", Chem. Mater., 1992, vol. vol. 4, 756-768.

Degnan, "Applications of Zeolites in Petroleum Refining", Topics in Catalysis, 2000, vol. 13, 349-356.

Dorset, et al., "P-Derived Organic Cations as Structure-Directing Agents: Synthesis of High-Silica Zeolite (ITQ-27) with a Two-Dimensional 12-Ring Channel System", J. Am. Chem. Soc., Jun. 16, 2006, vol. 128, 8862-8867.

Dusselier et al., "Influence of Organic Structure Directing Agent Isomer Distribution on the Synthesis of SSZ-39," Chemistry of Materials, Mar. 30, 2015, vol. 27, 2695-2702.

Framework Type STW. Available from: www.iza-structure.org/databases, retrieved Oct. 16, 2014.

Froment, et al., In Catalysis in the Conversion of Methanol into Olefin, Spivey, J. J., Ed. The Royal Society of Chemistry, 1992, vol. 9(1), 64 pgs.

Grosse-Kunstleve, et al., "Powder Diffraction Data and Crystal Chemical Information Combined in an Automated Structure Determination Procedure for Zeolites", J. Appl. Crystallogr., 1997, vol. 30, 985-995.

Haber et al, "Protecting the Beneficial Functionality of Lipoproteins by 1-fe, A Corrole-Based Catalytic Antioxidant", Chem. Sci., 2011, vol. 2, 295-302.

Hathaway et al., "High resolution, quasi-equilibrium sorption studies of molecular sieves", Catalysis Letters, 1990, 5, 333-347.

Hong, et al., "Synthesis Structure Solution, Characterization, and Catalytic Properties of TNU-10: A High-Silica Zeolite with the STI Topology", J. Am. Chem. Soc., 2004, vol. 126, 5817-26.

Hori, T. and Osuka, A., "Nucleophilic Substitution Reactions of meso-5,10,15-Tris(pentafluorophenyl)-Corrole; Synthesis of ABC-Type Corroles and Corrole-Based Organogels", Eur. J. Org. Chem., 2010, 2379-2386.

Hua et al., "A Germanosilicate Structure with 11×11×12-Ring Channels Solved by Electron Crystallography", Angewandte Chemie International Edition, Jun. 2014, 53, 5868-5871.

Hwang et al, "Photoexcitation of Tumor-Targeted Corroles Induces Singlet Oxygen-Mediated Augmentation of Cytotoxicity", Journal of Controlled Release, 2012, vol. 163, 368-373.

Ikeda, et al., "Lateral Distribution of N3 Dye Molecules on TiO2 (110) Surface", Journal of Photochemistry, 2009, vol. 202, 185-190.

IZA-Structure-Commission, "Database of Zeolite Structures" http://izasc.biw.kuleuven.be/fmi/xsl/IZA-SC/ft.xsl, Accessed Jan. 7, 2016, 1 pg.

Jackowski, et al., "Diquaternary Ammonium Compounds in Zeolite Synthesis: Cyclic and Polycyclic N-Heterocycles Connected by Methylene Chains", J. Am. Chem. Soc. Jan. 7, 2009, vol. 131, 1092-100.

Jaracz, et al., "Recent Advances in Tumor-Targeting Anticancer Drug Conjugates" Bioorg. Med. Chem., Dec. 2005, vol. 13(17), 5043-54.

Ji, et al., "Organic-Free Synthesis of CHA-Type Zeolite Catalysts for the Methanol-to-Olefins Reaction", ACS Catalysis, 2015, vol. 5, 4456-4465.

(56) References Cited

OTHER PUBLICATIONS

Jin, et al., "Targeted Delivery System of Nanobiomaterials in Anticancer Therapy from Cells to Clinics", BioMed. Res. Inti., Feb. 2014, 24 pages.
Kanamoril et al, "Neuroprotection Against Superoxide Anion Radical by Metallocorroles in Cellular and Murine Models of Optic Neuropathy", Journal of Neurochemistry, 2010, vol. 114, 488-498.
Kim, et al., "A Case Study of Divergent Structure Directing Effects of Geometric Isomers" The Discovery of a New Structure Directing Agent for an All-Silica RTH Zeolite Prepared in Fluoride Media, Microporous and Mesoporous Materials, Apr. 11, 2008, vol. 116, 227-32.
Kubota, et al., "Properties of Organic Cations that Lead to the Structure-Direction of High-Silica Molecular Sieves", Microporous Materials, 1996, vol. 6, 213-229.
Lee, et al., "Polymethylated Octanes Leading to Zeolote SSZ-50", Journ. of Solid State Chem., Mar. 1, 2002, vol. 167, 289-98.
Lee, et al., "Synthesis of Zeolite ZSM-57 and it's Catalytic Evaluation for the 1-Butene Skeletal Isomerization and N-Octane Cracking", J. Catal., 2000, vol. 196, 158-166.
Li, et al., "Metal Exchanged Ferrierites as Catalysts for the Selective Reduction of NO with Methane", Appl. Catal. B Environ., 1993, vol. 3, L1-L11.
Lin et al., "In silico screening of carbon-capture materials", Nature Materials, 2012, 11, 633-641.
Liu, et al., Differences in AL Distribution and Acidic Properties Between RTH-Type Zeolites Synthesized with OSDAs and without OSDAs, Nov. 8, 2014, vol. 16, 4155-64.
Lorgouilloux et al., "IM-16: A new microporous germanosilicate with a novel framework topology containing d4r and mtw composite building units", Journal of Solid State Chemistry, Mar. 2009, 182, 622-629.
Mahammed et al, "Highly Selective Chlorosulfonation of Tris(Pentafluorophenyl) Corrole as a Synthetic Tool for the Preparation of Amphiphilic Corroles and Metal Complexes of Planar Chirality", Organic Letters, Nov. 1, 2001, vol. 3(22), 3443-3436.
Martens, et al., "Tailored Alkene Oligomerization with H-ZSM-57 Zeolite", Angew Chemie. 2000, vol. 39(23), 4376-4379.
Martin, et al., "Efficient Synthesis of the Cu-SSZ-39 Catalyst for DeNOx Applications", Royal Society of Chemistry Journal, Jan. 2012, 4 pgs.
Martin, et al., "Efficient Synthesis of the Cu-SSZ-39 Catalyst for DeNOx Applications (Electronic Supplementary Information)" Royal Society of Chemistry Journal, 2015, 10 pgs.
Martinez, et al., "Inorganic Molecular Sieves: Preparation, Modification and Industrial Application in Catalytic Processes" Chem. Reviews, Mar. 2011, vol. 255, 1558-1580.
Meng, et al., "Green Routes for Synthesis of Zeolites", Chemical Reviews, 2014, vol. 114, 1521-43.
Moliner et al., "Towards thje rational design of efficient organic structure-directing agents for zeolite synthesis", Agnew Chem International Edition, 2013, 52, 13880-13889.
Moliner, et al., "Cu-SSZ-39, an Active and Hydrothermally Stable Catalyst for the Selective Catalytic Reduction of $NO_x$", Chem. Commun., 2012, 48(66), 8264-8266.
Nakagawa, et al. "Guest/host Relationships in Zeolite Synthesis: Ring-Substituted Piperidines and the Remarkable Adamantane Mimicry by 1-azonio Spiro [5.5] Undecanes" Microporous and Mesoporous Materials, 1998, vol. 22, 69-85.
Okun, et al, "Manganese Corroles Prevent Intracellular Nitration and Subsequent Death of Insulin-Producing Cells", ACS Chemical Biology, Aug. 28, 2009, vol. 4(11), 910-914.
Olsbye, et al., "Conversion of Methanol to Hydrocarbons: How Zeolite Cavity and Pore Size Controls Product Selectivity", Angew. Chem. Int. Ed., Apr. 2012, vol. 51(24), 5810-5831.
Paillaud et al., "Extra-Large-Pore Zeolites with Two-Dimensional Channels Formed by 14 and 12 Rings", Science, May 2004, 304, 990-992.
Palatinus, et al., "SUPERFLIP—A Computer Program for the Solution of Crystal Structures by Charge Flipping in Arbitrary Dimensions", J. Appl. Cryst., Aug. 2007, vol. 40(4), 786-790.
Palmer, "Transition Metal Corrole Coordination Chemistry", Struct. Bond, Sep. 14, 2011, vol. 142, 49-90.
Pophale, et al. "Computational Prediction of Chemically Synthesizable Organic No structure Directing Agents for Zeolites" Journal of Materials Chemistry A, Apr. 26, 2013, 6750-6760.
Pophale, et al., "A Database of New Zeolite-Like Materials" Phys. Chem. Phys. Jul. 21, 2011, vol. 13, 12407-12412.
Robson, "Verified Synthesis of Zeolitic Materials", Elsevier, Netherlands, 2001, 273 pgs.
Rojas et al., "A pure silica chiral polymorph with helical pores", Agnew Chemie International Edition, 2012, 51, 3854-3856.
Rojas, et al., "Synthesis, Structure, and Optical Activity of HPM-1, 34-36 a Pure Silica Chiral Zeolite", Journal of the American Chemical Society, Jul. 18, 2013, vol. 135(32), pp. 11975-11984.
Roman-Leshkov, et al., "Impact of Controlling the Site Distribution of Al Atoms on Catalytic Properties in Ferrierite-Type Zeolites", J. Chem. C., 2011, vol. 115, 1096-1102.
Rossini, "The Impact of Catalytic Materials on Fuel Reformation", Elsevier, 2003, vol. 77, 467-484.
Saltsman et al, "Selective Substitution of Corroles: Nitration, Hydroformylation, and Chlorosulfonation", J. Am. Chem. Soc. Jun. 26, 2002, 124(25):7411-20.
Sapsford, et al., "Functionalizing Nanoparticles with Biological Molecules: Developing Chemistires that Facilitate Nanotechnology", American Chemical Society, Feb. 22, 2013, pp. 1904-2074.
Schmidt et al., "CIT-7, a crystalline, molecular sieve with pores bounded by 8 and 10-membered rings", Chemical Science, Jan. 2015, 6, 1728-1734.
Schmidt et al., "The synthesis of aluminophosphate and germanosilicate LTA using a triquaternary structure directing agent", Microporous and Mesoporous Materials, Dec. 2014, 200, 132-139.
Schmidt, et al., "Synthesis of a Specified, Silica Molecular Sieve 1-3,22-27,34-36 by Using Computationally Predicted Organic Structure-Directing Agents", Angewandte Chemic, Jun. 24, 2014, vol. 126(32), 8512-8514.
Schmidt, et al., "Facile Preparation of Aluminosilicate RTH Across a Wide Composition Rabge Using a New Organic Structure-Directing Agent", Chem. of Materials, Nov. 18, 2014, 7 pgs.
Schreyeck, et al., "PREFER: A New Layered (Alumino) Silicate Precursor of FER-Type Zeolite", Microporous Matter, 1996, vol. 6, 259-71.
Shvets et al., "The Role of Crystallization Parameters for the Synthesis of Germanosilicate with UTL Topology", Chemistry a European Journal, Sep. 2008, 14, 10134-10140.
Simkhovich et al, "Mono- and Binuclear Ruthenium Corroles: Synthesis, Spectroscopy, Electrochemistry, and Structural Characterization", Chem. Eur. J. 2003, vol. 9(1), 201-208.
Simkhovich et al, "Synthesis and Characterization of Germanium, Tin, Phosphorus, Iron, and Rhodium Complexes of Tris(pentafluorophenyl) Corrole, and the Utilization of the Iron and Rhodium Corroles as Cyclopropanation Catalysts", Chem. Eur. J., 2001, vol. 7(5), 1041-1055.
Smeets et al., "Using FOCUS to solve zeolite structures from three-dimensional electron diffraction data", Journal of Applied Crystallography, Aug. 2013, 46, 1017-1023.
Smeets, et al., "SSZ-45: A High-Silica Zeolite with Small Pore Openings, Large Cavities and Unusual Adsorption Properties", Chem. Mater, May 30, 2014, 12 pgs.
Tamura, et al, "Mechanism of Hydroxylation of Metal Oxide Surfaces", Journal of Colloid and Interface Sci., Nov. 2001, vol. 243(1), 202-207.
Tang, L., et al., "A Zeolite Family with Chiral and Achiral Structures Built from the Same Building Layer" Nature Materials, 2008, vol. 7, 381-385.
Tijsebaert, et al., "Shape-Selective Synthesis of Methylamines Over the RRO Zeolite A1-RUB-41", J. Catal., 2011, vol. 278, 246-252.
Toby, "CMPR—A Powder Diffraction Toolkit", Appl. Cryst., Aug. 13, 2005, vol. 38, 1040-1041.
Tortora et al, "Supramolecular Sensing Mechanism of Corrole Thin Films", Sensors and Actuartors B, 2013, vol. 187, 72-77.

(56) References Cited

OTHER PUBLICATIONS

Tsuda et al., "Catalytic Hydrogenation of Dimethylpyridine Methiodides and Stereochemistry of Hydrogenation Products," Chemical and Pharmaceutical Bulletin, 1970, vol. 18(12), 2499-2506.

Tsuiji, et al., "Synthesis of 4,4'-trimethylenebis(1-benzyl-1-methylpiperidinium) diastereomers and their use as structure-directing agents in pure-silica molecular sieve syntheses", Microporous and Mesoporous Materials, 28(3), May 1999, 519-530.

Vermeiren, et al., "Impact of Zeolites on the Petroleum and Petrochemical Industry", Top Catal, May 15, 2009, vol. 52, 1131-1161.

Vidaysky, et al., "Light-Induced Olefin Metathesis", J. Org. Chem., Nov. 23, 2010, vol. 6, 1106-19.

Viskota, et al., "Surface Functionalization of Barium Titanate SHG Nanoprobes for In Vivo Imaging in Zebrafish", Protocol, vol. 7(9), Aug. 9, 2012, pp. 1618-1633.

Vortmann, et al., "Synthesis and Crystal Structure of the New Borosilicate Zeolite RUB-13", Microporous Materials, 1995, vol. 4, 111-21.

Wagner et al., "Guest Relationship in the Synthesis of the Novel Cage-Based Zeolites SSZ-35, SSZ-36, and SSZ-39", J. Am. Chem. Soc., Dec. 1999, 122(2), 263-273.

Wan, et al., "Three-Dimensional Rotation Electron Diffraction: Software RED for Automated Data Collection and Date Processing" J. Appl. Cryst., Dec. 2013, vol. 46, 1863-1873.

Wang, et al., "Characteristics of High Efficiency Dye-Sensitized Solar Cells." Journal of Physical Chemistry B, vol. 110, 2006, pp. 25210-25221.

Wang, et al., "Dealumination of Zeolites-II. Kinetic Study of the Dealumination by Hydrothermal Treatment of a $NH_4NaY$ Zeolite", J. Catal., Aug. 1991, vol. 130(2), 459-470.

Wang, et al., "Synthesis and Crystal Structure of Zeolite RUB-41 Obtained as Calcination Product of a Layers Precursor: A Systematic Approach to a New Synthesis Route", Chem. Matter, 2005, vol. 17, 43-49.

Weaver. "Corrales." PhD Thesis—California Institute of Technology, May 5, 2005. pp. i-xvi and 1-116.

Werner, et al., "TREOR, A Semi-Exhaustive Trial-and Error Powder Indexing Program for all Symmetries", J. Appl. Cryst., Oct. 1985, vol. 18, 367-370.

Wu et al., "Mesoporous SSZ-13 Zeolite Prepared by a Dual-Template Method with Improved Performance in the Methanol-to-Olefins Reaction", J. Catal., Feb. 2013, vol. 298, 27-40.

Yilmaz, et al., "Al-RUB-41: A Shape-Selective Zeolite Catalyst from a Layered Silicate" Chem. Commun., Nov. 22, 2011, vol. 47, 1812-4.

Yilmaz, et al., "Catalytic Applications of Zeolites in Chemical Industry", Top Catal, 2009, vol. 52, 888-895.

Yokoi, et al., "Diversification of RTH-Type Zeolite and it's Catalytic Application", Angew Chem., 2009, vol. 48, 9884-87.

Yoshioka, et al., "Preperation of RTH-Type Zeolites with the Amount and/or Kind of Organic Structure-Directing Agents (OSDA): Are OSDA'S Indispensable for the Crystallization?", Microporous and Mesoporous Materials, 2012, vol. 153, 70-78.

Yuen, et al., "Product Selectivity in Methanol to Hydrocarbon Conversion for Isostructural Compositions of AFI and CHA Molecular Sieves", Microporous Mater., Feb. 1994, 2(2), 105-117.

Zeolyst, "New Perspectives and Challenges for the Zeolite Industry", Annual Meeting in Seoul, Aug. 29, 2013, 24 pgs.

Zhang, et al., "Collecting 3D Electron Diffraction Data by the Rotation Method", 2010, vol. 225, 94-102.

Zhao, et al., "Characteristics of the Synthetic Heulandite-Clinoptilolite Family of Zeolites", Micro and Meso Materials, Feb. 4, 1998, vol. 21, 371-379.

Zones et al., "Synthesis of High Silica Zeolites Using a Mixed Quaternary Ammonium Cation, Amine Approach: Discovery of Zeolite SSZ-47", Dec. 29, 2001, Chemistry of Materials, vol. 14, No. 1, 313-320.

Zones et al., "Translating new materials discoveries in zeolite research to commercial manufacture", Microporous and Mesoporous Materials, 2011, 144, 1-8.

Zones, et al., "Searching for New High Silica Zeolites Through a Synergy of Organic Templates and Novel Inorganic Conditions", Micro and Meso Materials, 1998, vol. 21, 199-211.

Zones, et al., "Strategies in Developing Routes to Commercialization of Novel High Silica Zeolites", Studies in Surface Science and Catalysis, 2005, vol. 158, 10 pgs.

Pinar et al: "Location of Ge and extra-framework species in the zeolite ITQ-24", DAL TON Transactions, vol. 44, No. 13, Jan. 1, 2015 (Jan. 1, 2015), pp. 6288-6295, XP055515909, GB, ISSN: 1477-9226, DOI: 0.1039/C4DT03831B.

Mathias Dodin et al: "A Zeolitic Material with a Three-Dimensional Pore System Formed by Straight 12- and 10-Ring Channels Synthesized with an Imidazolium Derivative as Structure-Directing Agent", Journal of the American Chemical Society, vol. 132, No. 30, Aug. 4 2010 (Aug. 4 2010), pp. 10221-10223, XP055283237, US, ISSN: 0002-7863, DOI: 10.1021/ja103648k.

Chen et al.: "An Extra-Large-Pore Leone with intersecting 18-, 12-, and 1U-Membered Ring Channels", Angewandte Chemie International Edition, vol. 53, No. 36, Jul. 11, 2014 (Jul. 11, 2014), pp. 9592-9596, XP055515790, ISSN: 1433-7851, DOI: 10.1002/anie 201404608; -8, Fei-Jian Chen et al: "Supporting Information - an Extra-LargePore Zeolite with Intersecting 18-, 12-, and 1 a-Membered Ring Channels", Angewandte Chemie International Edition, vol. 53, No. 36, Sep. 1, 2014 (Sep. 1, 2014), pp. 1-12, XP055515794, ISSN: 1433-7851.

* cited by examiner

FIG. 1(A)
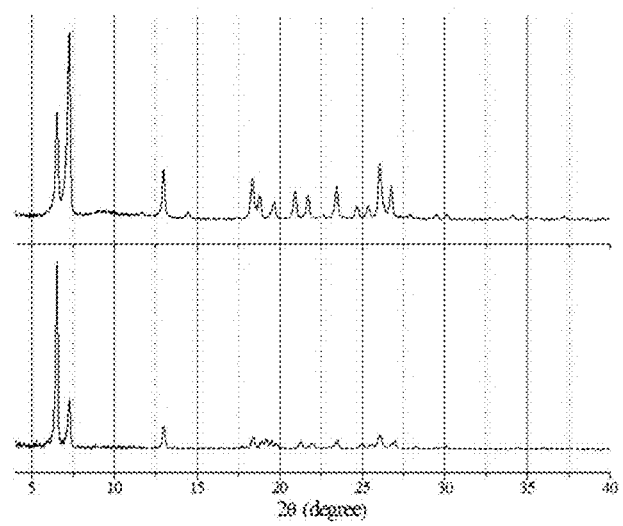
FIG. 1(B)
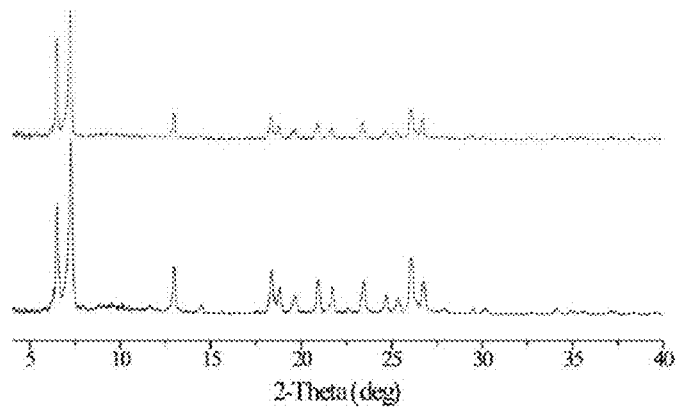
FIG. 1(C)

CIT-13

CIT-13

UTL

UTL $^{13}$C Chemical Shift (ppm)

CRYSTALLINE GERMANOSILICATE MATERIALS OF NEW CIT-13 TOPOLOGY AND METHODS OF PREPARING THE SAME

CROSS REFERENCE TO RELATED APPLICATIONS

This application claims priority to U.S. Patent Application No. 62/169,310, filed Jun. 1, 2015, the contents of which are incorporated by reference herein in their entireties for all purposes.

TECHNICAL FIELD

The present disclosure is directed to novel crystalline germanosilicate compositions and methods of producing the same. In particular, the disclosure describes extra-large-pore crystalline germanosilicate compositions, designated CIT-13, possessing 10- and 14-membered rings. The disclosure also describes methods of preparing these crystalline compositions using organic structure-directing agents (OSDAs), and methods of using these crystalline compositions.

BACKGROUND

Zeolites play an important role as heterogeneous catalysts and are used in a variety of industrial settings. Initially, these materials were largely developed to support the petroleum industry in the quest to create more selective, robust catalysts for making gasoline and other fuels. Currently, these solids have emerged as specialty materials, with properties that are based upon structure and chemical composition able to handle specific large-scale applications. A notable current example is their use in the selective catalytic reduction (SCR) system that reduces nitrous oxide emissions from on-road combustion engines. While there is a considerable effort that must go into bringing a new material from the discovery phase into a commercially viable catalyst, there remains room for discovery of new structures with the hope that one might emerge as superior to the existing materials.

One goal toward finding new materials has been the hope that increasingly large pores that retain some catalytic properties in their interior surfaces can be capable of handling larger feed molecules in the oil upgrade arena.

Hence, interest remains in the discovery of new crystalline phases for use in these applications. The present work is aimed at addressing the deficiencies in the art.

SUMMARY

This disclosure describes the results of studies with a series of monoquaternary and diquaternary OSDAs each with different aromatic ring substitutions. By investigating the phase selectivity and kinetic behavior of these OSDAs as a function of synthesis conditions, a new crystalline germanosilicate phase was discovered. The latter has been termed CIT-13, and has been shown to possess a three dimensional framework having pores defined by 10- and 14-membered rings. It is the first known crystalline silicate with this architecture.

Some embodiments, then, provide for a crystalline germanosilicate composition comprising a three dimensional framework having pores defined by 10- and 14-membered rings.

The crystalline microporous germanosilicate compositions may also, or alternatively, be described as exhibiting at least one of:

(a) a powder X-ray diffraction (XRD) pattern exhibiting at least five of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ;

(b) a powder X-ray diffraction (XRD) pattern substantially the same as shown in FIG. 1(B) or FIG. 1(C); or (c) unit cell parameters substantially equal to the following:

| Space group | Cmmm |
|---|---|
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1) |

The crystalline germanosilicate compositions have frameworks, wherein the pore dimensions of the 10- and 14-membered rings are 6.2×4.5 Å and 9.1×7.2 Å, respectively. Additionally, in some embodiments, the framework may have a density of 16.4 tetrahedral atoms ("T-atoms") per nm$^3$. In some cases, the crystalline germanosilicate have a ratio of Si:Ge atoms in a range of from 2:1 to 16:1.

The crystalline germanosilicate compositions may be prepared using, and in some cases contain, at least one substituted benzyl-imidazolium organic structure-directing agent (OSDA). Exemplary such substituted benzyl-imidazolium organic structure-directing agents include those having a structure:

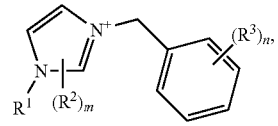

but not

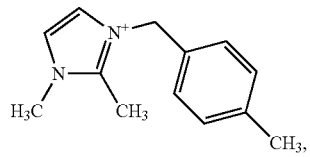

wherein m and n are independently 1, 2, or 3, and $R^1$, $R^2$, and $R^3$ are independently at each occurrence $C_{1-3}$ alkyl.

The disclosure also contemplates aqueous compositions comprising:
(a) a source of silicon oxide
(b) a source of germanium oxide;
(c) a mineralizing agent;
(d) at least one substituted benzyl-imidazolium organic structure-directing agent (OSDA) as described above and elsewhere herein; and
(e) a crystalline microporous germanosilicate CIT-13 composition. Within this specification, the nature of the sources of silicon and germanium oxide and the nature of the mineralizing agent are also described.

The disclosure also contemplates methods for preparing such germanosilicate CIT-13 compositions, the methods comprising hydrothermally treating an aqueous composition comprising:

(a) a source of silicon oxide
(b) a source of germanium oxide;
(c) a mineralizing agent;
(d) at least one substituted benzyl-imidazolium organic structure-directing agent (OSDA) having a structure:

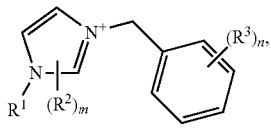

but not

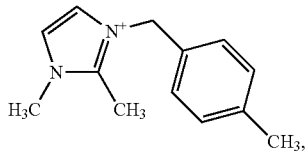

wherein m and n are independently 1, 2, or 3, and $R^1$, $R^2$, and $R^3$ are independently at each occurrence $C_{1-3}$ alkyl, under conditions effective to crystallize a crystalline microporous germanosilicate composition of the inventive topology and/or any of the characteristics associated with this inventive material. Again, the sources of silicon and germanium oxide and the nature of the mineralizing agent and operable conditions are described herein.

Once isolated, the crystalline microporous germanosilicate solid products may be further treated, for example by (a) heating at a temperature in a range of from about 250° C. to about 450° C.; or (b) contacting with ozone or other oxidizing agent at a temperature in a range of 25° C. to 200° C.;

for a time sufficient to form a dehydrated or an OSDA-depleted product.

In other embodiments, the isolated crystalline microporous germanosilicate compositions may be further treated by:

(a) treating the dehydrated or OSDA-depleted product with an aqueous alkali, alkaline earth, transition metal, rare earth metal, ammonium or alkylammonium salt; and/or (b) treating the dehydrated or OSDA-depleted product with at least one type of transition metal or transition metal oxide.

In other embodiments, the isolated germanosilicate solid products are calcined in air or under inert atmosphere conditions at a temperature in a range of from about 600° C. to about 1200° C., preferably about 800° C. to about 1000° C., for about 4-8 hours. Longer or shorter times may also be employed.

The inventive materials may be used in a host of catalysis applications which are also described herein.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIGS. 1(A-C) shows several sets of powder XRD patterns for CIT-13: FIG. 1(A) shows CIT-13 as made (upper) and calcined (lower); FIG. 1(B) shows reproducibility of patterns of products made from gels with Si/Ge=4.

FIGS. 2(A-B) shows the CIT-13 pore system seen from (A) the 14MR-portal direction and (B) the 10MR-portal direction. FIGS. 2(C-D) show the UTL pore system seen from (C) the 14MR-portal direction and (D) the 12MR-portal direction.—dashed circles indicate location of germanium oxides within the lattice. FIGS. 2(F-G) show SEM micrographs of as-prepared CIT-13 crystals from rotating and static convection ovens, respectively.

FIG. 18 (E) Cryogenic Argon adsorption and desorption isotherms of CIT-13 from HF-protocol and NH$_4$F-protocol at 87 K.

DETAILED DESCRIPTION OF ILLUSTRATIVE EMBODIMENTS

The present invention is directed to new compositions of matter, including those comprising crystalline microporous germanosilicates, and methods of making and using these compositions The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Compositions

The present invention is directed to a novel set of compositions described collectively as CIT-13. In some embodiments, the novel compositions are described in terms of crystalline microporous germanosilicate compositions comprising a three dimensional framework having pores defined by 10- and 14-membered rings. As should be apparent from the descriptions herein, these 10- and 14-membered rings comprise silicon-oxygen and germanium-oxygen linkages. The 10- and 14 membered rings are defined by convention as referring to the number of alternating oxygen atoms in the respective rings and not the total number of atoms. Additionally, this number of oxygen atoms in the ring also equals the number of tetrahedral atoms in the ring.

Figure 1C:
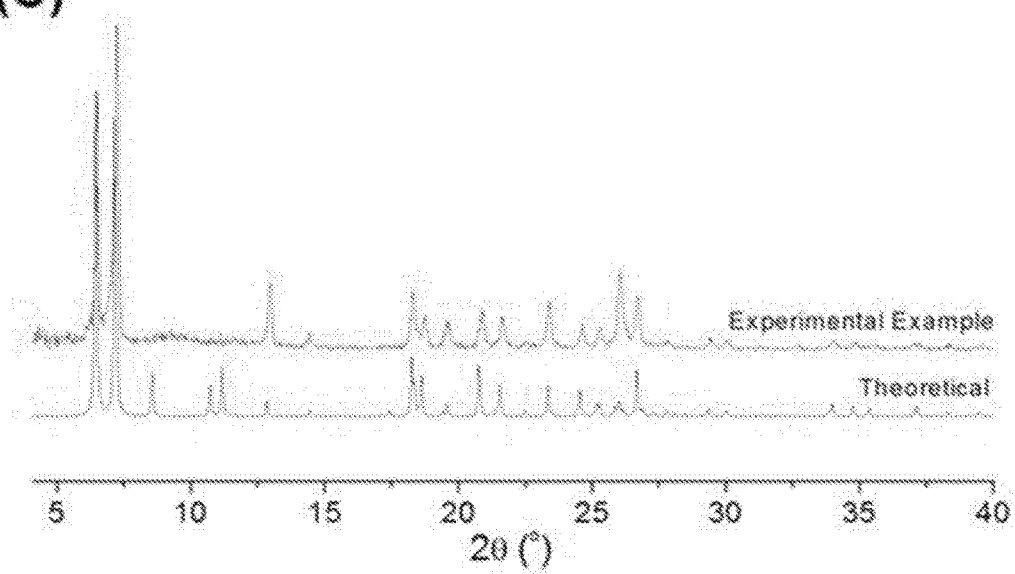
FIG. 1(C) compares experimentally and theoretically derived sample.

In other embodiments, the crystalline microporous germanosilicate compositions may be described in terms of those compositions that exhibit at least one of characteristics: (a) a powder X-ray powder diffraction (XRD) pattern exhibiting at least five of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ; (b) a powder X-ray powder diffraction (XRD) pattern substantially the same as shown in FIG. 1(A), 1(B) or 1(C); or (c) unit cell parameters substantially equal to the following:

| Space group | Cmmm |
|---|---|
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1) |

The crystalline compositions may exhibit one, two, or all three of the characteristics described in (a), (b), or (c). In addition to these features, these crystalline microporous germanosilicates may also be separately or additionally characterized and/or defined in any of the adsorption/desorption properties or $^1$H, $^{13}$C, or $^{29}$Si NMR data provided herein (for example, as provided at least in FIGS. 14-17).

It should be appreciated that these crystalline germanosilicates may also be characterized/defined in terms of any combination of structural and physical data. Similarly, while it is believed that the structures described herein are true and accurate, the novelty of these new materials is not necessarily defined by the exactness of the descriptions of these structures, should any future information be identified that later causes a re-characterization of the structure. Similarly, as the physical data are may be effected by experimental artifacts, the exactness of any specific data point may be subject to such experimental variability.

As described above, the crystalline microporous germanosilicate compositions may be defined in terms of their powder X-ray diffraction (XRD) pattern, as exhibiting at least five of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ. In separate embodiment, the composition may exhibits six, seven, eight, nine, or ten of these characteristic peaks. Likewise, in other embodiment, the composition may exhibit 5, 6, 7, 8, 9, 10, or more of the peaks identified in Table 3.

In other embodiments, the crystalline compositions exhibit a powder X-ray powder diffraction (XRD) pattern substantially the same as shown in FIG. 1(A), 1(B) or 1(C). Note here that the relative intensities of the peaks shown in these or any other figures, or identified in Table 3 may be subject to experimental variations, for example due to scanning speed, sample separation, particle size, degree if crystallinity (e.g., related to degree of heat processing). For example, pre-calcined materials isolated from the mixtures used to prepare them, may exhibit broader peaks than those same materials post-heat treatment or post-calcination. Such variability is reflected, in part, by any differences in the various XRD patterns described in the instant application. The person of skill in the art in this area would appreciate the significance of any such variations.

A single cell crystal structure has been analyzed as described in the Examples, whose structural characteristics are described there. So, in still other embodiments, the crystalline compositions exhibit unit cell parameters substantially equal or equivalent to the following:

| Space group | Cmmm |
|---|---|
| a (Å) | 27.4374(5) |
| b (Å) | 13.8000(2) |
| c (Å) | 10.2910(2) |
| V (Å³) | 3896.6(1) |
| Z | 8 |
| ρ (g/cm³) | 2.144(2) |
| λ (Å) | 0.776381(1) |

Crystallographic evidence also has shown that the channel dimensions of the 10- and 14-membered rings are 6.2×4.5 Å and 9.1×7.2 Å, respectively. Additionally, in some embodiments, the crystalline framework may have a density of 16.4 tetrahedral atoms ("T-atoms") per nm³.

Figure 12A:
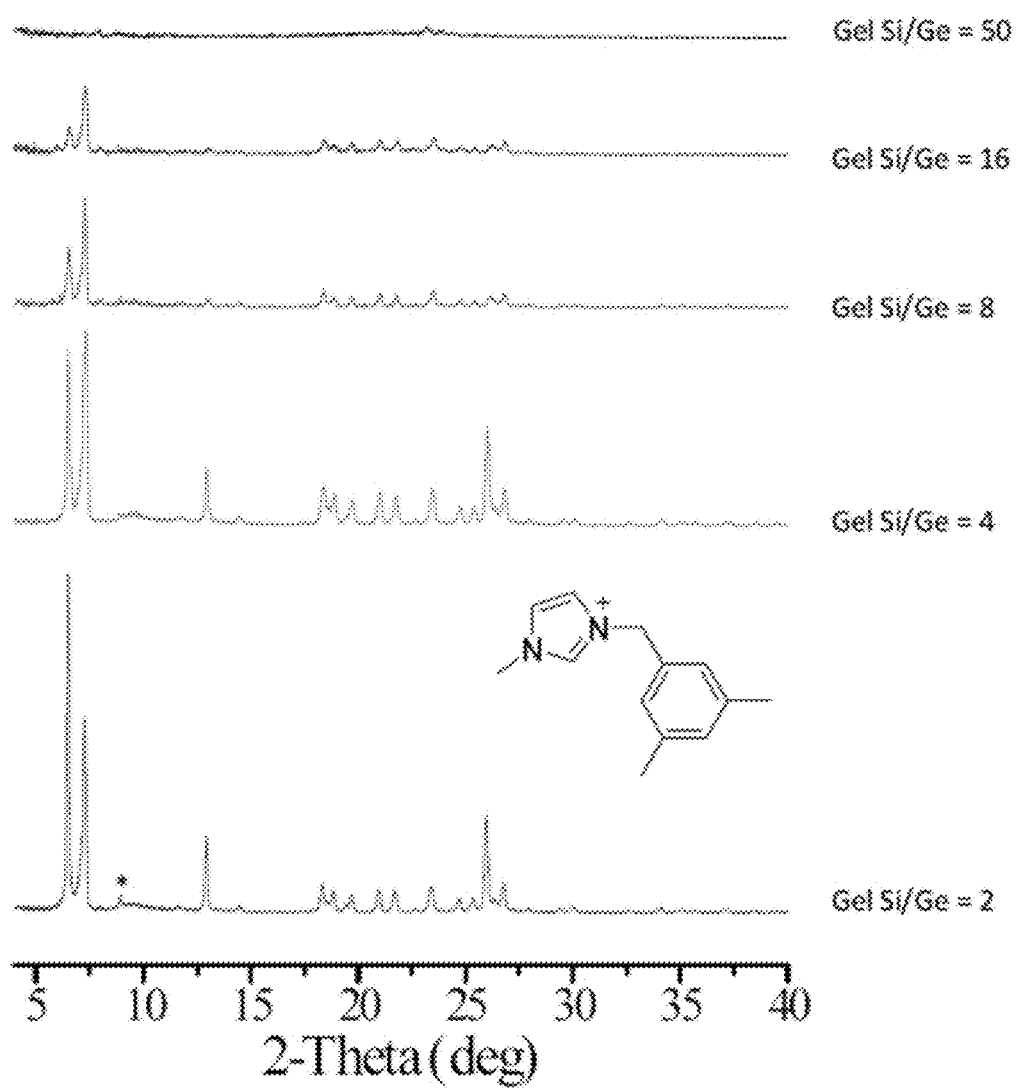
FIG. 12(A) shows XRD profiles of crystallized germanosilicate samples with various gel Si/Ge ratios from OSDA 6. Asterisks (*) denote impurity peaks.
Figure 12B:
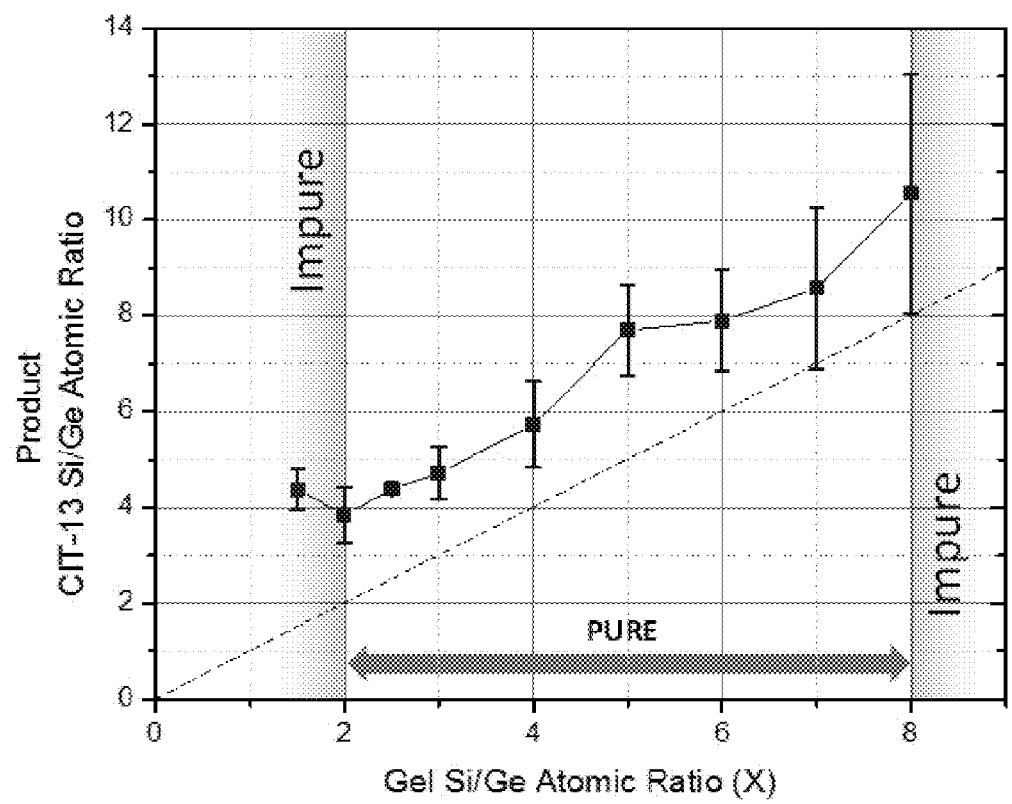
FIG. 12(B) shows the relationship between the gel Si/Ge ratio and the product CIT-13/GE ratios, as characterized by EDS.

In certain embodiments, the crystalline compositions of the present can have a ratio of Si:Ge atoms within any one or more of the ranges of from 1:1 to 2:1 (or lower), from 2:1 to 3:1, from 3:1 to 4:1, from 4:1 to 5:1, from 5:1 to 6:1, from 6:1 to 7:1, from 7:1 to 8:1, from 8:1 to 9:1, from 9:1 to 10:1, from 10:1 to 11:1, from 11:1 to 12:1, from 12:1 to 13:1, from 13:1 to 14:1, from 14:1 to 15:1, from 15:1 to 16:1 or higher. As shown in FIG. 12(B), and the supporting XRD patterns, high purities have been achieved throughout the range of ratios of from about 4:1 to about 16:1.

Depending on the processing of the crystalline compositions, these compositions may contain the organic structuring agent (OSDA) used in their preparation, or may be substantially free or devoid of any such OSDA (the terms "substantially" and "substantially devoid" are analogous to the term "OSDA depleted" described elsewhere herein). The specific structuring agents used to prepare these crystalline compositions are also described elsewhere herein.

The presence of these OSDAs may be identified using, for example, $^{13}C$ NMR or any of the methods defined in the Examples. It is a particular feature of the present invention that the cationic OSDAs retain their original structures, including their stereochemical conformations during the synthetic processes, these structures being compromised during the subsequent calcinations or oxidative treatments.

In some embodiments, where HF or other source of fluoride is used that the mineralizing agent, the pores may additionally comprise fluoride (as evidenced by $^{19}F$ NMR). In other embodiments, either when using mineralizing agents not containing fluoride or otherwise if any potential fluoride flushed or displaced from compositions, the compositions are substantially fluoride-free.

The disclosed crystalline microporous germanosilicate compositions include those which result from the post-treatment or further processing described in the following Methods section of this disclosure. These include germanosilicates in their hydrogen forms or those having cations, metals or metal oxides within their pore structures. Accordingly, in certain embodiments, the microporous pure or substituted germanosilicates contain Li, Na, K, Rb, Cs, Be, Mg, Ca, Sr, Be, Al, Ga, In, Zn, Ag, Cd, Ru, Rh, Pd, Pt, Au, Hg, La, Ce, Pr, Nd, Pm, Sm, Eu, or $R_{4-n}N^+H_n$ cations, where R is alkyl, n=0-4 in at least some of their pores. In specific aspects of these embodiments, these pores contain NaCl or KCl.

Additional embodiments include those crystalline microporous solids of the present disclosure, at least some of whose pores transition metals, transition metal oxides, or salts, said metals including, for example scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one specific embodiment, the pores of the germanosilicate solids contain copper, as metal, oxide, or salt.

Methods of Preparing the Inventive Compositions

Certain embodiments of the present disclosure include methods for preparing crystalline microporous germanosilicate compositions, each method comprising hydrothermally treating an aqueous composition comprising:
(a) a source of silicon oxide
(b) a source of germanium oxide;
(c) a mineralizing agent;
(d) at least one substituted benzyl-imidazolium organic structure-directing agent (OSDA) having a structure:

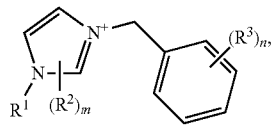

but not

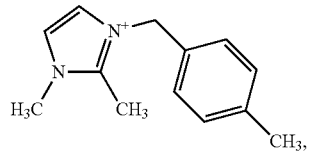

wherein m and n are independently 1, 2, or 3, and $R^1$, $R^2$, and $R^3$ are independently at each occurrence $C_{1-3}$ alkyl, preferable where $R^1$, $R^2$, and $R^3$ are independently ethyl or methyl, more preferably where $R^1$, $R^2$, and $R^3$ are methyl, under conditions effective to crystallize a crystalline microporous germanosilicate composition having a structure or exhibiting a characteristic associated with the inventive compositions.

The source of silicon oxide, as described above, may comprise a silicate, silica hydrogel, silicic acid, fumed silica, colloidal silica, tetra-alkyl orthosilicate, a silica hydroxide or combination thereof. Sodium silicate or tetraorthosilicates, for example tetraethyl orthosilicate (TEOS), are preferred sources. The sources of silicon oxide may be amorphous (i.e., the XRD pattern of the solid showing little or no structure), microcrystalline (i.e., the XRD pattern of the solid showing broadened reflectance peaks indicative of a small degree of long range order), or crystalline (i.e., the XRD pattern of the solid showing well defined and sharp reflectance peaks).

Sources of germanium oxide can include alkali metal orthogermanates, $M_4GeO_4$, containing discrete $GeO_4^{4-}$ ions, $GeO(OH)_3^-$, $GeO_2(OH)_2^{2-}$, $[(Ge(OH)_4)_8(OH)_3]^{3-}$ or neutral solutions of germanium dioxide contain $Ge(OH)_4$, or alkoxide or carboxylate derivatives thereof.

Where the aqueous composition is free from any of the optional sources of metal oxides, the process yields pure crystalline microporous pure-germanosilicate materials, the term "pure" reflecting the absence of all but the inevitable impurities present in the sources of silicon or germanium oxides. The aqueous compositions may also comprise other sources of metal oxide, deliberately added, for example sources of aluminum oxide, boron oxide, gallium oxide, hafnium oxide, iron oxide, tin oxide, titanium oxide, vanadium oxide, zinc oxide, zirconium oxide, or combination or mixture thereof, in which case the resulting product may contain the corresponding metal oxide within the resulting lattice framework.

In preparing the germanosilicates, the silicon oxide and the source of germanium oxide are present in a molar ratio of Si:Ge in a range of from about 2:1 to about 8:1. Higher and lower ratios may also be used, though these tend to result in final product of lesser purities. In some embodiments, the molar ratio of Si:Ge is in at least one range of from 2:1 to 3:1, from 3:1 to 4:1, from 4:1 to 5:1, from 5:1 to 6:1, from 6:1 to 7:1, from 7:1 to 8:1, for example 3:1 to 8:1.

In some embodiments, the mineralizing agent comprises an aqueous alkali metal or alkaline earth metal hydroxide, thereby rendering these compositions alkaline. In certain of these embodiments, the alkali metal or alkaline earth metal hydroxide include LiOH, NaOH, KOH, RbOH, CsOH, $Mg(OH)_2$, $Ca(OH)_2$, $Sr(OH)_2$, or $Ba(OH)_2$. LiOH, NaOH, or KOH appear to be preferred. In some cases, the pH of the water is in a range of from 7 to 14, or greater. Under these conditions, the oxide precursors can be expected to be at least partially hydrated to their hydroxide forms.

In other embodiments, the mineralizing agent is or comprises a source of fluoride ion. Aqueous hydrofluoric acid is particularly suitable for this purpose, whether used as provided, or generated in situ by other conventional methods. Such sources of HF can include:

(a) aqueous ammonium hydrogen fluoride ($NH_4F\cdot HF$) or ammonium fluoride itself;

(b) an alkali metal bifluoride salt (i.e., $MHF_2$, where $M^+$ is $Li^+$, $Na^+$, or $K^+$), or a combination thereof; or (c) at least one fluoride salt, such as an alkali metal, alkaline earth metal, or ammonium fluoride salt (e.g., LiF, NaF, KF, CsF, $CaF_2$, tetraalkyl ammonium fluoride (e.g., tetramethyl ammonium fluoride)) in the presence of at least one mineral acid that is stronger than HF (e.g., HCl, HBr, HI, $H_3PO_4$, $HNO_3$, oxalic acid, or $H_2SO_4$) and can react with fluorides to form HF in situ; or (d) a combination of two or more of (a)-(c). Within these systems, at least, volatile sources of fluoride (e.g., HF, $NH_4F$, or $NH_4F\cdot HF$) are preferred.

The OSDAs may be described in the context of

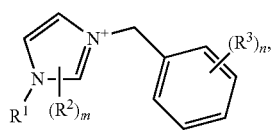

but not

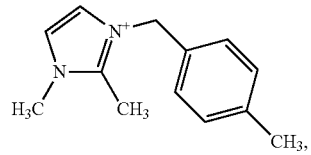

with the various options described for $R^2$ and $R^3$ described above and elsewhere herein. As shown in the Examples, the cleanest CIT-13 materials appear to be prepared from OSDAs in which the $R^3$ substituents are positioned meta to the benzylic linkage, for example:

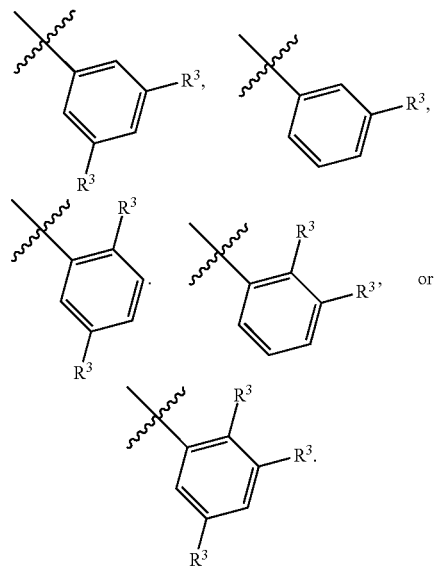

In certain embodiments, the substituted imidazolium portion of the OSDA comprises:

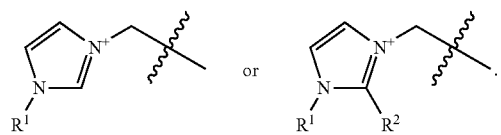

In certain embodiments, the substituted benzyl-imidazolium organic structure-directing agent has a structure:

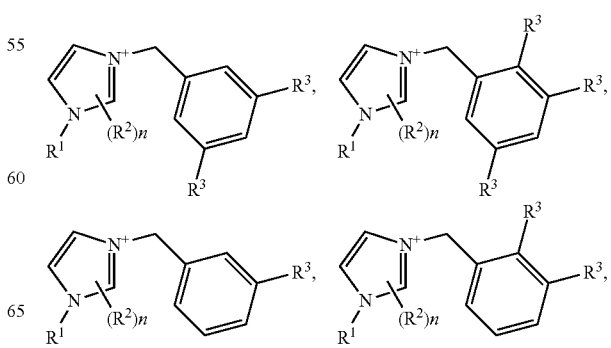

-continued

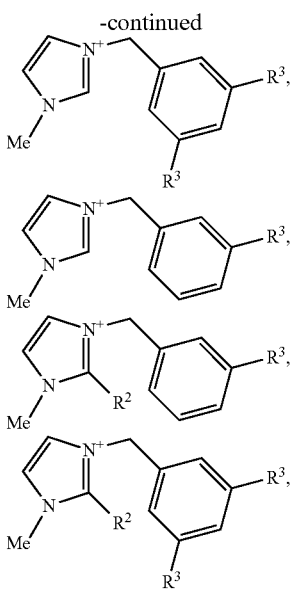

where n, $R^1$, $R^2$, and $R^3$ are any of the embodiments described elsewhere herein.

In more specific embodiments, the at least one substituted benzyl-imidazolium organic structure-directing agent has a structure (each structure being considered an independent embodiment):

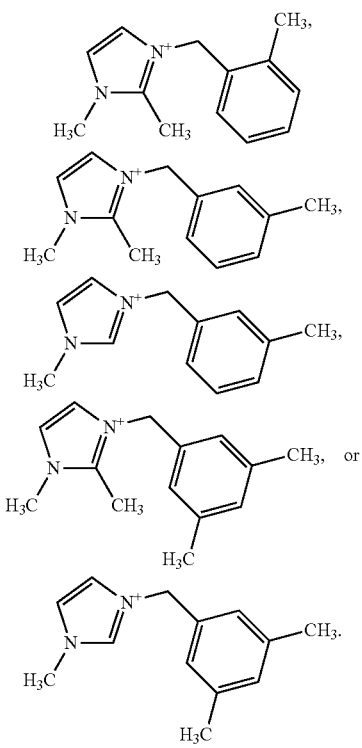

The counterion to the OSDA's described herein, at least as added to the reaction mixture, are typically bromide, chloride, fluoride, iodide, or hydroxide ion, but the OSDA may be added also to the composition as an acetate, nitrate, or sulfate. In some embodiments, the quaternary cation has an associated fluoride or hydroxide ion, preferably substan-tially free of other halide counterions. In separate embodiments, the associated anion is hydroxide.

The processes and compositions may further be defined in terms of the ratios of other of the individual ingredients. In certain embodiments, the molar ratio of the OSDA:Si is in a range of from 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.55, from 0.55 to 0.6, from 0.6 to 0.65, from 0.65 to 0.7, from 0.7 to 0.75, from 0.75 to 0.8, from 0.8 to 0.85, from 0.85 to 0.9, from 0.9 to 0.95, from 0.95 to 1, or a range combining any two or more of these ranges, for example from 0.4 to 0.6 or from 0.4 to 0.75.

In other embodiments, the molar ratio of water:Si is in a range of from about 2 to 3 (i.e., 2:1 to 3:1), from 3 to 4, from 4 to 5, from 5 to 6, from 6 to 7, from 7 to 8, from 8 to 9, from 9 to 10, from 10 to 11, from 11 to 12, from 12 to 13, from 13 to 14, from 14 to 15, from 15 to 16, from 16 to 17, from 17 to 18, from 18 to 19, from 19 to 20, or a range combining any two or more of these ranges, for example in a range of from about 2 to about 10, from about 3 to 10, or from 3 to 8.

Where the mineralizing agent is a fluoride source, such as HF, the molar ratio of fluoride:Si may be in a range of from about 0.1 to 0.15, from 0.15 to 0.2, from 0.2 to 0.25, from 0.25 to 0.3, from 0.3 to 0.35, from 0.35 to 0.4, from 0.4 to 0.45, from 0.45 to 0.5, from 0.5 to 0.55, from 0.55 to 0.6, from 0.6 to 0.65, from 0.65 to 0.7, from 0.7 to 0.75, or a range combining any two or more of these ranges, for example in a range of from about 0.4 to about 0.6.

To this point, the processes have been defined in terms of conditions under conditions effective to crystallize a crystalline microporous germanosilicates of CIT-13 topology. In light of the other teachings within this disclosure, this is believed to be a sufficient description. But in certain aspects of this, these conditions include treatment of the respective hydrothermally treated aqueous composition at a temperature defined by at least one range of from 100° C. to 110° C., from 110° C. to 120° C., from 120° C. to 125° C., from 125° C. to 130° C., from 130° C. to 135° C., from 135° C. to 140° C., from 140° C. to 145° C., from 145° C. to 150° C., from 150° C. to 155° C., from 155° C. to 160° C., from 160° C. to 165° C., from 165° C. to 170° C., from 170° C. to 175° C., from 175° C. to 180° C., from 180° C. to 185° C., from 185° C. to 190° C., from 190° C. to 195° C., from 195° C. to 200° C., for example, from 120° C. to 160° C. In related embodiments, the times of this treatment, while dependent on the specific reaction conditions (e.g., temperatures and concentrations), can range from 3 to 40 days, preferably from 7 to 40 days. These ranges provide for convenient reaction times, though higher and lower temperatures and longer or shorter times may also be employed. This hydrothermal treating is also typically done in a sealed autoclave, at autogenous pressures. Additional exemplary reaction conditions are provided in the Examples.

As discussed at least in the Examples, the synthesis of novel extra-large-pore framework CIT-13 has been demonstrated in a wide range of synthetic variables. Using the monoquaternary OSDAs belonging to the methylbenzylimidazolium family and the dimethylbenzylimidazolium family, an optimized condition for CIT-13 is suggested as follows: the gel composition at Si/Ge=3-8, $H_2O/T$=5-7.5 (where "T" refers to the total number of Si and Ge atoms); OSDA+F-/T=0.5 using 1-methyl-3-(3,5-dimethylbenzyl) imidazolium or 1,2-dimethyl-3-(3-methylimidazolium as the OSDA in a 140° C.-180° C. static/rotating oven for 1-3 weeks.

In some embodiments the reaction mixture, which may be a suspension or a gel, or a gelling suspension, can be subjected to mild stirring or rolling agitation during crystallization. It will be understood by a person skilled in the art that the as produced crystalline microporous solid s described herein can contain impurities, such as amorphous materials, or materials having framework topologies which do not coincide with the targeted or desired product. During hydrothermal crystallization, the crystals can be allowed to nucleate spontaneously from the reaction mixture.

The use of crystals of the desired crystalline product as seed material can result in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 0.01% and 10%, for example, 1%, of the mass of the total amount of oxide in the reaction mixture. The total amount of oxide refers to the total mass of oxides in the reaction mixture gel prior to heating, present as the oxides or oxide sources.

Once the initially-formed crystalline solids of the CIT-13 topology are prepared (e.g., including pure or substituted germanosilicates), further embodiments comprise isolating these solids. These crystalline solids may be removed from the reaction mixtures by any suitable means (e.g., filtration, centrifugation, etc. or simple removal of the membrane template) and dried. Such drying may be done in air or under vacuum at temperatures ranging from 25° C. to about 200° C. Typically, such drying is done at a temperature of about 100° C.

As shown in the various Examples, the methods described herein produce or are capable of producing compositionally "clean" crystalline microporous materials. That is, in various embodiments, the crystalline microporous materials described herein are at least 75%, 80%, 85%, 90%, 95%, or 98% by weight of the nominal topology. In some embodiments, the crystalline microporous materials are sufficiently clean as to exhibit XRD patterns where other crystalline topologies are undetectable.

The crystalline microporous germanosilicate solid products, at least as initially isolated, typically contain amounts of the OSDAs used in their syntheses occluded in their pores, and these can be detected by NMR or inferred by TGA weight loss profiles, some of which are described further in the Examples. These isolated solids also may exhibit power XRD patterns consistent with the structures described herein, perhaps as broadened patterns. Residual OSDAs may be removed from the pores of the isolated solids by any number of suitable methods, for example:

(a) heating the isolated product solid at a temperature in a range of from about 250° C. to about 450° C. in an oxidizing atmosphere, such as air or oxygen, or in an inert atmosphere, such as argon or nitrogen; or (b) contacting the isolated product solid with ozone or other oxidizing agent at a temperature in a range of 25° C. to 200° C.;

for a time sufficient to form a dehydrated or an OSDA-depleted product. The resulting crystalline germanosilicate products are then substantially devoid of residual OSDA.

As used herein, the term "OSDA-depleted" (or composition having depleted OSDA) refers to a composition having a lesser content of OSDA after the treatment than before. In preferred embodiments, substantially all (e.g., greater than 90, 95, 98, 99, or 99.5 wt %) or all of the OSDA is removed by the treatment. In some embodiments, this can be confirmed by the absence of a TGA endotherm associated with the removal of the OSDA when the product material is subject to TGA analysis or the absence or substantial absence of C or N in elemental analysis (prior to heating, expect composition to comprise C, N, O, Si, Al, H).

In those embodiments where the processing involved heating, typical heating rates include is 0.1° C. to 10° C. per minute and or 0.5° C. to 5° C. per minute. Different heating rates may be employed depending on the temperature range. Depending on the nature of the calcining atmosphere, the materials may be heated to the indicated temperatures for periods of time ranging from 1 to 60 hours or more, to produce a catalytically active product.

The ozone-treatment can be carried out in a flow of ozone-containing oxygen (typically for 6 hours or more. but shorter could be feasible). Practically any oxidative environment sufficient to remove the OSDA can be used, especially those already known for this purpose. Such environments, for example, can involve the use of organic oxidizers (alkyl or aryl peroxides or peracids) or inorganic peroxides (e.g., $H_2O_2$) (alkyl or aryl peroxides or peracids.

Further processing of these materials, whether modified or not, may also comprise, heating the isolated crystalline microporous germanosilicate solid at a temperature in a range of from about 200° C. to about 600° C. in the presence of an alkali, alkaline earth, transition metal, rare earth metal, ammonium or alkylammonium salts (anions including halide, preferable chloride, nitrate, sulfate, phosphate, carboxylate, or mixtures thereof) for a time sufficient to form a dehydrated or an OSDA-depleted product. In certain of these embodiments, the heating is done in the presence of NaCl or KCl. In certain exemplary embodiments, the heating is done at a temperature in a range of from 500 to 600° C. In exemplary embodiments, the heating is done in either an oxidizing or inert atmosphere.

These crystalline microporous solids may be further modified, for example, by incorporating metals with the pore structures, either before or after drying, for example by replacing some of the cations in the structures with additional metal cations using techniques known to be suitable for this purpose (e.g., ion exchange). Such cations can include those of rare earth, Group 1, Group 2 and transition metals, for example Ca, Cd, Co, Cu, Fe, Mg, Mn, Ni, Pt, Pd, Re, Sn, Ti, V, W, Zn and their mixtures. In other specific embodiments, the metal cation salt is a copper salt, for example, Schweizer's reagent (tetraamminediaquacopper dihydroxide, $[Cu(NH_3)_4(H_2O)_2](OH)_2]$), copper(II) nitrate, or copper(II) carbonate.

The addition of a transition metal or transition metal oxide may be accomplished, for example by chemical vapor deposition or chemical precipitation. As used herein, the term "transition metal" refers to any element in the d-block of the periodic table, which includes groups 3 to 12 on the periodic table, as well as the elements of the f-block lanthanide and actinide series. This definition of transition metals specifically encompasses Group 4 to Group 12 elements. In certain other independent embodiments, the transition metal or transition metal oxide comprises an element of Groups 6, 7, 8, 9, 10, 11, or 12. In still other independent embodiments, the transition metal or transition metal oxide comprises scandium, yttrium, titanium, zirconium, vanadium, manganese, chromium, molybdenum, tungsten, iron, ruthenium, osmium, cobalt, rhodium, iridium, nickel, palladium, platinum, copper, silver, gold, or mixtures. Fe, Ru, Os, Co, Rh, Ir, Ni, Pd, Pt, Cu, Ag, Au, and mixtures thereof are preferred dopants.

In other embodiments, the optionally doped crystalline solids are calcined in air a temperature defined as being in at least one range of from 400° C. to 500° C., from 500° C. to 600° C., from 600° C. to 700° C., from 700° C. to 800° C., from 800° C. to 900° C., from 900° C. to 1000° C., from 1000° C. to 1200° C., 500° C. to about 1200° C.

Intermediate Reaction Compositions

As described herein, the as-formed and post-treated crystalline germanosilicate compositions themselves are within the scope of the present disclosure and are considered to be independent embodiments of the present invention. All of the descriptions used to describe the features of the disclosed processes yield compositions which are separately considered embodiments. In an abundance of caution, some of these are presented here, but these descriptions should not be considered to exclude embodiments provided or which naturally follow from other descriptions.

These embodiments include compositions comprising the aqueous compositions used in the hydrothermal treatments together with the respective crystalline microporous seed or product germanosilicates, wherein the germanosilicate products contain the respective OSDAs used in their preparation occluded in their pores.

For example, in some embodiments, the composition comprises:
(a) a source of silicon oxide
(b) a source of germanium oxide;
(c) a mineralizing agent;
(d) at least one of the substituted benzyl-imidazolium organic structure-directing agent (OSDA) described above, including at least one having a structure:

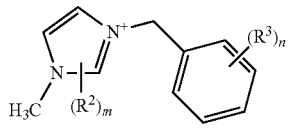

but not

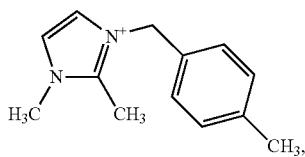

wherein m, n, $R^1$, $R^2$, and $R^3$ are as identified above and elsewhere herein; and
(e) a crystalline microporous germanosilicate compositionally consistent with the CIT-13 topology, or a seed thereof.

As used herein, the term "compositionally consistent" refers to a crystalline germanosilicate composition having a stoichiometry consistent with one resulting from the at least a partial progression of the hydrothermal treating process used to prepare these materials. Typically, these compositionally consistent crystalline microporous pure or optionally substituted germanosilicate typically contain, occluded in their pores, the OSDA used to make them; i.e., the OSDA present in the associated aqueous compositions. In separate embodiments, these compositionally consistent crystalline solids may also be substantially free of the OSDAs used in the aqueous media; in such embodiments, the optionally substituted germanosilicates may be used as seed material for the crystallization, also as described elsewhere herein.

These compositions may comprise any of the types, sources, and ratios of ingredients associated with a process described elsewhere herein, and may exist at any temperature consistent with the processing conditions described above as useful for the hydrothermal processing embodiments. It should be appreciated that this disclosure captures each and every of these permutations as separate embodiments, as if they were separately listed. In some embodiments, these compositions exist in the form of a suspension. In other embodiments, these compositions exist in the form of a gel.

Uses of the Inventive Compositions

In various embodiments, the crystalline microporous germanosilicate solids of the present invention, calcined, doped, or treated with the catalysts described herein, mediate or catalyze an array of chemical transformation. Such transformations may include carbonylating DME with CO at low temperatures, reducing NOx with methane (e.g., in exhaust applications), cracking, hydrocracking, dehydrogenating, converting paraffins to aromatics, MTO, isomerizing aromatics (e.g., xylenes), disproportionating aromatics (e.g., toluene), alkylating aromatic hydrocarbons, oligomerizing alkenes, aminating lower alcohols, separating and sorbing lower alkanes, hydrocracking a hydrocarbon, dewaxing a hydrocarbon feedstock, isomerizing an olefin, producing a higher molecular weight hydrocarbon from lower molecular weight hydrocarbon, reforming a hydrocarbon, converting lower alcohol or other oxygenated hydrocarbons to produce olefin products, epoxiding olefins with hydrogen peroxide, reducing the content of an oxide of nitrogen contained in a gas stream in the presence of oxygen, or separating nitrogen from a nitrogen-containing gas mixture by contacting the respective feedstock with the a catalyst comprising the crystalline microporous solid of any one of materials described herein under conditions sufficient to affect the named transformation. Particularly attractive applications include in which these germanosilicates are expected to be useful include catalytic cracking, hydrocracking, dewaxing, alkylation, and olefin and aromatics formation reactions. Additional applications include gas drying and separation.

Specific embodiments provide hydrocracking processes, each process comprising contacting a hydrocarbon feedstock under hydrocracking conditions with a catalyst comprising a crystalline microporous solid of this invention, preferably predominantly in the hydrogen form.

Still other embodiments provide processes for dewaxing hydrocarbon feedstocks, each process comprising contacting a hydrocarbon feedstock under dewaxing conditions with a catalyst comprising a crystalline microporous solid of this invention. Yet other embodiments provide processes for improving the viscosity index of a dewaxed product of waxy hydrocarbon feeds, each process comprising contacting the waxy hydrocarbon feed under isomerization dewaxing conditions with a catalyst comprising a crystalline microporous solid of this invention.

Additional embodiments include those process for producing a C20+ lube oil from a C20+ olefin feed, each process comprising isomerizing said olefin feed under isomerization conditions over a catalyst comprising at least one transition metal catalyst and a crystalline microporous solid of this invention.

Also included in the present invention are processes for isomerization dewaxing a raffinate, each process comprising contacting said raffinate, for example a bright stock, in the presence of added hydrogen with a catalyst comprising at least one transition metal and a crystalline microporous solid of this invention.

Other embodiments provide for dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15-3000 psi with a catalyst comprising at least one transition metal and a crystalline microporous solid of this invention, preferably predominantly in the hydrogen form.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one transition metal and a crystalline microporous solid of this invention.

Also included in this invention is a process for increasing the octane of a hydrocarbon feedstock to produce a product having an increased aromatics content, each process comprising contacting a hydrocarbonaceous feedstock which comprises normal and slightly branched hydrocarbons having a boiling range above about 40° C. and less than about 200° C., under aromatic conversion conditions with a catalyst comprising a crystalline microporous solid of this invention. In these embodiments, the crystalline microporous solid is preferably made substantially free of acidity by neutralizing said solid with a basic metal. Also provided in this invention is such a process wherein the crystalline microporous solid contains a transition metal component.

Also provided by the present invention are catalytic cracking processes, each process comprising contacting a hydrocarbon feedstock in a reaction zone under catalytic cracking conditions in the absence of added hydrogen with a catalyst comprising a crystalline microporous solid of this invention. Also included in this invention is such a catalytic cracking process wherein the catalyst additionally comprises an additional large pore crystalline cracking component.

This invention further provides isomerization processes for isomerizing C4 to C7 hydrocarbons, each process comprising contacting a feed having normal and slightly branched C4 to C hydrocarbons under isomerizing conditions with a catalyst comprising a crystalline microporous solid of this invention, preferably predominantly in the hydrogen form. The crystalline microporous solid may be impregnated with at least one transition metal, preferably platinum. The catalyst may be calcined in a steam/air mixture at an elevated temperature after impregnation of the transition metal.

Also provided by the present invention are processes for alkylating an aromatic hydrocarbon, each process comprising contacting under alkylation conditions at least a molar excess of an aromatic hydrocarbon with a C2 to C20 olefin under at least partial liquid phase conditions and in the presence of a catalyst comprising a crystalline microporous solid of this invention, preferably predominantly in the hydrogen form. The olefin may be a C2 to C4 olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, or mixtures thereof.

Further provided in accordance with this invention are processes for transalkylating an aromatic hydrocarbon, each of which process comprises contacting under transalkylating conditions an aromatic hydrocarbon with a polyalkyl aromatic hydrocarbon under at least partial liquid phase conditions and in the presence of a catalyst comprising a crystalline microporous solid of this invention, preferably predominantly in the hydrogen form. The aromatic hydrocarbon and the polyalkyl aromatic hydrocarbon may be present in a molar ratio of from about 1:1 to about 25:1, respectively. The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention are processes to convert paraffins to aromatics, each of which process comprises contacting paraffins under conditions which cause paraffins to convert to aromatics with a catalyst comprising a crystalline microporous solid of this invention, said catalyst comprising gallium, zinc, or a compound of gallium or zinc.

In accordance with this invention there is also provided processes for isomerizing olefins, each process comprising contacting said olefin under conditions which cause isomerization of the olefin with a catalyst comprising a crystalline microporous solid of this invention.

Further provided in accordance with this invention are processes for isomerizing an isomerization feed, each process comprising an aromatic C8 stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising a crystalline microporous solid of this invention.

The present invention further provides processes for oligomerizing olefins, each process comprising contacting an olefin feed under oligomerization conditions with a catalyst comprising a crystalline microporous solid of this invention.

This invention also provides processes for converting lower alcohols and other oxygenated hydrocarbons, each process comprising contacting said lower alcohol (for example, methanol, ethanol, or propanol) or other oxygenated hydrocarbon with a catalyst comprising a crystalline microporous solid of this invention under conditions to produce liquid products.

Also provided by the present invention are processes for reducing oxides of nitrogen contained in a gas stream in the presence of oxygen wherein each process comprises contacting the gas stream with a crystalline microporous solid of this invention. The a crystalline microporous solid may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

Also provided are processes for converting synthesis gas containing hydrogen and carbon monoxide, also referred to as syngas or synthesis gas, to liquid hydrocarbon fuels, using a catalyst comprising any of the germanosilicates described herein, including those having CIT-13 frameworks, and Fischer-Tropsch catalysts. Such catalysts are described in U.S. Pat. No. 9,278,344, which is incorporated by reference for its teaching of the catalysts and methods of using the catalysts. The Fischer-Tropsch component includes a transition metal component of groups 8-10 (i.e., Fe, Ru, Os, Co, Rh, IR, Ni, Pd, Pt), preferably cobalt, iron and/or ruthenium. The optimum amount of catalytically active metal present depends inter alia on the specific catalytically active metal. Typically, the amount of cobalt present in the catalyst may range from 1 to 100 parts by weight per 100 parts by weight of support material, preferably from 10 to 50 parts by weight per 100 parts by weight of support material. In one embodiment, from 15 to 45 wt % cobalt is deposited on the hybrid support as the Fischer-Tropsch component. In another embodiment from 20 to 45 wt % cobalt is deposited on the hybrid support. The catalytically active Fischer-Tropsch component may be present in the catalyst together with one or more metal promoters or co-catalysts. The promoters may be present as metals or as metal oxide, depending upon the particular promoter concerned. Suitable promoters include metals or oxides of transition metals, including lanthanides and/or the actinides or oxides of the lanthanides and/or the actinides. As an alternative or in addition to the metal oxide promoter, the catalyst may comprise a metal promoter selected from Groups 7 (Mn, Tc, Re) and/or Groups 8-10. In some embodiments, the Fischer-Tropsch component further comprises a cobalt reduction promoter selected from the group consisting of platinum, ruthenium, rhenium, silver and combinations thereof. The method employed to deposit the Fischer-Tropsch component on the hybrid support involves an impregnation technique using aqueous or non-aqueous solution containing a soluble cobalt salt and, if desired, a soluble promoter metal salt, e.g., platinum salt, in order to achieve the necessary metal loading and distribution required to provide a highly selective and active hybrid synthesis gas conversion catalyst.

Still further process embodiments include those for reducing halide concentration in an initial hydrocarbon product comprising undesirable levels of an organic halide, the process comprising contacting at least a portion of the hydrocarbon product with a composition comprising any of the germanosilicate structures described herein, including CIT-13, under organic halide absorption conditions to reduce the halogen concentration in the hydrocarbon. The initial hydrocarbon product may be made by a hydrocarbon conversion process using an ionic liquid catalyst comprising a halogen-containing acidic ionic liquid. In some embodiments, the organic halid content in the initial hydrocarbon product is in a range of from 50 to 4000 ppm; in other embodiments, the halogen concentrations are reduced to provide a product having less than 40 ppm. In other embodiments, the production may realize a reduction of 85%, 90%, 95%, 97%, or more. The initial hydrocarbon stream may comprise an alkylate or gasoline alkylate. Preferably the hydrocarbon alkylate or alkylate gasoline product is not degraded during the contacting. Any of the materials or process conditions described in U.S. Pat. No. 8,105,481 are considered to describe the range of materials and process conditions of the present invention. U.S. Pat. No. 8,105,481 is incorporated by reference at least for its teachings of the methods and materials used to effect such transformations (both alkylations and halogen reductions).

Still further process embodiments include those processes for increasing the octane of a hydrocarbon feedstock to produce a product having an increased aromatics content comprising contacting a hydrocarbonaceous feedstock which comprises normal and slightly branched hydrocarbons having a boiling range above about 40 C and less than about 200 C under aromatic conversion conditions with the catalyst.

Specific conditions for many of these transformations are known to those of ordinary skill in the art. Exemplary conditions for such reactions/transformations may also be found in WO/1999/008961, U.S. Pat. Nos. 4,544,538, 7,083, 714, 6,841,063, and 6,827,843, each of which are incorporated by reference herein in its entirety for at least these purposes.

Depending upon the type of reaction which is catalyzed, the microporous solid may be predominantly in the hydrogen form, partially acidic or substantially free of acidity. The skilled artisan would be able to define these conditions without undue effort. As used herein, "predominantly in the hydrogen form" means that, after calcination (which may also include exchange of the pre-calcined material with $NH_4^+$ prior to calcination), at least 80% of the cation sites are occupied by hydrogen ions and/or rare earth ions.

The germanosilicates of the present invention may also be used as adsorbents for gas separations. For example, these germanosilicate can also be used as hydrocarbon traps, for example, as a cold start hydrocarbon trap in combustion engine pollution control systems. In particular, such germanosilicate may be particularly useful for trapping $C_3$ fragments. Such embodiments may comprise processes and devices for trapping low molecular weight hydrocarbons from an incoming gas stream, the process comprising passing the gas stream across or through a composition comprising any one of the crystalline microporous germanosilicate compositions described herein, so as to provide an outgoing gas stream having a reduced concentration of low molecular weight hydrocarbons relative to the incoming gas stream. In this context, the term "low molecular weight hydrocarbons" refers to C1-C6 hydrocarbons or hydrocarbon fragments.

The germanosilicates of the present invention may also be used in a process for treating a cold-start engine exhaust gas stream containing hydrocarbons and other pollutants, wherein the process comprises or consist of flowing the engine exhaust gas stream over one of the germanosilicate compositions of the present invention which preferentially adsorbs the hydrocarbons over water to provide a first exhaust stream, and flowing the first exhaust gas stream over a catalyst to convert any residual hydrocarbons and other pollutants contained in the first exhaust gas stream to innocuous products and provide a treated exhaust stream and discharging the treated exhaust stream into the atmosphere.

The germanosilicates of the present invention can also be used to separate gases. For example, these can be used to separate water, carbon dioxide, and sulfur dioxide from fluid streams, such as low-grade natural gas streams, and carbon dioxide from natural gas. Typically, the molecular sieve is used as a component in a membrane that is used to separate the gases. Examples of such membranes are disclosed in U.S. Pat. No. 6,508,860.

For each of the preceding processes described, additional corresponding embodiments include those comprising a device or system comprising or containing the materials described for each process. For example, in the gas of the gas trapping, additional embodiments include those devices known in the art as hydrocarbon traps which may be positioned in the exhaust gas passage of a vehicle. In such devices, hydrocarbons are adsorbed on the trap and stored until the engine and exhaust reach a sufficient temperature for desorption. The devices may also comprise membranes comprising the germanosilicate compositions, useful in the processes described.

TERMS

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods or compositions/systems to provide the germanosilicate compositions at meaningful yields (or the ability of the systems using only those ingredients listed.

The term "meaningful product yields" is intended to reflect product yields such as described herein, but also including greater than 20%, but when specified, this term may also refer to yields of 10%, 20%, 30%, 40%, 50%, 60%, 70%, 80%, or 90% or more, relative to the amount of original substrate.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C," as separate embodiments, as well as $C_{1-3}$.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 6 carbon atoms, such as methyl, ethyl, n-propyl, isopropyl, n-butyl, isobutyl, tert-butyl, and the like.

The term "aromatic" refers to the ring moieties which satisfy the Hückel 4n+2 rule for aromaticity, and includes both aryl (i.e., carbocyclic) and heteroaryl structures.

The term "halide" is used in the conventional sense to refer to a chloride, bromide, fluoride, or iodide.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

The terms "oxygenated hydrocarbons" or "oxygenates" as known in the art of hydrocarbon processing to refer to components which include alcohols, aldehydes, carboxylic acids, ethers, and/or ketones which are known to be present in hydrocarbon streams or derived from biomass streams other sources (e.g. ethanol from fermenting sugar).

The terms "separating" or "separated" carry their ordinary meaning as would be understood by the skilled artisan, insofar as they connote physically partitioning or isolating solid product materials from other starting materials or co-products or side-products (impurities) associated with the reaction conditions yielding the material. As such, it infers that the skilled artisan at least recognizes the existence of the product and takes specific action to separate or isolate it from starting materials and/or side- or byproducts. Absolute purity is not required, though it is preferred. In the case where the terms are used in the context of gas processing, the terms "separating" or "separated" connote a partitioning of the gases by adsorption or by permeation based on size or physical or chemical properties, as would be understood by those skilled in the art.

Unless otherwise indicated, the term "isolated" means physically separated from the other components so as to be free of at least solvents or other impurities, such as starting materials, co-products, or byproducts. In some embodiments, the isolated crystalline materials, for example, may be considered isolated when separated from the reaction mixture giving rise to their preparation, from mixed phase co-products, or both. In some of these embodiments, pure germanosilicates (including structures with or without incorporated OSDAs) can be made directly from the described methods. In some cases, it may not be possible to separate crystalline phases from one another, in which case, the term "isolated" can refer to separation from their source compositions.

The term "microporous," according to IUPAC notation refers to a material having pore diameters of less than 2 nm. Similarly, the term "macroporous" refers to materials having pore diameters of greater than 50 nm. And the term "mesoporous" refers to materials whose pore sizes are intermediate between microporous and macroporous. Within the context of the present disclosure, the material properties and applications depend on the properties of the framework such as pore size and dimensionality, cage dimensions and material composition. Due to this there is often only a single framework and composition that gives optimal performance in a desired application.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "method(s)" and "process(es)" are considered interchangeable within this disclosure.

As used herein, the term "crystalline microporous solids" or "crystalline microporous germanosilicate" are crystalline structures having very regular pore structures of molecular dimensions, i.e., under 2 nm. The maximum size of the species that can enter the pores of a crystalline microporous solid is controlled by the dimensions of the channels. These terms may also refer specifically to CIT-13 compositions.

The term "silicate" refers to any composition including silicate (or silicon oxide) within its framework. It is a general term encompassing, for example, pure-silica (i.e., absent other detectable metal oxides within the framework), aluminosilicate, borosilicate, ferrosilicate, germanosilicate, stannosilicate, titanosilicate, or zincosilicate structures. The term "germanosilicate" refers to any composition including silicon and germanium oxides within its framework. Such germanosilicate may be "pure-germanosilicate (i.e., absent other detectable metal oxides within the framework) or optionally substituted. When described as "optionally substituted," the respective framework may contain aluminum, boron, gallium, germanium, hafnium, iron, tin, titanium, indium, vanadium, zinc, zirconium, or other atoms substituted for one or more of the atoms not already contained in the parent framework.

The following listing of Embodiments is intended to complement, rather than displace or supersede, the previous descriptions.

Embodiment 1

A crystalline microporous germanosilicate composition comprising a three dimensional framework having pores defined by 10- and 14-membered rings. As should be apparent from the descriptions herein, these 10- and 14-membered rings comprise silicon-oxygen and germanium-oxygen linkages and that 10- and 14-membered refer to the number of oxygen atoms in the respective rings.

Embodiment 2

A crystalline microporous germanosilicate composition, which exhibits at least one of:

(a) a powder X-ray diffraction (XRD) pattern exhibiting at least five of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ;

(b) a powder X-ray powder diffraction (XRD) pattern substantially the same as shown in FIG. 1(B) or 1(C); or (c) unit cell parameters substantially equal to the following:

| Space group | Cmmm |
|---|---|
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1) |

Embodiment 3

The crystalline microporous germanosilicate composition of Embodiment 1 or 2, which exhibits a powder X-ray diffraction (XRD) pattern exhibiting at least five of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ. In separate Aspects of this Embodiment, the composition exhibits six, seven, eight, nine, or ten of the characteristic peaks. In other Aspects of this Embodiment, the composition contains 5, 6, 7, 8, 9, 10, or more of the peaks identified in Table 3.

Embodiment 4

The crystalline microporous germanosilicate composition of any one of Embodiments 1 to 3 which exhibits a powder X-ray diffraction (XRD) pattern substantially the same as shown in FIG. 1(A), 1(B), or 1(C).

Embodiment 5

The crystalline microporous germanosilicate composition of any one of Embodiments 1 to 4 which exhibits unit cell parameters substantially equal to the following at:

| Space group | Cmmm |
|---|---|
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1) |

Embodiment 6

The crystalline microporous germanosilicate composition of Embodiment 2, exhibiting at least two of (a), (b), or (c).

Embodiment 7

The crystalline microporous germanosilicate composition of any one of Embodiments 1 to 6, wherein the channel dimensions of the 10- and 14-membered rings are 6.2×4.5 Å and 9.1×7.2 Å, respectively.

Embodiment 8

The crystalline microporous germanosilicate composition of any one of Embodiments 1 to 7, having a ratio of Si:Ge atoms in a range of from 2:1 to 16:1.

Embodiment 9

The crystalline microporous germanosilicate composition of any one of claims 1 to 8, that is substantially free of an organic structure-directing agent (OSDA)

Embodiment 10

The crystalline microporous germanosilicate composition of any one of Embodiments 1 to 8, further comprising at least one substituted benzyl-imidazolium organic structure-directing agent (OSDA).

Embodiment 11

The crystalline microporous germanosilicate composition of Embodiment 10, wherein the at least one substituted benzyl-imidazolium organic structure-directing agent has a structure:

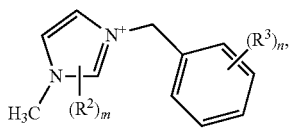

but not

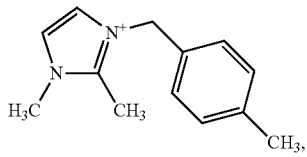

wherein m and n are independently 1, 2, or 3, and $R^1$, $R^2$, and $R^3$ are independently at each occurrence $C_{1-3}$ alkyl.

Embodiment 12

The crystalline microporous germanosilicate composition of Embodiment 11, wherein the at least one substituted benzyl-imidazolium organic structure-directing agent has a structure:

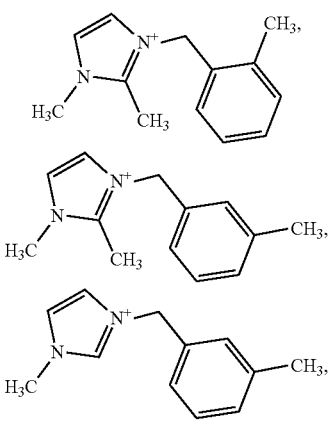

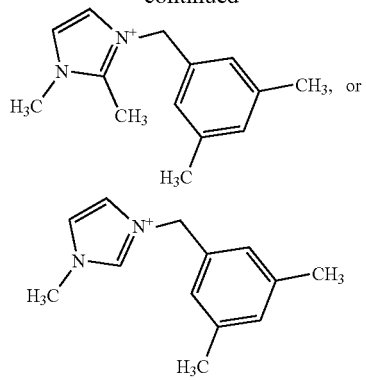

Embodiment 13

An aqueous composition comprising:
(a) a source of silicon oxide
(b) a source of germanium oxide;
(c) a mineralizing agent;
(d) at least one substituted benzyl-imidazolium organic structure-directing agent (OSDA) having a structure:

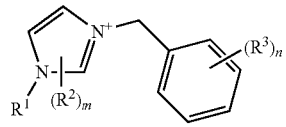

but not

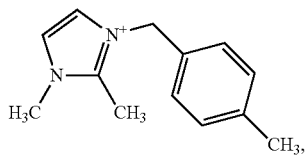

wherein m and n are independently 1, 2, or 3, and $R^1$, $R^2$, and $R^3$ are independently at each occurrence C1-3 alkyl; and
(e) a crystalline microporous germanosilicate composition of any one of Embodiments 1 to 12.

Embodiment 14

The aqueous composition of Embodiment 13, wherein:
(a) the source of silicon oxide comprises tetraethyl orthosilicate (TEOS); or
(b) the source of germanium oxide comprises $GeO_2$, or a hydrated derivative thereof; or
(c) both (a) and (b).

Embodiment 15

The aqueous composition of Embodiment 13 or 14, wherein the mineralizing agent comprises:
(a) a fluoride source comprising hydrofluoric acid, or a salt or derivative thereof;
(b) an alkali metal hydroxide or alkaline earth metal hydroxide, or combination thereof.

Embodiment 16

The aqueous composition of any one of Embodiments 13 to 15, wherein the at least one substituted benzyl-imidazolium organic structure-directing agent has a structure:

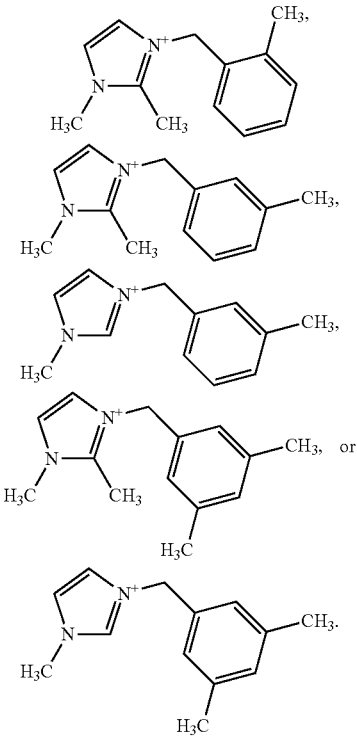

Embodiment 17

The aqueous composition of any one of Embodiments 13 to 16, wherein the crystalline microporous germanosilicate has occluded within its pores at least one of the substituted benzyl-imidazolium organic structure-directing agents. In other Aspects of this Embodiment, the crystalline microporous germanosilicate is substantially free of any organic structuring agent.

Embodiment 18

The aqueous composition of any one of Embodiments 13 to 17, wherein the composition is a suspension or a gel.

Embodiment 19

A method comprising hydrothermally treating an aqueous composition comprising:
(a) a source of silicon oxide
(b) a source of germanium oxide;
(c) a mineralizing agent;
(d) at least one substituted benzyl-imidazolium organic structure-directing agent (OSDA) having a structure:

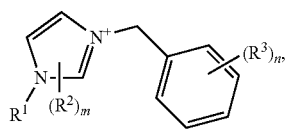

but not

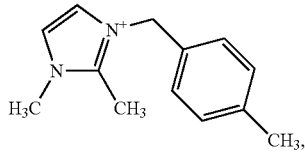

wherein m and n are independently 1, 2, or 3, and $R^1$, $R^2$, and $R^3$ are independently at each occurrence C1-3 alkyl, under conditions effective to crystallize a crystalline microporous germanosilicate composition of any one of Embodiments 1 to 8.

Embodiment 20

The method of Embodiment 19, wherein:
(a) the source of silicon oxide comprises tetraethyl orthosilicate (TEOS), or any of the sources of silicon oxide otherwise cited herein; or
(b) the source of germanium oxide comprises $GeO_2$, or a hydrated derivative thereof or
(c) both (a) and (b).

Embodiment 21

The method of Embodiment 19 or 20, wherein the source of silicon oxide and the source of germanium oxide are present in a molar ratio in a range of from about 2:1 to about 8:1.

Embodiment 22

The method of any one of Embodiments 19 to 21, wherein the mineralizing agent comprises:
(a) a fluoride source comprising hydrofluoric acid, or a salt or derivative thereof or
(b) a source of hydroxide; or
(c) both a source of fluoride and hydroxide.

Embodiment 23

The method of any one of Embodiments 19 to 22, wherein the mineralizing agent comprises hydrofluoric acid or ammonium fluoride.

Embodiment 24

The method of any one of Embodiments 19 to 22, wherein the mineralizing agent comprises an alkali metal hydroxide or alkaline earth metal hydroxide, or combination thereof.

Embodiment 25

The method of any one of Embodiments 19 to 24, wherein the at least one substituted benzyl-imidazolium organic structure-directing agent has a structure:

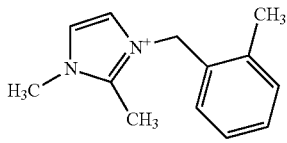

-continued

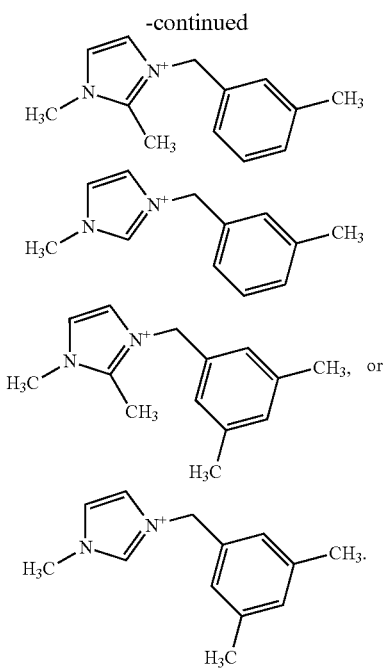

Embodiment 26

The method of any one of Embodiments 19 to 25, wherein the crystalline microporous germanosilicate has occluded within its pores at least one of the substituted benzyl-imidazolium organic structure-directing agents.

Embodiment 27

The method of any one of Embodiments 19 to 25, wherein the crystalline microporous germanosilicate is substantially free of occluded substituted benzyl-imidazolium organic structure-directing agents.

Embodiment 28

The method of any one of Embodiments 19 to 27, wherein the composition is a suspension or a gel.

Embodiment 29

The method of any one of claims 19 to 28, wherein effective crystallization conditions include a temperature of from about 140° C. to about 180° C., and a time of from about 4 days to about 4-6 weeks.

Embodiment 30

The method of any one of Embodiments 19 to 29, further comprising isolating a product crystalline microporous germanosilicate solid which exhibits of at least one of the characteristics described for any one of Embodiments 1 to 8.

Embodiment 31

The method of Embodiment 30, further comprising:
(a) heating the isolated product crystalline microporous germanosilicate solid at a temperature in a range of from about 250° C. to about 450° C.; or
(b) contacting the isolated product crystalline microporous germanosilicate solid with ozone or other oxidizing agent at a temperature in a range of 25° C. to 200° C.; for a time sufficient to form a dehydrated or an OSDA-depleted product.

Embodiment 32

The method of Embodiment 31, further comprising:
(a) treating the dehydrated or OSDA-depleted product with an aqueous alkali, alkaline earth, transition metal, rare earth metal, ammonium or alkylammonium salt; and/or
(b) treating the dehydrated or OSDA-depleted product with at least one type of transition metal or transition metal oxide.

Embodiment 33

The method of any one of Embodiments 30 to 32, further comprising calcining the isolated crystalline microporous solid in air a temperature in a range of from about 500° C. to about 1200° C.

Embodiment 34

A crystalline microporous germanosilicate composition prepared according to a method of any one of Embodiments 19 to 33.

Embodiment 35

A process for affecting an organic transformation, the process comprising:
(a) carbonylating DME with CO at low temperatures;
(b) reducing NOx with methane:
(c) cracking, hydrocracking, or dehydrogenating a hydrocarbon;
(d) dewaxing a hydrocarbon feedstock;
(d) converting paraffins to aromatics:
(e) isomerizing or disproportionating an aromatic feedstock;
(f) alkylating an aromatic hydrocarbon;
(g) oligomerizing an alkene;
(h) aminating a lower alcohol;
(i) separating and sorbing a lower alkane from a hydrocarbon feedstock;
(j) isomerizing an olefin;
(k) producing a higher molecular weight hydrocarbon from lower molecular weight hydrocarbon;
(l) reforming a hydrocarbon
(m) converting a lower alcohol or other oxygenated hydrocarbon to produce an olefin products (including MTO);
(n) epoxiding olefins with hydrogen peroxide;
(o) reducing the content of an oxide of nitrogen contained in a gas stream in the presence of oxygen;
(p) separating nitrogen from a nitrogen-containing gas mixture;
(q) converting synthesis gas containing hydrogen and carbon monoxide to a hydrocarbon stream; or
(r) reducing the concentration of an organic halide in an initial hydrocarbon product; by contacting the respective feedstock with the a catalyst comprising the crystalline microporous solid of any one of claims 1 to 9 or 34 or prepared according to a method of any one of claims 19 to 33, under conditions sufficient to affect the named transformation.

Embodiment 36

The process of Embodiment 36 comprising:
(c) cracking, hydrocracking, or dehydrogenating a hydrocarbon;
(d) dewaxing a hydrocarbon feedstock;
(d) converting paraffins to aromatics:
(e) isomerizing or disproportionating an aromatic feedstock;
(f) alkylating an aromatic hydrocarbon;
(g) oligomerizing an alkene;
(i) separating and sorbing a lower alkane from a hydrocarbon feedstock;
(j) isomerizing an olefin;
(k) producing a higher molecular weight hydrocarbon from lower molecular weight hydrocarbon; or
(l) reforming a hydrocarbon.

Embodiment 37

The process of Embodiment 35 comprising converting synthesis gas containing hydrogen and carbon monoxide to a hydrocarbon stream using a catalyst comprising the crystalline microporous germanosilicate composition and a Fischer-Tropsch catalyst (see U.S. Pat. No. 9,278,344).

Embodiment 38

The process of Embodiment 35 comprising reducing the concentration of an organic halide in an initial hydrocarbon product, the initial hydrocarbon product containing an undesirable level of the organic halide, the process comprising contacting at least a portion of the initial hydrocarbon product with a composition comprising the crystalline microporous germanosilicate composition, under organic halide absorption conditions to reduce the halogen concentration in the hydrocarbon. (see U.S. Pat. No. 8,105,481).

Embodiment 39

A process of trapping low molecular weight hydrocarbons from an incoming gas stream comprising passing the gas stream across or through a composition comprising the crystalline microporous germanosilicate composition of any one of claim 1 to 9 or 34 or prepared according to a method of any one of claims 19 to 33, so as to provide an outgoing gas stream having a reduced concentration of low molecular weight hydrocarbons relative to the incoming gas stream.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: Materials and Methods

Unless otherwise noted, all reagents were purchased from commercial sources and were used as received. Unless otherwise noted all, reactions were conducted in flame-dried glassware under an atmosphere of argon. Hydroxide ion exchanges were performed using OH-form styrene-divinylbenzene (DVB)-matrix ion exchange resin (DOWEX™ MARATHON™ A) with an exchange capacity of 1 meq/mL. Titrations were performed using a Mettler-Toledo DL22 autotitrator using 0.01 M HCl as the titrant. All liquid NMR spectra were recorded with a 500 MHz Varian Spectrometer. Liquid NMR spectra were recorded on Varian Mercury spectrometers.

All powder x-ray diffraction characterization were conducted on a Rigaku MiniFlex II diffractometer with Cu Kα radiation.

Solid-state NMR ($^{13}$C and $^{29}$Si) spectra were obtained using a Bruker DSX-500 spectrometer (11.7 T) and a Bruker 4 mm MAS probe. The spectral operating frequencies were 500 MHz, 125.7 MHz, and 99.4 MHz for $^1$H, $^{13}$C, and $^{29}$Si nuclei, respectively. Spectra were referenced to external standards as follows: tetramethylsilane (TMS) for $^1$H and $^{29}$Si and adamantane for $^{13}$C as a secondary external standard relative to tetramethylsilane. Samples were spun at 14 kHz for $^1$H NMR and 8 kHz for $^{13}$C and $^{29}$Si MAS and CPMAS NMR experiments.

Thermogravimetric analysis (TGA) was performed on a Perkin Elmer STA 6000 with a ramp of 10° C.min$^{-1}$ to 900° C. under air atmosphere. Samples (0.01-0.06 g) were placed in aluminum crucible and heated at 1 K/min in a flowing stream (0.667 cm$^3$/s) comprised of 50% air (Air Liquide, breathing grade) and 50% argon (Air Liquide, UHP).

SEM analyses were performed on a ZEISS 1550 VP FESEM, equipped with an Oxford X-Max SDD X-ray Energy Dispersive Spectrometer (EDS) system for determining the Si/Al ratios of the samples.

Example 2. Synthesis of the Organic Structuring Agents

A series of six monoquatemary ("monoquat") and three diquaternary ("diquat") organic structure-directing agents (OSDAs) were studied. These six monoquats and three diquats, along with their numerical designations, can be found in Tables 1A, 1B, and 1C:

TABLE 1A

Monoquat benzyl-imidazolium cations studied in this work

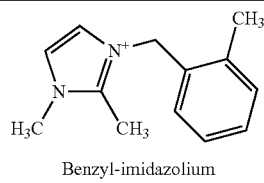

(1)

Benzyl-imidazolium

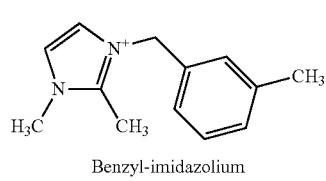

(2)

Benzyl-imidazolium

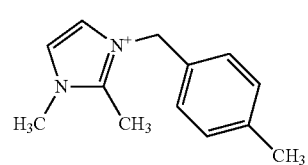

(3)

Benzyl-imidazolium

TABLE 1B

Monoquat benzyl-imidazolium cations studied in this work

Benzyl-imidazolium (4)

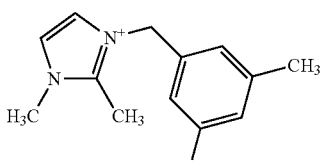

Benzyl-imidazolium (5)

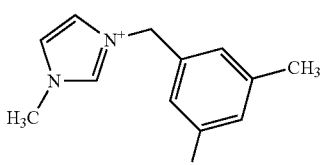

Benzyl-imidazolium (6)

TABLE 1C

Diquat benzyl-diimidazolium dications studied in this work

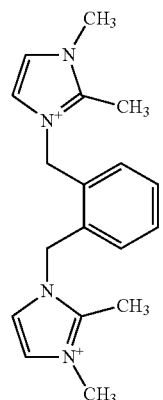

Benzyl-diimidazolium (7)

TABLE 1C-continued

Diquat benzyl-diimidazolium dications studied in this work

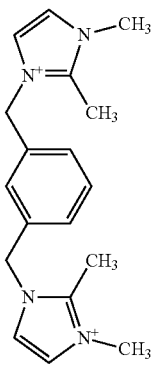

Benzyl-diimidazolium (8)

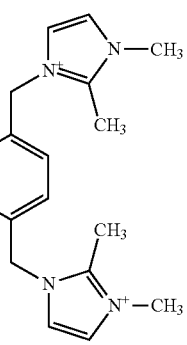

Benzyl-diimidazolium (9)

These were prepared as follows. Unless stated otherwise, reactions were conducted in flame-dried glassware under an atmosphere of argon.

Example 2.1. Preparation of 1,2-Dimethyl-3-(2-methyl-benzyl)imidazol-1-ium chloride ("Benzyl-imidazolium (1)" or "OSDA 1")

A 500 mL flask was charged with 1,2-dimethylimidazole (7.73 grams, 55.0 mmols), 2-methylbenzyl chloride (7.73 grams, 60.5 mmols) and toluene(100 mL). The flask was fitted with a reflux condenser and heated to reflux for 15 hours. Reaction was cooled to 25° C. and resulting solids were filtered and washed with ethyl acetate (3×20 mL) to give a white solid (11.84 grams, 91% yield). $^1$H NMR (500 MHz, CD$_3$OD): δ 7.37-7.33 (m, 2H), 7.31 (d, J=5.0 Hz, 1H), 7.30-7.26 (m, 1H), 7.02 (d, J=5.0 Hz, 1H) 5.45 (s, 2H), 3.92 (s, 3H), 2.67 (s, 3H), 2.38 (s, 3H). $^{13}$C NMR (126 MHz, CD$_3$OD) δ 145.08, 136.40, 131.36, 130.69, 128.81, 127.56, 126.47, 122.44, 120.88, 49.59, 34.15, 17.66, 8.35.

Example 2.2. Preparation of 1,2-Dimethyl-3-(3-methyl-benzyl)imidazol-1-ium chloride ("Benzyl-imidazolium (2)" or "OSDA 2")

This OSDA was prepared as in Example 2.1, except that 3-methylbenzyl chloride was used instead of 2-methylbenzyl chloride. The reaction yielded a beige solid (22.65 grams, 87% yield). $^1$H NMR (500 MHz, CD$_3$OD): δ 7.55 (s, 2H), 7.34 (dd, J=10.0, 5.0, 1H), 7.25 (d, J=10.0, 1H), 7.20 (s, 1H), 7.14 (d, J=5.0, 1H), 5.40 (s, 2H), 3.88 (s, 3H), 2.67

(s, 3H), 2.39 (s, 3H). $^{13}$C NMR (125.7 MHz, CD$_3$OD) δ 144.8, 139.1, 133.7, 129.3, 128.9, 128.1, 124.6, 122.4, 121.2, 51.3, 34.1, 19.9, 8.4.

Example 2.3. Preparation of 1,2-Dimethyl-3-(3-methylbenzyl)imidazolium hydroxide ("Benzyl-imidazolium (2)" or "OSDA 2")

This OSDA was prepared according to the method of Example 2.2, except that the obtained chloride salt was repeatedly washed with 4 L of diethyl ether and dried under vacuum for 12 hours. The chloride anions were exchanged with hydroxyl anions using OH-form styrene-divinylbenzene (DVB)-matrix ion exchange resin (DOWEX™ MARATHON™ A). $^1$H NMR (500 MHz, CDCl$_3$): δ 7.79 (d, 1H), 7.58 (d, 1H), 7.29 (m, 1H), 7.19 (m, 1H), 7.11 (m, 1H), 7.10 (m, 1H), 5.49 (s, 2H), 4.03 (s, 3H), 2.81 (s, 3H), 2.37 (s, 3H). $^{13}$C NMR (125.7 MHz, CDCl$_3$): δ 144.29, 139.37, 132.79, 129.92, 129.29, 128.60, 125.10, 122.96, 121.73, 52.46, 35.90, 21.36, 10.90.

Example 2.4. Preparation of 1,2-Dimethyl-3-(4-methyl-benzyl) imidazol-1-ium hydroxide ("Benzyl-imidazolium (3)" or "OSDA 3")

This OSDA was prepared according to the method of Example 2.1, except that 4-methylbenzyl chloride was used instead of 2-methylbenzyl chloride. The reaction yielded a white solid (24.10 grams, 92% yield). The chloride anions were exchanged with hydroxyl anions using OH-form styrene-divinylbenzene (DVB)-matrix ion exchange resin (DOWEX™ MARATHON™ A). $^1$H NMR (500 MHz, CD$_3$OD): δ 7.54-7.53 (m, 2H), 7.28 (d, J=5.0, 2H), 7.28 (d, J=5.0, 2H), 5.34 (s, 2H), 3.87 (s, 3H), 2.67 (s, 3H), 2.39 (s, 3H). $^{13}$C NMR (125.7 MHz, CD$_3$OD) δ 144.8, 138.8, 130.7, 129.5, 127.6, 122.4, 121.1, 51.2, 34.1, 19.7, 8.4.

Example 2.5. Preparation of 1-methyl-3-(3-methyl-benzyl)imidazolium hydroxide ("Benzyl-imidazolium (4)" or "OSDA 4")

1-Methylimidazole (14.4 g, 150 mmol) was dissolved in 300 ml of toluene and heated up to 45° C. While vigorously stirring, 3-methylbenzyl chloride (21.1 g, 150 mmol) was added dropwise. After 30 min of additional stirring, the temperature was increased to 105° C. and the reaction proceeded for 24 hours. After that, the reaction mixture was cooled in a dry ice bath since this imidazolium salt exists as a liquid salt at the room temperature in its chloride form. A cold filtration was performed to isolate the product in solid form. The obtained chloride salt was repeatedly washed with 4 L of cold diethyl ether and dried under vacuum for 12 hours. The chloride anions were exchanged with hydroxyl anions using OH-form styrene-divinylbenzene (DVB)-matrix ion exchange resin (DOWEX™ MARATHON™ A). $^1$H NMR (500 MHz, CDCl$_3$): δ 10.54 (s, 1H), 7.64 (t, 1H), 7.32 (m, 1H), 7.14 (m, 3H), 7.05 (m, 1H), 5.42 (s, 2H), 3.97 (s, 3H), 2.22 (s, 3H). $^{13}$C NMR (125.7 MHz, CDCl$_3$): δ 139.14, 137.42, 133.02, 130.04, 129.28, 129.12, 125.77, 123.92, 121.78, 53.07, 36.46, 21.21.

Example 2.6. Preparation of 1,2-Dimethyl-3-(3,5-dimethylbenzyl)imidazolium hydroxide ("Benzyl-imidazolium (5)" or "OSDA 5")

1,2-Dimethylimidazole (12.3 g, 150 mmol) was dissolved in 300 ml of toluene in an ice bath. While vigorously stirring, 3,5-dimethylbenzyl bromide (29.9 g, 150 mmol) was added. After 30 min of additional stirring, the temperature was slowly increased to 105° C. and the reaction proceeded for 15 hours, after which the reaction mixture was cooled and filtered. The obtained chloride salt was repeatedly washed with 4 L of diethyl ether and dried under vacuum for 12 hours. The chloride anions were exchanged with hydroxyl anions using OH-form ion exchange resin. $^1$H NMR (500 MHz, CDCl$_3$): δ 7.77 (d, 1H), 7.49 (d, 1H), 6.99 (m, 1H), 6.89 (m, 2H), 5.41 (s, 2H), 4.03 (s, 3H), 3.19 (s, 3H), 2.31 (s, 6H). $^{13}$C NMR (125.7 MHz, CDCl$_3$): δ 144.29, 139.19, 132.55, 130.81, 125.71, 122.92, 121.61, 52.57, 36.19, 21.23, 11.38.

Example 2.7. Preparation of 1-Methyl-3-(3,5-dimethylbenzyl)imidazolium hydroxide ("Benzyl-imidazolium (6)" or "OSDA 6")

This OSDA was prepared according to the method of Example 2.6 using 1-methylimidazole and 3,5-dimethylbenzyl bromide. The obtained chloride salt was repeatedly washed with 4 L of diethyl ether and dried under vacuum for 12 hours. The chloride anions were exchanged with hydroxyl anions using OH-form ion exchange resin. $^1$H NMR (500 MHz, CDCl$_3$): δ 10.46 (td, 1H), 7.53 (t, 1H), 7.27 (d, 1H), 7.00 (dm, 3H), 5.44 (s, 2H), 4.09 (s, 3H), 2.28 (s, 6H). $^{13}$C NMR (125.7 MHz, CDCl$_3$): δ 139.23, 137.34, 132.55, 131.17, 126.59, 123.65, 121.71, 53.44, 36.78, 21.18.

Example 2.8. Preparation of ("Benzyl-diimidazolium (7)" or "OSDA 7")

A 500 mL flask was charged with 1,2-dimethyl imidazole (16.0 g, 166.7 mmol), α,α'-dichloro-o-xylene (20.0 g, 75.8 mmol) and ethanol (300 mL). The flask was fitted with a reflux condenser and heated to reflux for 15 h. The reaction was cooled to 0° C. and resulting solids were filtered and washed with ethyl acetate (3×50 mL) to give (27.10 g, 78% yield) a white solid. $^1$H NMR (500 MHz, CD$_3$OD): δ 7.58 (d, J=2.0, 2H), 7.45 (dd, J=3.5, 2.5 2H), 7.43 (d, J=2.0, 2H), 7.02 (dd, J=3.5, 2.5 2H), 5.64 (s, 4H), 3.91 (s, 6H), 2.68 (s, 6H). $^{13}$C NMR (126 MHz, CD$_3$OD): 147.04, 133.03, 130.76, 129.02, 124.21, 122.49, 50.19, 35.86, 10.36.

Example 2.9. Preparation of ("Benzyl-diimidazolium (8)" or "OSDA 8")

The reaction was carried out as in Example 2.8, except the α,α dibromo-m-xylene was used (82% yield). $^1$H NMR (500 MHz, CD$_3$OD) 7.53-7.47 (m, 5H), 7.44-7.42 (m, 1H), 7.35-7.33 (m, 2H), 5.45 (s, 4H), 3.86 (s, 6H), 2.65 (s, 6H). $^{13}$C NMR (126 MHz): 145.05, 135.08, 129.94, 127.95, 127.29, 122.57, 121.13, 50.82, 34.27, 8.70.

Example 2.10. Preparation of ("Benzyl-diimidazolium (9)" or "OSDA 9")

This time the reaction as in Example 2.8, but using α,α dichloro-p-xylene. The product had a yield of 78%. $^1$H NMR (500 MHz, CD$_3$OD) 7.52 (d, J=2.5, 2H), 7.51 (d, J=2.5 2H), 7.40 (s, 4H), 5.43 (s, 4H), 3.84 (s, 6H), 2.63 (s, 6H). $^{13}$C NMR (126 MHz, CD$_3$OD): 146.44, 136.05, 129.88, 123.98, 122.56, 52.16, 35.62, 9.94.

Example 3. Syntheses of Crystalline Materials

All reactions were performed in 23 mL Teflon-lined stainless steel autoclaves (Parr instruments). Reactions were performed either statically or tumbled at approximately 40 rpm using spits built into convection ovens. Silicon source was tetraethyl orthosilicate (99.9% Si(OCH$_2$CH$_3$)$_4$, Strem). Germanium source was germanium oxide (99.99% GeO$_2$, Strem).

Gels for germanosilicate reactions were prepared by adding germanium oxide to a solution of the organic structure-directing agent in water directly into the 23 mL Teflon liner. This mixture is stirred at 25° C. for 5 minutes, or until germanium oxide has dissolved into the solution. Tetraethyl orthosilicate was then added, reaction vessel is capped, and stirred for an additional 12 hours to hydrolyze the tetraethyl orthosilicate. The reaction vessel was then uncapped and a stream of air was blown over the gel, while it was mechanically stirred, until the required excess of water and hydrolyzed ethanol has been evaporated. In certain cases, the gel was put under vacuum to remove small amounts of residual water, when evaporation failed to remove the required amount of water. Hydrofluoric acid was then added in a dropwise fashion to the gel and the Teflon liner was sealed into the stainless steel autoclave and put into the oven. The reactors were opened every 6-7 days to assess reaction progress. After homogenizing, a small sample was successfully washed with deionized H$_2$O (2×10 mL) and acetone: methanol (1:1, 3×10 mL) and the XRD pattern was inspected. All reactions were monitored for at least 1 month.

The variable ratios used for the reactions were 1.0 SiO$_2$/xGeO$_2$ where x=0.50 and lower/0.50 OSDA as OH–/0.50 HF/5 H$_2$O. In the products there is a slight enrichment of Si/Ge over the starting ratio and in the CIT-13 product where reaction Si/Ge=4, the product has a value closer to 5 (by EDX measurements).

Example 3.1. Synthesis of Germanosilicate CIT-13 in Fluoride Media

The protocol for the synthesis of the germanosilicate microporous crystals has been previously reported. In this work, the gel composition was x/(x+1) SiO$_2$: 1/(x+1) GeO$_2$: 0.5-0.75 (OSDA)+OH–:0.5-0.75 HF: 5-15 H$_2$O where x is the Si/Ge molar ratio of the gel. A desired amount of germanium (IV) oxide (GeO$_2$) was dissolved in a desired amount of OSDA aqueous solution and tetraethyl orthosilicate (TEOS) in a 23 ml PTFE liner (Parr Instrument). The mixture was stirred for 12 hours in order to hydrolyze all TEOS, and dried under a continuous air flow to evaporate excess water and ethanol until the gel became very viscous. The equivalent amount of concentrated hydrofluoric acid (HF, 48 wt %) was added dropwise and thoroughly mixed using a PTFE spatula. After the HF mixing, the mixture became powdery. After an additional 2 days of drying, a desired amount of distilled water was added and mixed thoroughly. The PTFE liner containing the mixture was firmly clad with a Parr still reactor and put in a static convection oven. The crystallization temperature was typically 160° C., but other temperature in a range from 140° C. to 175° C. could be chosen. The crystallization had been monitored for at least 1 month. The resultant CIT-13 crystal was carefully washed with distilled water, methanol and acetone, and dried in a 70° C. convection oven before being characterized.

Example 3.2. Synthesis of Germanosilicate CIT-13 Using Ammonium Fluoride (NH$_4$F)

The gel composition for the NH$_4$F-protocol was the same as the HF-protocol described above, except for the fact that a molar-equivalent amount of NH$_4$F was used instead of HF. Desired amounts of GeO$_2$ and NH$_4$F were dissolved in OSDA aqueous solution and TEOS in a 23 ml PTFE liner. The mixture was stirred for 12 hours in order to hydrolyze all TEOS, and dried under a continuous air flow to evaporate excess water, ammonia and ethanol until the gel became completely powdery. And then, water was added to a desired level. The PTFE liner containing the mixture was firmly clad with a Parr still reactor and put in a static convection oven at 160° C. The rest of the protocol is the same as above.

Example 3.3. Synthesis of Germanosilicate IM-12 (UTL) in Hydroxide Media

The germanosilicate IM-12 of the UTL framework was synthesized to make a direct comparison with CIT-13. A spiro-quaternary ammonium, (6R,10S)-6,10-dimethyl-5-azaspiro[4.5]decanium hydroxide, was used as the OSDA for the synthesis of IM-12. This OSDA was prepared according to the protocol reported by Paillaud et al and other researching groups. The IM-12 germanosilicate was solvothermally synthesized using a hydroxy (OH–)-medium. The gel composition used in this work was 0.667 SiO$_2$:0.333 GeO$_2$:0.25 (OSDA)+OH–:30 H$_2$O. The gel mixture was prepared by dispersing desired amounts of silica (Cab-o-Sil®) and GeO2 in (OSDA$^+$)OH$^-$ solution and, the water content was adjusted by simply adding an equivalent amount of distilled water. The crystallization was performed at 175° C. for 14 day in a 23 ml Parr reactor. The rinsing step of the prepared IM-12 crystal was the same as the procedures for CIT-13 described above.

[from P-1] Example 3.4. Screening Reactions Using Monoquat Benzyl-Imidazolium Cations (1), (2), and (3)

These monoquats were studied in germanosilicate, fluoride-mediated reactions, with the composition of: (1-x) Si:x Ge:0.5 HF:0.5 ROH:5.0 H$_2$O with all reactions being performed statically at 160° C. Results of the syntheses are given in Table 2.

TABLE 2

Synthesis results using benzyl-imidazolium cations (1), (2), and (3)

| OSDA | Si/Ge = 2 | Si/Ge = 4 | Si/Ge = 8 | Si/Ge = 16 |
|---|---|---|---|---|
| 1 | IWS | CIT-13 | LTA/Amorphous | Amorphous |
| 2 | CIT-13 | CIT-13 | CIT-13 | CIT-13 |
| 3 | BEC/LTA | BEC/LTA | LTA | LTA |

Table 2 shows the products obtained with these three monoquats. The product denoted CIT-13 was obtained at a range of Si/Ge ratios and with OSDA 1 and 2. A representative powder XRD pattern of both the as-made and calcined material is shown in FIGS. 1(A-C). This powder pattern has not been known before and represents a new material, designated herein as CIT-13. It could be produced reproducibly and does not match any known material (search done using Jade database). In the as-made materials there was some variably in peak intensities between materials. This is commonly found in as-made materials and is attributed to the influence of the organic and OSDA. There were also impurity phases commonly encountered in these syntheses, so once a pure-phase material was found seeding was used in all subsequent syntheses.

The characteristic 2-theta peaks for the CIT-13 material are provided in Table 3.

TABLE 3

Powder XRD peaks for CIT-13; estimated variances in 2-θ are ±0.2°. Actual intensities often vary from theoretical values

| No. | 2-θ, deg | Theoretical Intensity | Comment |
|---|---|---|---|
| 1 | 6.45 | 100 | Very strong (200) peak, from interlayer spacing |
| 2 | 7.18 | 96.06 | Very strong (110) |
| 3 | 8.56 | 13.98 | Almost invisible in practice |
| 4 | 10.73 | 9.51 | Almost invisible in practice |
| 5 | 11.18 | 15.42 | Almost invisible in practice |
| 6 | 12.85 | 4.84 | Generally 5-10 times stronger than theoretical |
| 7 | 18.26 | 18.20 | Indistinguishable in practice |
| 8 | 18.36 | 11.11 | |
| 9 | 18.63 | 12.78 | — |
| 10 | 19.60 | 4.30 | — |
| 11 | 20.78 | 16.13 | — |
| 12 | 21.55 | 9.61 | — |
| 13 | 23.36 | 9.34 | — |
| 14 | 24.55 | 8.37 | — |
| 15 | 25.7 | 4.53 | — |
| 16 | 25.30 | 4.47 | — |
| 17 | 25.87 | 3.58 | — |
| 18 | 26.01 | 4.93 | Generally 5-10 times stronger than theoretical |
| 19 | 26.68 | 14.48 | — |
| 20 | 33.99 | 3.74 | — |

Example 3.5. Screening Reactions Using Monoquat Benzyl-Imidazolium Cations (2), (4), (5), and (6)

An expanded set of experiments are described in Table 4.

TABLE 4

Summary of synthesis conditions tested in this study. All ratios are in molar ratios. All reactions at 160° C.

| OSDA | Si/Ge gel | $H_2O$/T gel * | (SDA)OH/T and HF/T (gel) * | Seed? | Time (days) | Major Phase | Purity |
|---|---|---|---|---|---|---|---|
| 2 | 4 | 15 | 0.5 | Y | 28 | CIT-13 | >95% |
| 2 | 4 | 15 | 0.5 | N | 35 | CIT-13 | >95% |
| 2 | 2 | 10 | 0.5 | N | 14 | CIT-13 | >95% |
| 2 | 3 | 10 | 0.5 | N | 14 | CIT-13 | ~100% |
| 2 | 4 | 10 | 0.5 | Y | 7 | CIT-13 | ~100% |
| 2 | 4 | 10 | 0.5 | N | 21 | CIT-13 | ~100% |
| 2 | 8 | 10 | 0.5 | N | 21 | CIT-13 | Major |
| 2 | 16 | 10 | 0.5 | N | 35 | CIT-13 | Major |
| 2 | 4 | 7.5 | 0.5 | Y | 14 | CIT-13 | >95% |
| 2 | 4 | 7.5 | 0.5 | N | 14 | CIT-13 | ~100% |
| 2 | 4 | 5 | 0.5 | Y | 21 | CIT-13 | >95% |
| 2 | 4 | 10 | 0.5 | N | 28 | CIT-13 | ~100% |
| 2 | 4 | 10 | 0.5 | N | 28 | CIT-13 | ~100% |
| 2 | 4 | 10 | 0.5 | N | 7 | CIT-13 | ~100% |
| 2 | 4 | 10 | 0.625 | Y | 14 | CIT-13 | >95% |
| 2 | 4 | 10 | 0.625 | N | 14 | CIT-13 | >95% |
| 2 | 4 | 10 | 0.75 | Y | 14 | CIT-13 | Major |
| 2 | 4 | 10 | 0.75 | N | 14 | CIT-13 | Major |
| 4 | 2 | 10 | 0.5 | N | 14 | CIT-13/MFI | Major |
| 4 | 4 | 10 | 0.5 | N | 14 | CIT-13/MFI | Major |
| 4 | 8 | 10 | 0.5 | N | 14 | MFI | — |
| 4 | 16 | 10 | 0.5 | N | 28 | MFI | — |
| 4 | 50 | 10 | 0.5 | N | 28 | MFI | — |
| 5 | 2 | 10 | 0.5 | N | 21 | CIT-13 | Major |
| 5 | 4 | 10 | 0.5 | N | 21 | CIT-13 | Major |
| 5 | 8 | 10 | 0.5 | N | 21 | CIT-13 | Major |
| 5 | 16 | 10 | 0.5 | N | 56 | CIT-13 | Major |
| 5 | 50 | 10 | 0.5 | N | 56 | Amorphous | — |
| 6 | 2 | 10 | 0.5 | N | 7 | CIT-13 | ~100% |
| 6 | 4 | 10 | 0.5 | N | 7 | CIT-13 | ~100% |
| 6 | 8 | 10 | 0.5 | N | 14 | CIT-13 | >95% |
| 6 | 16 | 10 | 0.5 | N | 21 | CIT-13 | >95% |
| 6 | 50 | 10 | 0.5 | N | 49 | Amorphous | — |

* T refers to the total number of Si and Ge atoms

[from Boal] Example 3.6. Screening Reactions Using Di-quat Benzyl-Imidazolium Cations (7), (8), and (9)

Table 5 shows the ratios explored for Si and Ge in the initial molecular sieve synthesis, and the resulting materials obtained when the diquaternary OSDAs were each used in a synthesis. It was observed that as the relative proportion of Ge diminished, the tendency to make *BEA with all three diquaternary OSDAs increased, consistent with previous reports that the very large diquaternary OSDA (often having para substitution relative to a central ring component) could be used to obtain very high silica *BEA phases. The *BEA is a multidimensional (3D) large pore zeolite but not so rich in 4-rings, indicative of a minor contribution of Ge.

TABLE 5

Synthesis results of Diquat OSDAs (7)-(9)

| OSDA | Si/Ge = 2 | Si/Ge = 4 | Si/Ge = 8 | Si/Ge = 16 |
|---|---|---|---|---|
| 7 | layered | layered | *BEA | *BEA |
| 8 | IWS | IWS/*BEA | *BEA | *BEA |
| 9 | BEC | BEC/*BEA | *BEA/BEC | *BEA |

Example 5. Analysis—Influences of Crystallization Parameters

Using a benzylimidazolium-derived OSDA (OSDA 2), the crystallization conditions for CIT-13 were tested systematically and kinetically at various levels of silicon-to-germanium (Si/Ge) ratios of the gel, water contents, seeding material, amounts of SDA+OH−/HF used and crystallization temperatures. The structures of OSDAs investigated in this study were displayed in Tables 1A-C, and some of the tested conditions are summarized in Table 4. The purity was qualitatively determined based on the resultant XRD profiles.

The reference crystallization condition suggested by this work that produces the-highest-quality CIT-13 crystal reproducibly was determined to be 0.8 SiO$_2$:0.2 GeO$_2$:0.5 (OSDA 1)+OH–:0.5 HF:10 H$_2$O at 160° C. With this set of crystallization parameters, an impurity-free CIT-13 sample could be obtained after 14-21 days of crystallization time. The morphology of the CIT-13 crystals very resembled that of UTL-framework materials, indicating that these two frameworks having similar 2D-portal systems are closely related. (See FIG. 2(C-D)) The other crystallization conditions varied from this reference condition. XRD profiles from several conditions that give better CIT-13 crystals than the other were displayed in FIG. 3.

Figure 4:
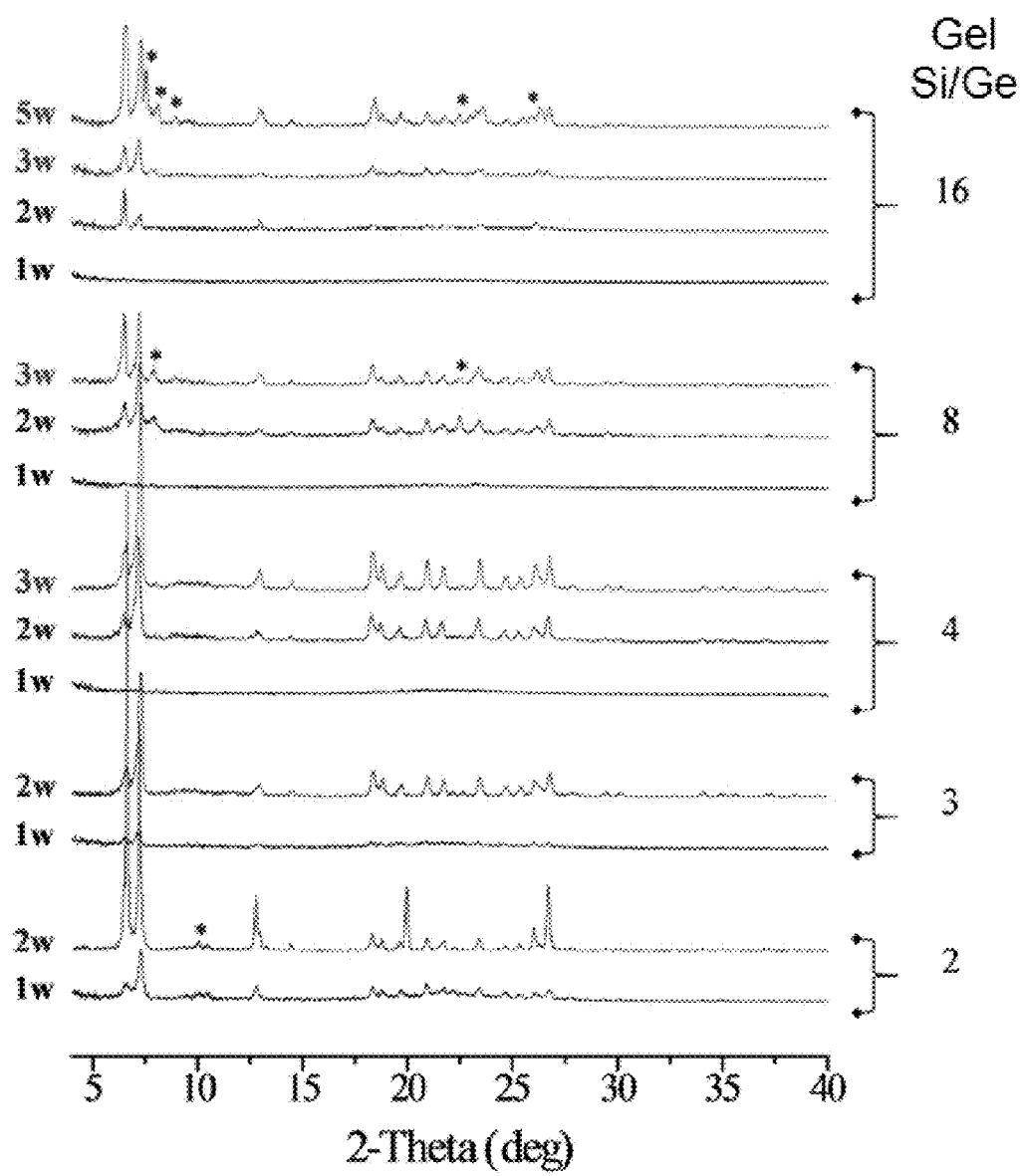
FIG. 4 illustrates a kinetic study of the effect of gel Si/Ge ratio on the crystallization of CIT-13. Only the gel Si/Ge ratio was changed and the other parameters were controlled to be the same as the reference condition. Asterisks denote impurity peaks.
Figure 5A:
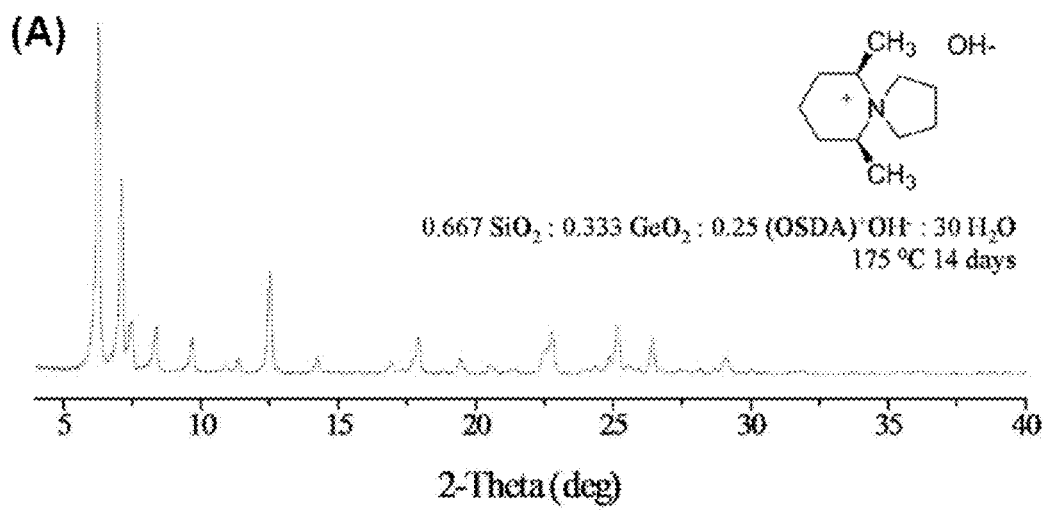
FIG. 5(A) shows an XRD profile and FIG. 5(B) shows an SEM micrograph image of the IM-12 germanosilicate sample of UTL framework synthesized in a hydroxide medium and examined to compare with CIT-13 in this study. The Si/Ge ratio of this UTL sample determined using EDS was 4.5.
Figure 5B:
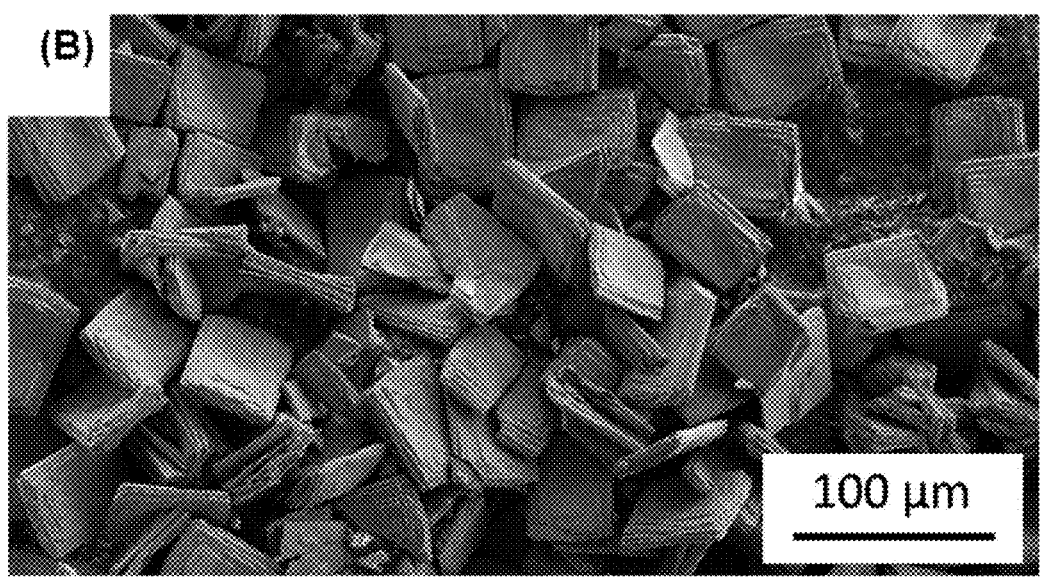
Figure 6:
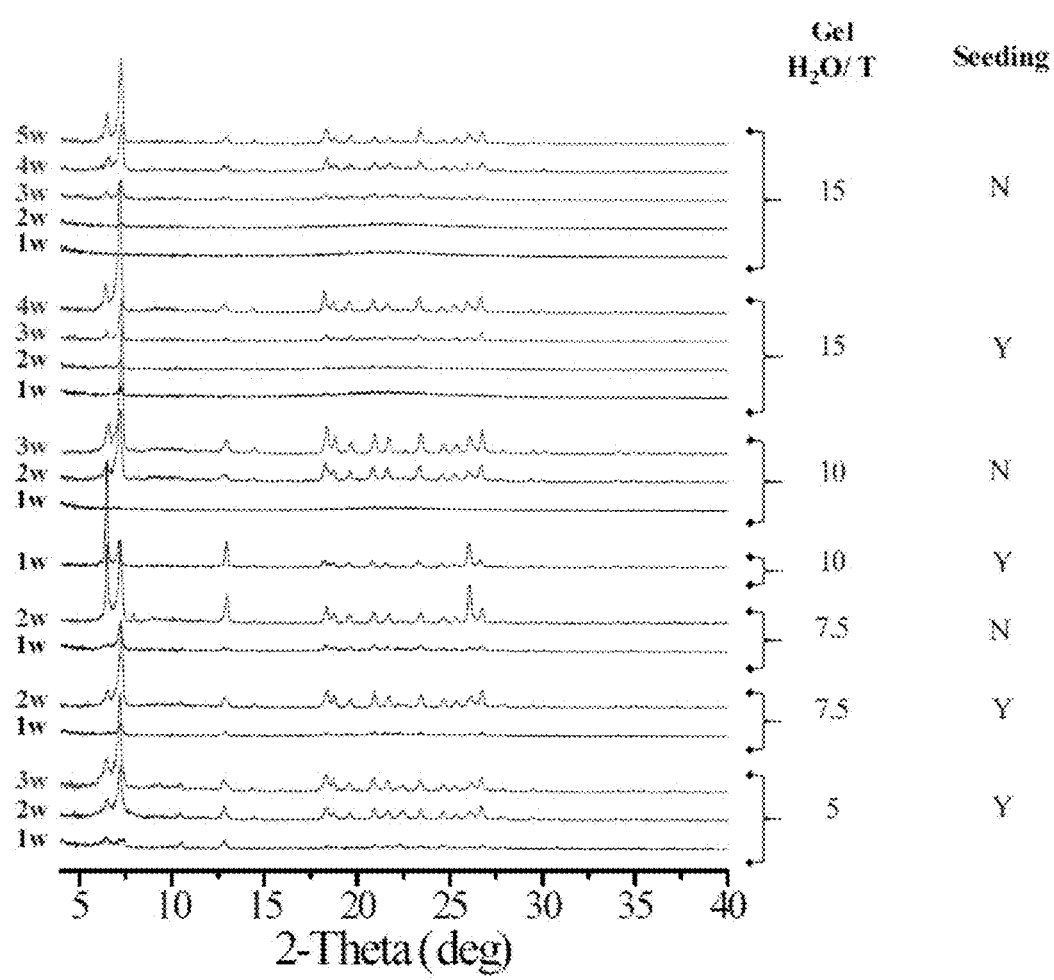
FIG. 6 illustrates a kinetic study of the effect of water levels in the gel on the crystallization of CIT-13. Only gel $H_2O$/(Si+Ge) ratio was changed and the other parameters were controlled to be the same as the reference condition.
Figure 7:
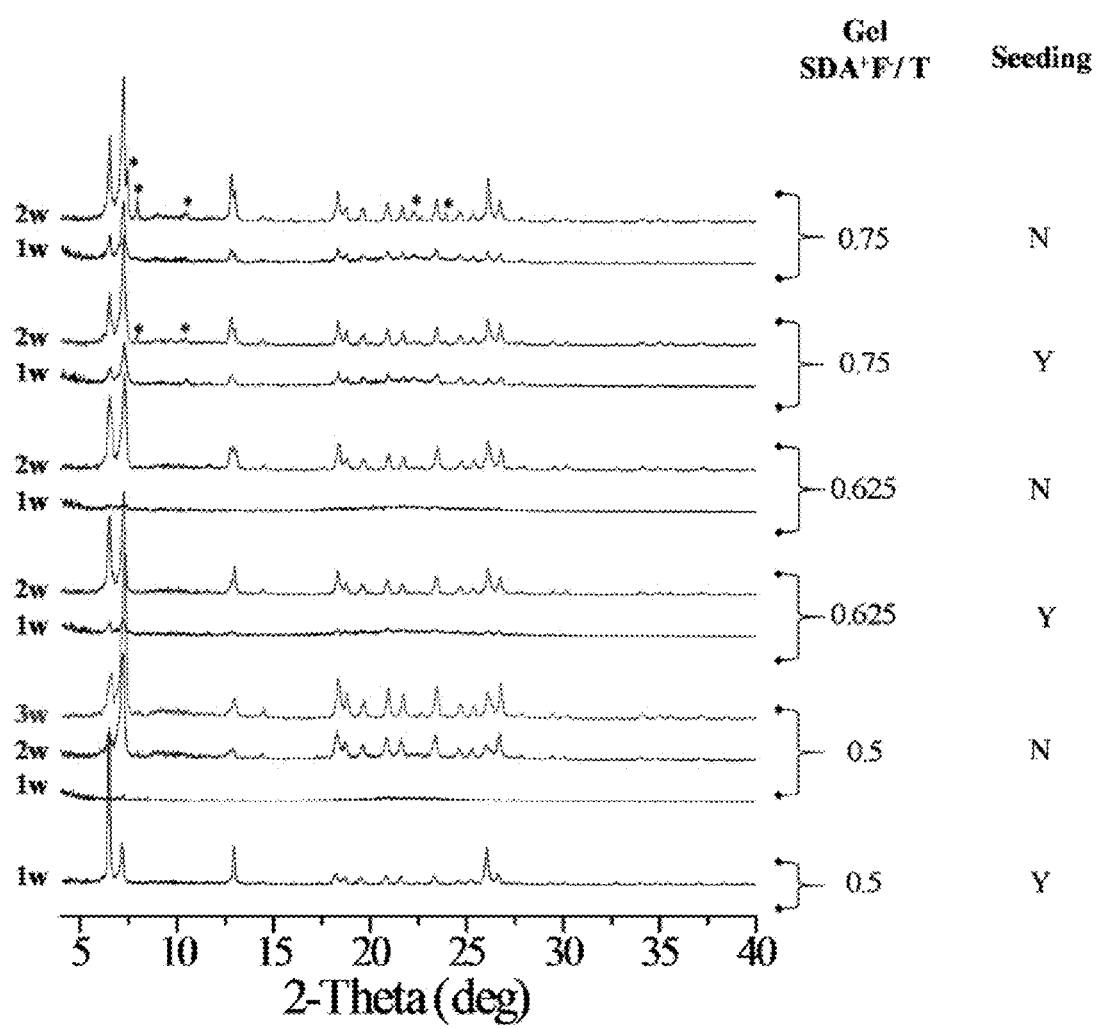
FIG. 7 illustrates a kinetic study of the effect of amount of OSDA in the gel on the crystallization of CIT-13. Only gel $(OSDA)^+OH^-$ (Si+Ge) ratio and HF/(Si+Ge) ratio were changed and the other parameters were controlled to be the same as the reference condition. Asterisks denotes impurity peaks.

The Si/Ge ratio of gel was controlled from 2 to 16, and kinetically studied using XRD. (FIG. 4). The higher Si/Ge ratio of gel led to the faster crystallization of CIT-13 and the higher germanium content in the crystals. When the gel Si/Ge ratios were 2, 3 and 4, the Si/Ge atomic ratios determined using EDS were 3.84±0.59, 4.72±0.55 and 5.73±0.89, respectively. The resultant CIT-13 crystals typically showed Si/Ge atomic ratio higher than that of the parent gels, and this fact was also true in case of the UTL sample. (FIG. 5) The amount of water in the systems also affected the crystallization process of CIT-13. It was already shown that a gel of a low water content (H$_2$O/(Si+Ge)=5) also crystallized into CIT-13 in the previous work.1 In this work, three cases of higher water levels (H$_2$O/(Si+Ge)=7.5, 10 and 15) were tested and all of them were turned out to result in faster processes and better crystallinities than the cases of H$_2$O/(Si+Ge)=5. As shown in Table 4 and FIG. 6, CIT-13 was crystallized with acceptably high purities in this range of water contents, but the cases of H$_2$O/(Si+Ge)=7.5 and 10 were close to the optimal condition in respect of purity and crystallization rate. The effect of the concentration of OSDA in the gel on the CIT-13 crystallization was also studied. (FIG. 7) The amount of HF was also changed molar-equivalently considering the neutralization process. The cases of OSDA/(Si+Ge)=0.5 and 0.625 gave relatively pure CIT-13 crystal, but some discernable impurity diffraction peaks were observed when the OSDA-to-T-atom ratio became higher than 0.75, implying that a different mode of self-assembly of OSDA molecules that directs other phase happened. Unfortunately, this phase could not be identified due to little available information.

Figure 2A:
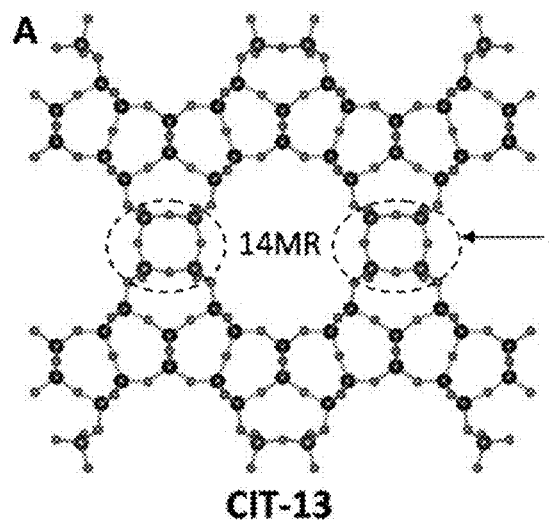
FIGS. 2(A-E) illustrate the comparison between the crystal structure of CIT-13 and UTL.
FIG. 2(E) shows alternative schematic representations of the CIT-13 structure.
Figure 2B:
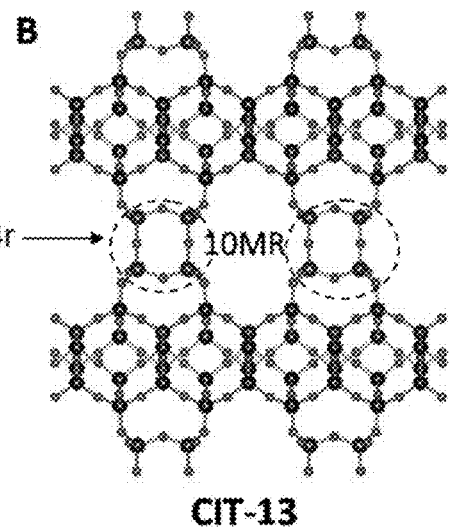
Figure 2C:
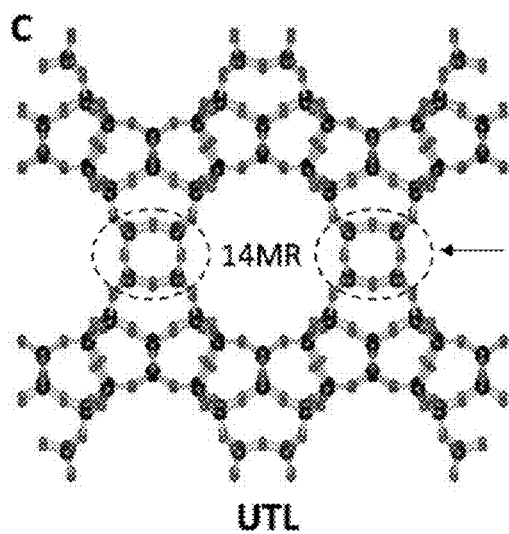
Figure 2D:
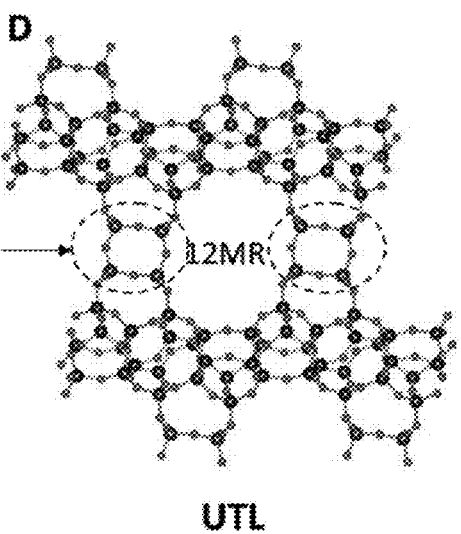
Figure 2E:
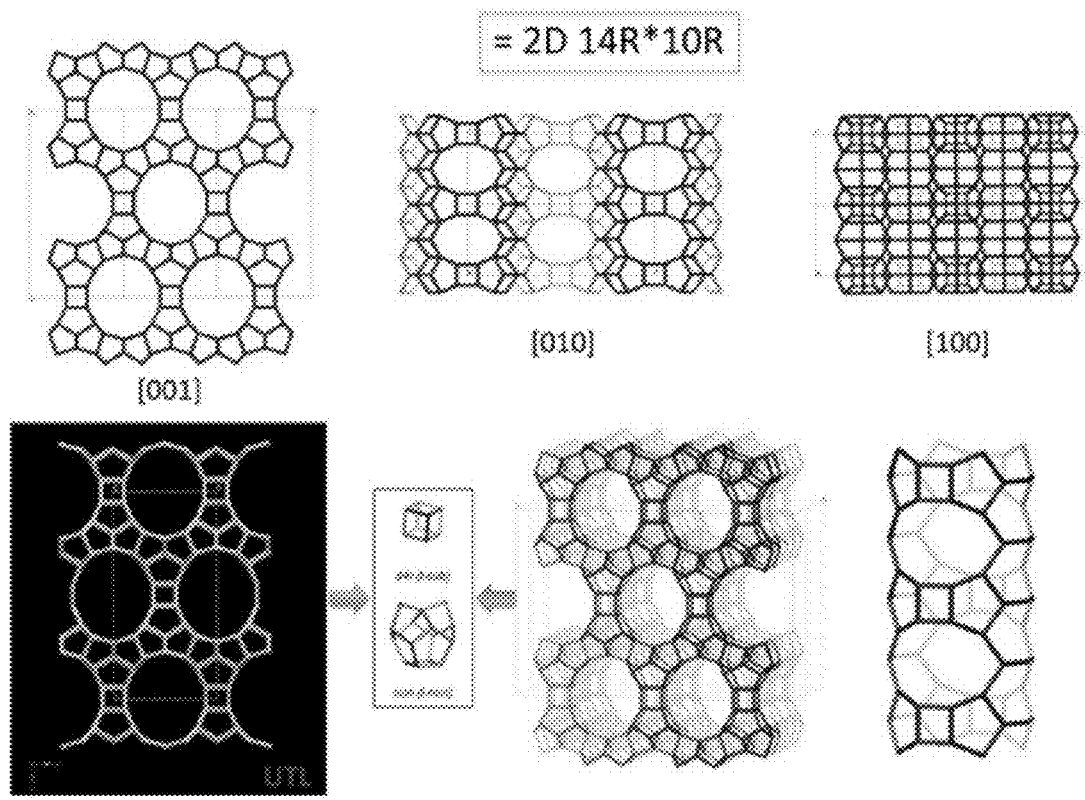
Figure 2F:
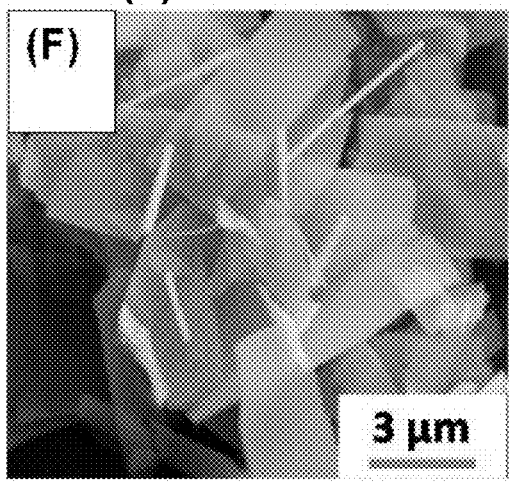
Figure 2G:
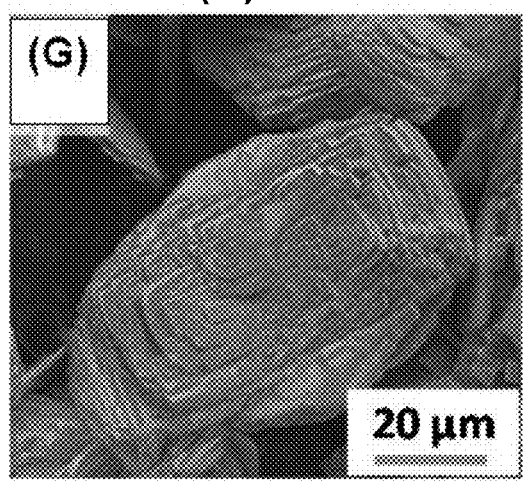
Figure 3:
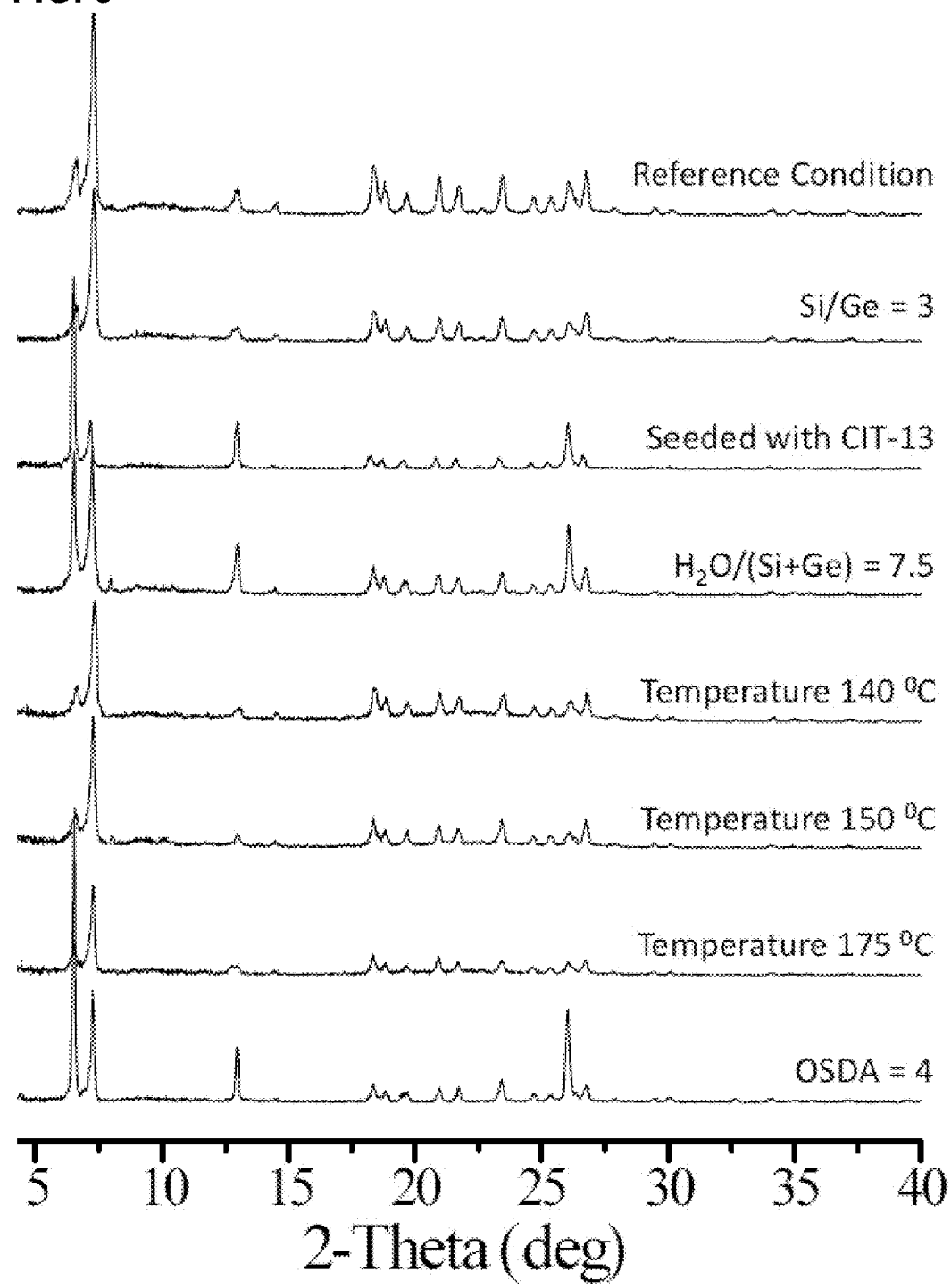
FIG. 3 shows several additional XRD profiles from selected crystallization conditions that give high-purity CIT-13 germanosilicates. The $1^{st}$ (top) profile is from the reference condition of 0.8 $SiO_2$:0.2 $GeO_2$ (Si/Ge=4): 0.5 $OSDA^+$ $OH^-$:0.5 HF:10 $H_2O$ at 160° C. without seeding. Each of the following ($2^{nd}$ to 8th) profiles has a specified condition deviated from the reference condition
Figure 8:
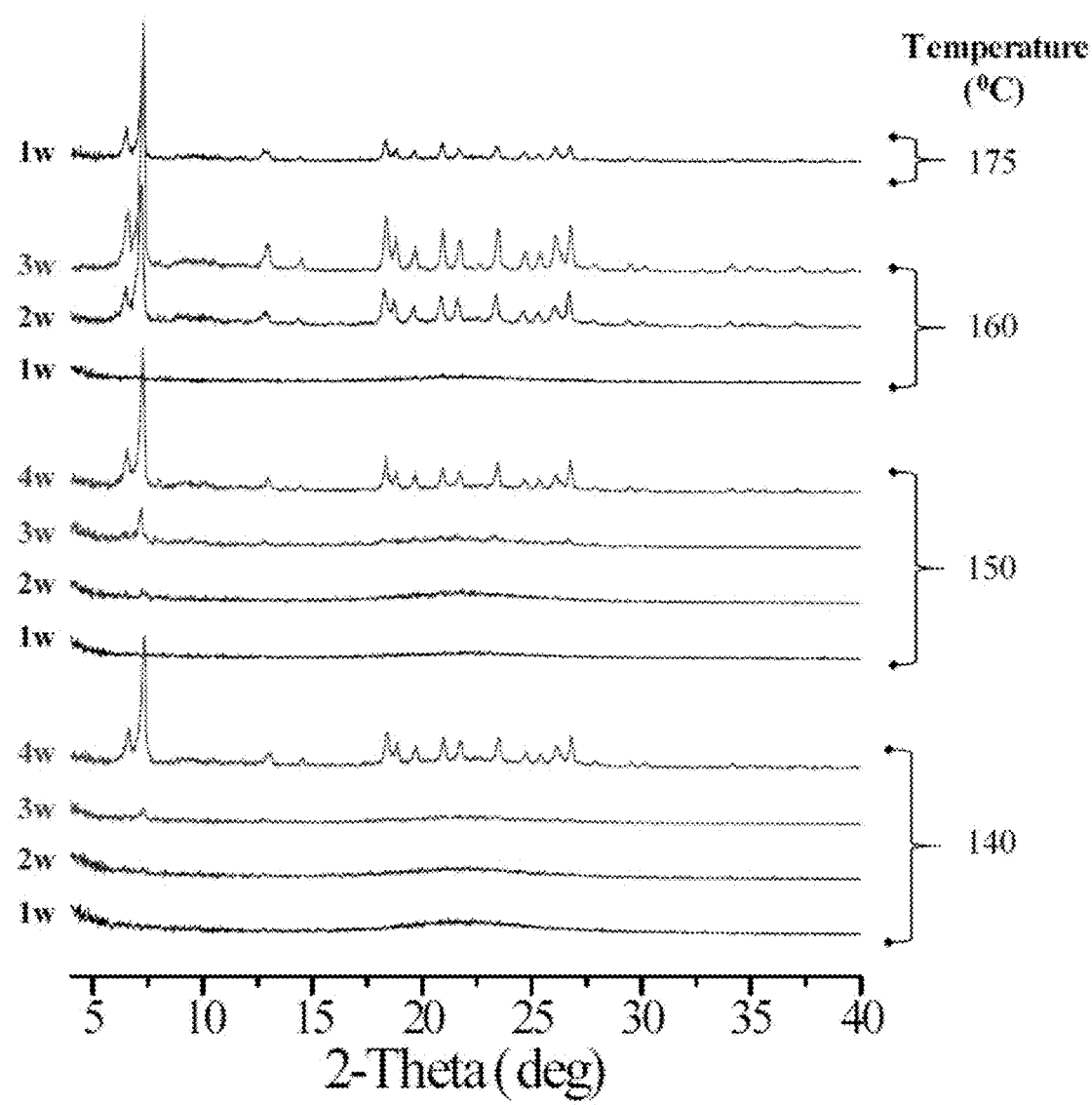
FIG. 8 illustrates a kinetic study of the effect of crystallization temperature on the crystallization of CIT-13. Only the crystallization temperature was changed and the other parameters were controlled to be the same as the reference condition
Figure 9:
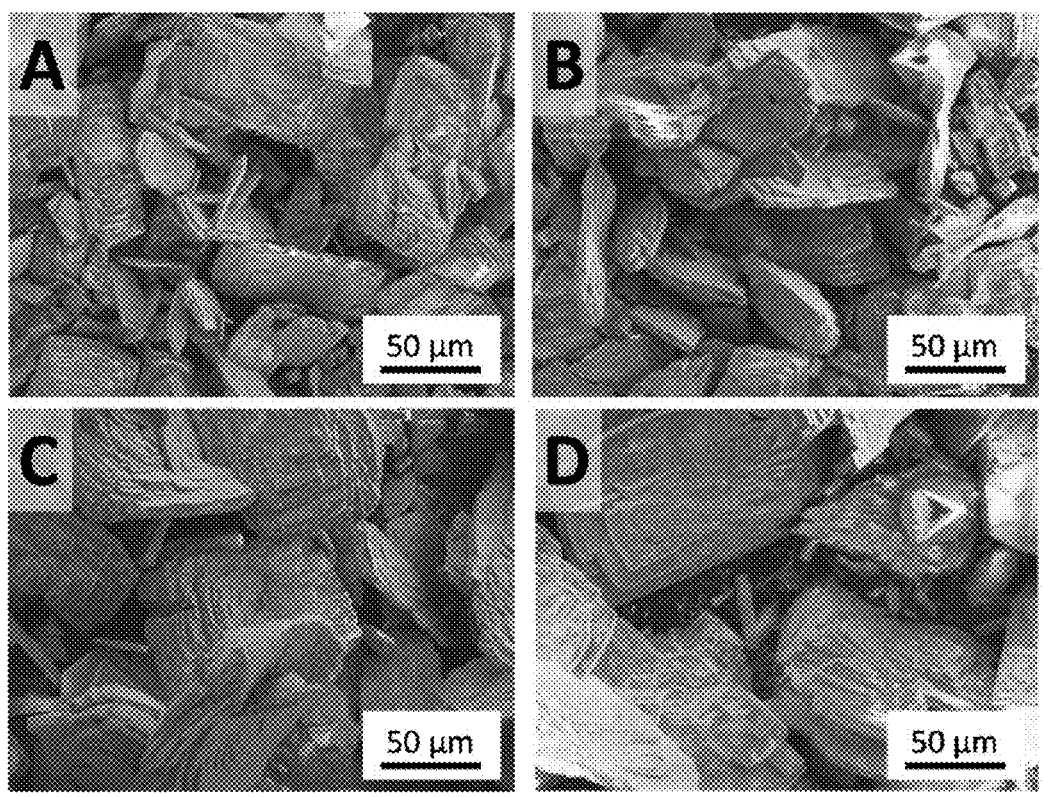
FIG. 9 shows SEM micrographs of CIT-13 crystallized at different temperatures: (A) 140° C., (B) 150° C., (C) 160° C. and (D) 175° C.

With the reference gel composition, the influence of temperature on the crystallization process of CIT-13 was also studied. As illustrated in FIG. 3, pure CIT-13 was synthesized at all studied temperatures: 140, 150, 160 and 175° C. The crystallization was faster at higher temperature; at 175° C., CIT-13 was purely synthesized within 1 week even without initial seeding, whereas at least 4 weeks were required at 140 and 150° C. (FIG. 8) Furthermore, as shown in FIG. 9, an increased crystallization temperature resulted in bigger crystals, indicating that the crystallization process of CIT-13 is diffusion-controlled.

Example 6. Analysis—OSDAs and Crystallization of CIT-13

Figure 10:
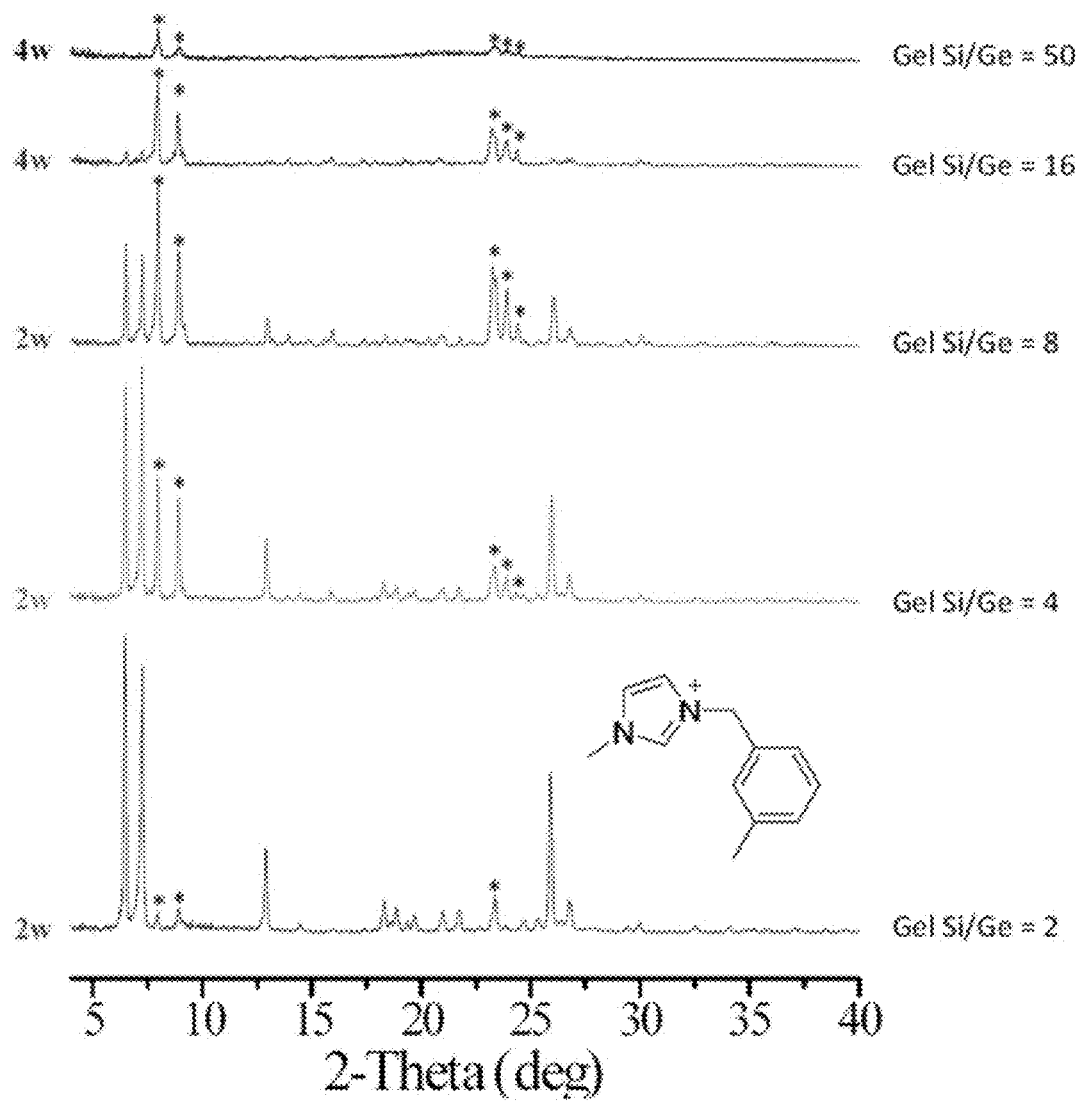
FIG. 10 shows XRD profiles of crystallized germanosilicate samples with various gel Si/Ge ratios from OSDA 4. Asterisks (*) denote impurity peaks. Here, the impurity phase was identified as MFI.
Figure 11:
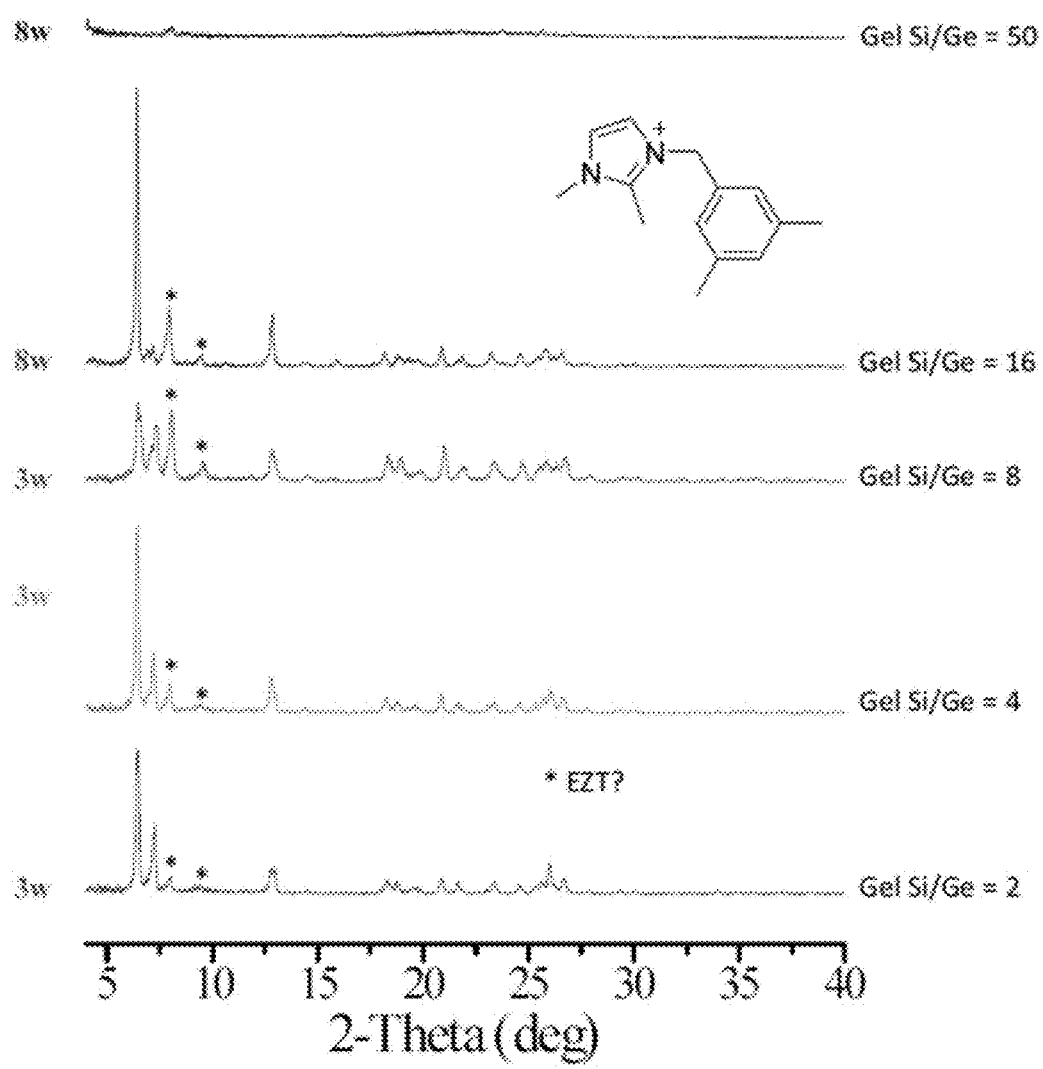
FIG. 11 shows XRD profiles of crystallized germanosilicate samples with various gel Si/Ge ratios from OSDA 5. Asterisks (*) denote impurity peaks
Figure 13:
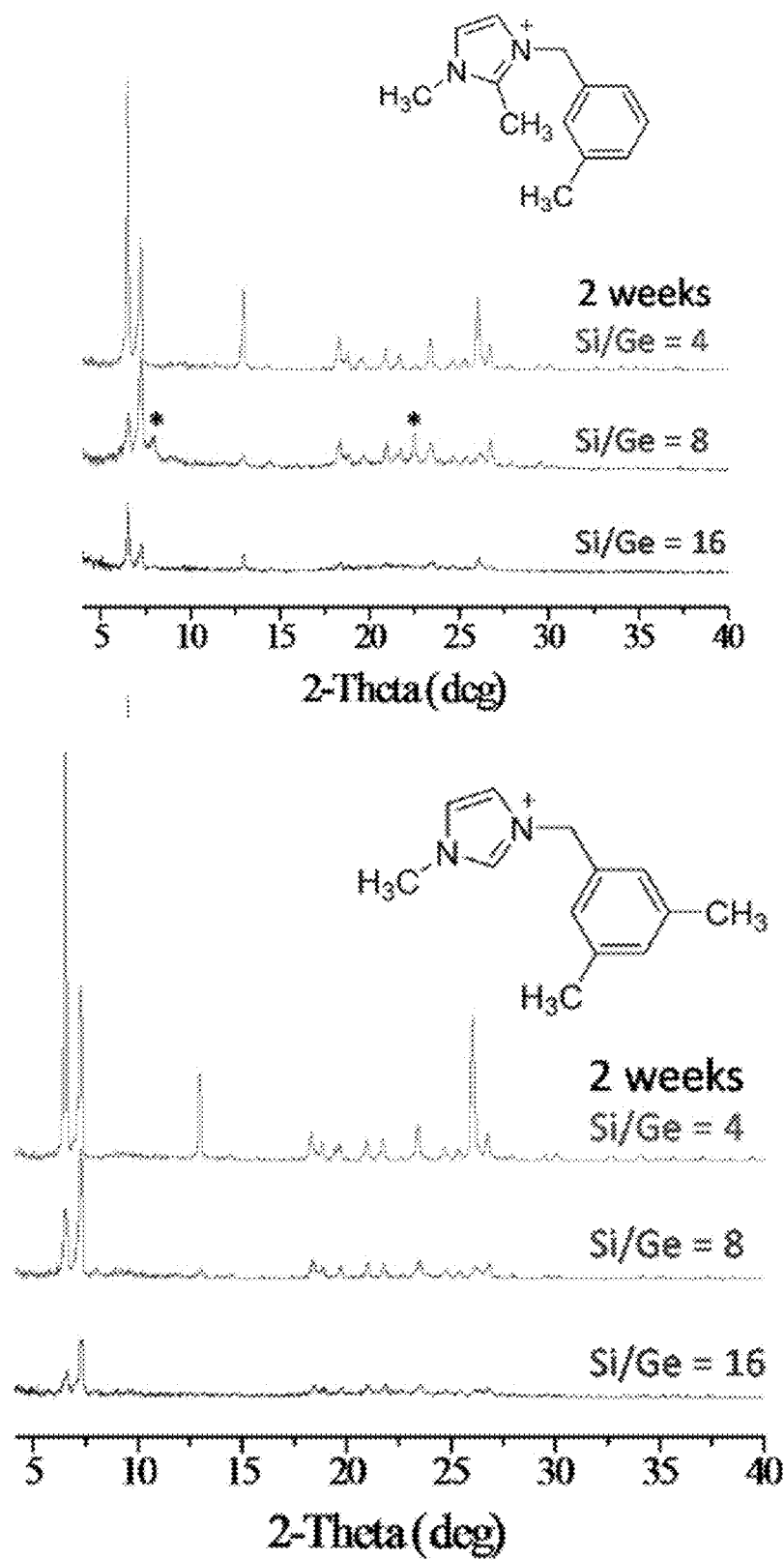
FIG. 13 illustrates the typical powder XRD profiles of the resultant CIT-13 crystals at several levels of gel Si/Ge ratios from (A) OSDA 2 and (B) OSDA 6, with gel compositions x/(x+1) SiO$_2$:1/(x+1) GeO$_2$:0.5 (OSDA)+OH−:0.5 HF:10 H$_2$O where x is the gel Si/Ge ratio. Asterisks (*) denote impurity peaks.

The substitution position of the methyl group on the benzene ring of OSDA molecule played an important role in determining the resultant germanosilicate framework; ortho-, meta- and para-monomethyl-substituted benzylimidazolium derivatives yielded IWS/impure CIT-13, pure CIT-13 and LTA framework, respectively. In this work, the crystallization processes of CIT-13 from three selected OSDAs (OSDA 4-6) that have one or two methyl groups only on the meta-positions were studied at various gel Si/Ge ratio from 2 to 50, in addition to OSDA 2. The XRD profiles in FIGS. 10-12 indicate that all of the four OSDAs structure-directed the crystallization of microporous germanosilicate to CIT-13 frameworks. Therefore, it is likely that the meta-substitution of methyl group(s) on the OSDA-benzene ring is an important precondition for CIT-13 production. Specifically, OSDA 2 and OSDA 6 yielded much purer CIT-13 than the others; the syntheses using these two SDAs resulted in pure CIT-13 germanosilicate crystals with negligible or none of impurity phases as shown in FIGS. 10-11 and 13. OSDA 4 resulted in the mixture of CIT-13 and MFI framework. When the system was Ge-rich, CIT-13 took the majority, while MFI was the major phase when the gel Si/Ge was high. (FIG. 10) OSDA 5 also resulted in CIT-13, but one or more impurity phase(s) were observed at all tested gel Si/Ge ratios (FIG. 11).

Figure 14A:
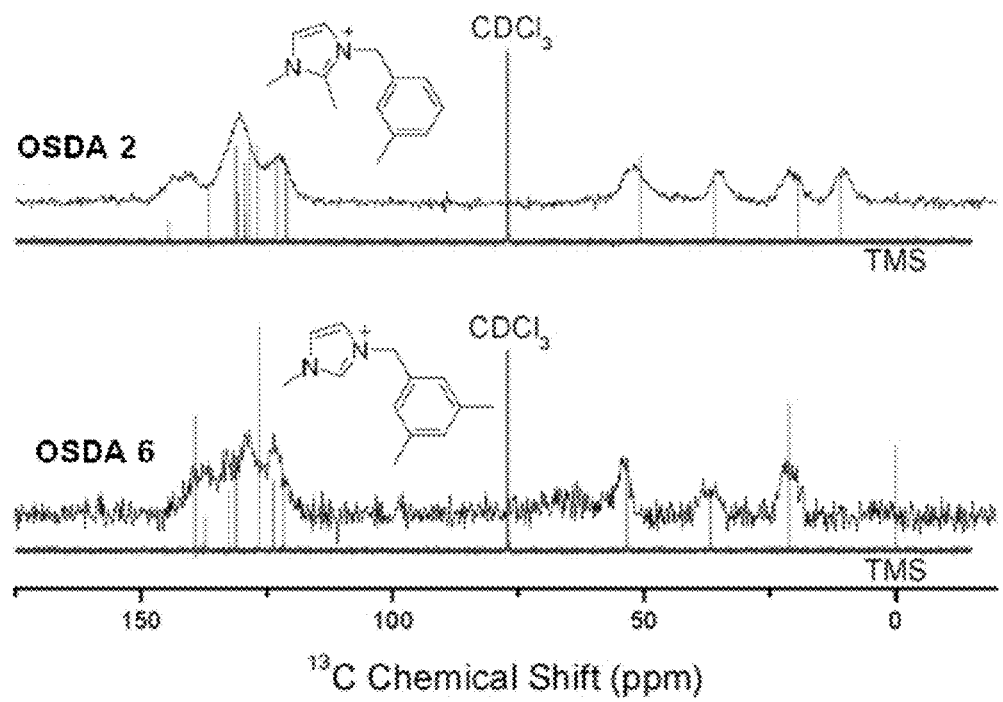
FIG. 14 shows (A) the $^1$H-decoupled $^{13}$C Solid-State MAS (8 k) NMR spectra (upper spectra) of OSDA 2 and OSDA 6 filling the pores and channels of the as-prepared CIT-13 inorganic frameworks overlapped with the corresponding $^{13}$C liquid NMR spectra (lower peaked spectra) of each OSDA. (B) The TGA profiles of as-prepared CIT-13 synthesized from OSDA 2 and OSDA 6.
Figure 14B:
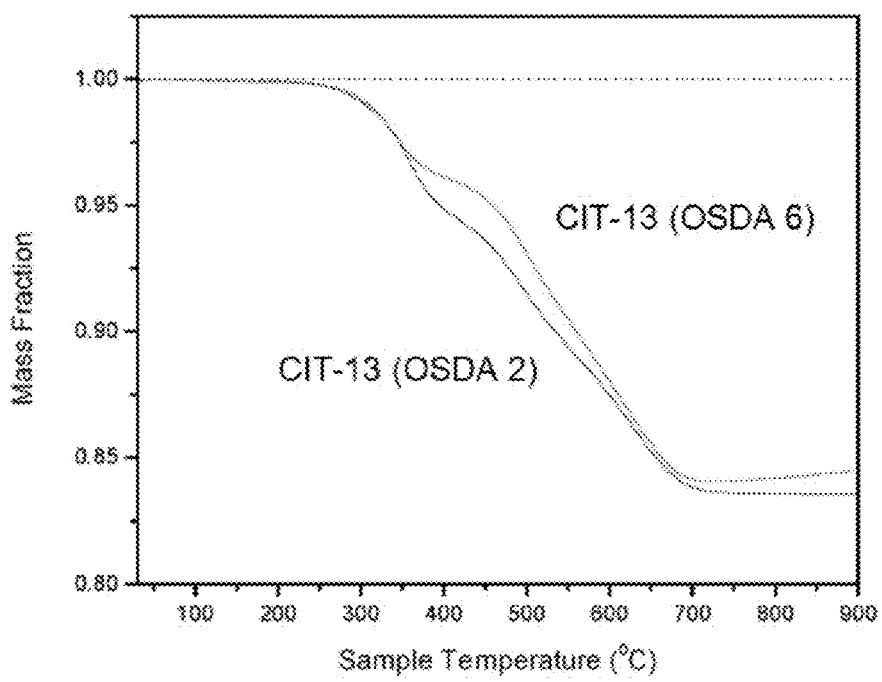

The as-prepared CIT-13 products from OSDA 2 and OSDA 6 were closely examined using $^{13}$C NMR and TGA which were displayed in FIG. 14(A-B). The peaks from the solution-phase $^{13}$C NMR spectra of OSDA 2 and OSDA 6 matched those from the solid-state $^{13}$C MAS NMR of as-prepared CIT-13 germanosilicate incorporating each OSDA. (See FIG. 14(A)) Together with well-defined CIT-13 XRD profiles from these OSDAs demonstrated above, it can be concluded that these two different OSDA molecules structure-directed the same framework CIT-13 without being dissociated during the crystallization. The TGA curves of as-prepared CIT-13 shown in FIG. 14(B) manifest approximately 16.5% (OSDA 2) and 15.6% (OSDA 6) weight loss during the temperature ramping from room-temperature to 900° C. indicating that a unit cell (64 T atoms) of CIT-13 has four OSDA molecules. Since the molecular weights of OSDA 2 and OSDA 6 are the same, the small difference between the two weight loss values may be due to difference crystal-Si/Ge ratios of the two independent samples. A value of ~17% of OSDA weight loss was a reasonable value for a microporous material having a 2-dimensional pore system of perpendicularly intersecting 14 and 10 MR channels.

Example 4. Structure Analysis of As-Synthesized CIT-13

A sample of CIT-13 produced using the reference conditions was used for structural analysis. The structure was solved from rotation electron diffraction (RED) data using the zeolite-specific program FOCUS (S. Smeets, et al., *J. Appl. Crystallogr.*, 2013, 46, 1017-1023). Rietveld refinement was initiated in the space group Cmmm (a=13.77 Å, c=27.32 Å) using the coordinates of the structure for CIT-13 proposed previously and the program TOPAS (A. A. Coelho, TOPAS-ACADEMIC v5.0, in, 2012).

The refinement resulted in a good fit to the data with agreement values $R_f$=0.013 and $R_{wp}$=0.077 ($R_{exp}$=0.0015). The main differences seem to arise from an anisotropic peak shape that affects some of the reflections. The refinement yields a Si:Ge ratio of 5.63. The Ge is located primarily on T7 in the d4r, about half of which is Ge. The total occupancy of the OSDAs refined to 0.103, giving a total of 3.26 OSDA molecules per unit cell (out a possible total of 4). Only 2 F$^-$ were found, so the remaining difference in the charge to balance the positively charged OSDA was expected to be made up by 1.26 OH$^-$ disordered in the channel system. (See FIG. 2)

TABLE 6

Crystallographic details for the structure refinement of as-synthesized CIT-13.

| Sample | CIT-13 |
|---|---|
| Chemical composition | $|(C_{13}N_2)_{3.30}F_2|[Si_{54.34}Ge_{9.66}O_{128}]$ |
| Space group | Cmmm |
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1) |
| 2θ range (°) | 2.0-46.0 |
| $R_I$ | 0.0126 |
| $R_{wp}$ | 0.0773 |
| $R_{esp}$ | 0.0015 |
| Observations | 16899 |
| Reflections | 1241 |
| Parameters | 104 |
| Geometric restraints | 62 (inorganic germanosilicate) |
|  | 38 (OSDA) |

TABLE 7

Selected bond lengths and angles (Å, °).

|  |  | T—O—T | O—T—O | T—O |
|---|---|---|---|---|
| CIT-13 | min | 138.3 | 107.8 | 1.55 |
|  | max | 180.0 | 113.8 | 1.63 |
|  | avg | 156.6 | 109.6 | 1.59 |

Restraints used:
T—O—T: 135 ± 10°;
O—T—O: 109.5 ± 0.8°;
T—O: 1.61 ± 0.01 Å;
w= 1/σ$^2$

Example 7. Comparison Between CIT-13 and UTL

Figure 15A:
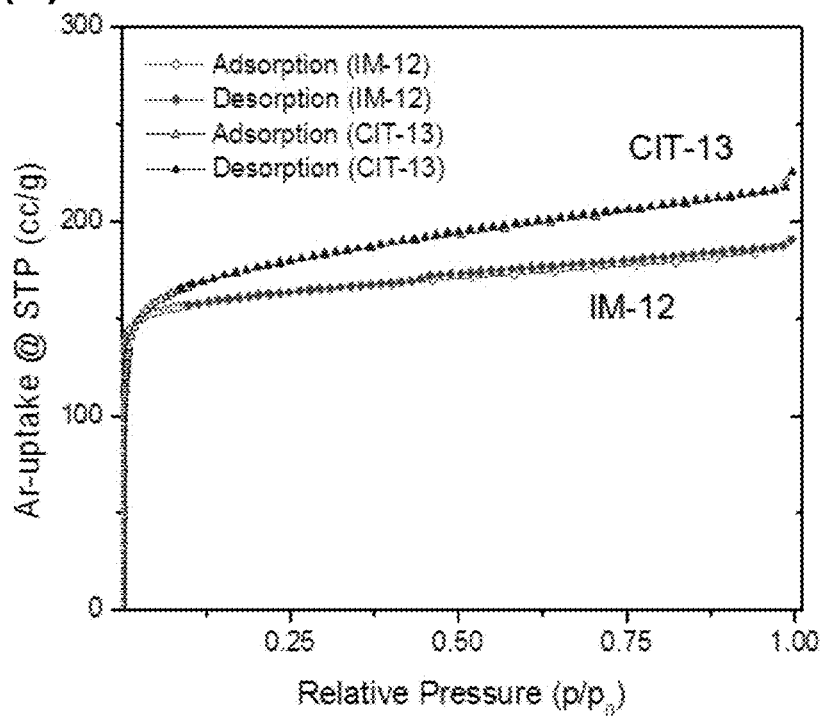
FIGS. 15(A-B) show 87K Ar-cryogenic physisorption isotherms of as-calcined CIT-13 and IM-12, FIG. 5(A) linear and FIG. 5(B) log scale.
Figure 15B:
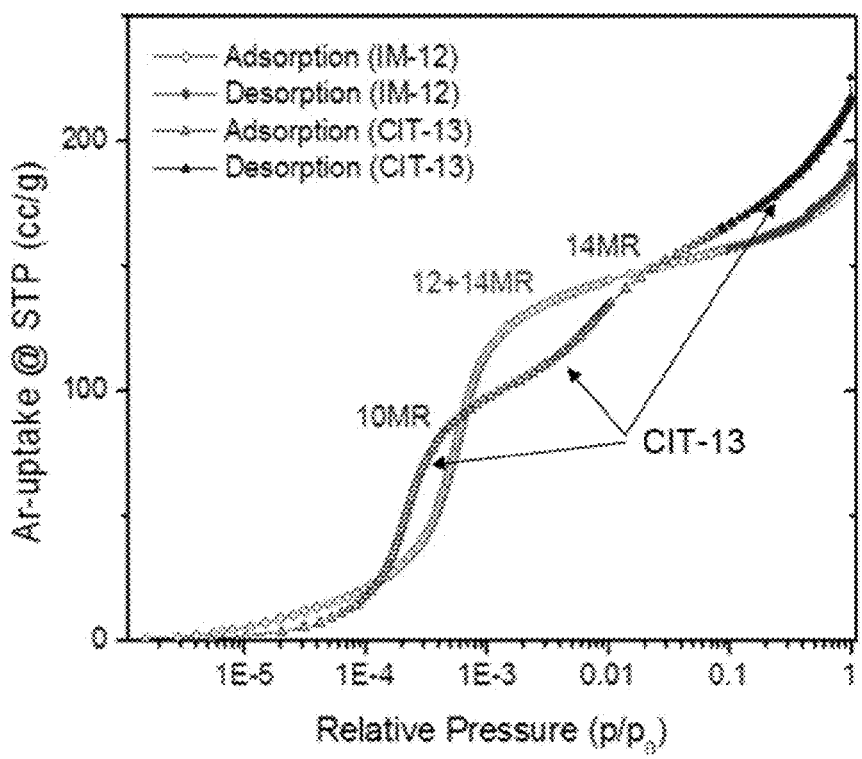

Table 8 shows a comparison of the physicochemical data related to the channel and pore systems of IM-12 and CIT-13. The micropore volume found for IM-12 is consistent with the previously reported results. The micropore volume of CIT-13 was slightly smaller than that of IM-12, which is consistent with the fact that the framework density for CIT-13 (16.41 T-atoms nm$^{-3}$) is higher than that of IM-12 (15.60 T-atoms nm$^{-3}$). The physisorption isotherm of CIT-13 showed two distinct pore filling phenomena in the micropore adsorption region (FIG. 15B). It is possible that the first pore filling at $p/p_o \sim 10^{-4}$-$10^{-3}$ arose from the high eccentricity of the 10-ring channels and the second one at $p/p_o = 10^{-2}$ was as observed because the average occupancy of 0.8 could no longer be reached. Such an ordered arrangement is highly unlikely. However, it does show that an A layer could become a B layer very easily and that the OSDA would not fit at the boundary between the two, thus creating a deficiency in the amount of OSDA incorporated into the structure.

TABLE 8

Comparison of channel and pore systems of IM-12 and CIT-13, calculated based on germanosilicated of the Si/Ge ratio characterized using EDS

|  |  | IM-12 | CIT-13 |
|---|---|---|---|
| Sample Si-to-Ge ratio |  | 4.5 | 5.0 |
| Space group |  | C2/m (monoclinic) | Cmmm (orthorhombic) |
| Framework Density (T-atoms per nm$^3$) |  | 15.60 | 16.41 |
| Material density (g/cm$^3$) | Pure silica | 1.56 | 1.64 |
|  | Germanosilicate | 1.77 | 1.84 |
| Channel dimension |  | 14 (9.5 × 7.1 Å) | 14 (9.1 × 7.2 Å) |
|  |  | 12 (8.5 × 5.5 Å) | 10 (6.2 × 4.5 Å) |
| Micropore volume (cm$^3$/g) | Theoretically available | 0.376 | 0.352 |
|  | t-plot method | 0.177 | 0.182 |
|  | Saito-Foley | 0.205 | 0.222 |

Although the OSDA molecule was disordered, it seemed that two OSDA molecules adopted a supramolecular arrangement at the center of the 14-ring, in carrying out their structure-directing effect. The imidazole rings of an OSDA pair are parallel to one another, with a centroid distance of 3.54(1) Å. Each pair can adopt one of four different symmetry-related positions. The methylbenzyl groups on either end of an OSDA pair point into the 10-rings. The occupancy of the OSDA refines to 0.8, and this allows neighboring OSDA pairs to adopt a different orientation occasionally.

Example 7. Analysis—Structural Comparison Between CIT-13 and UTL

Figure 16A:
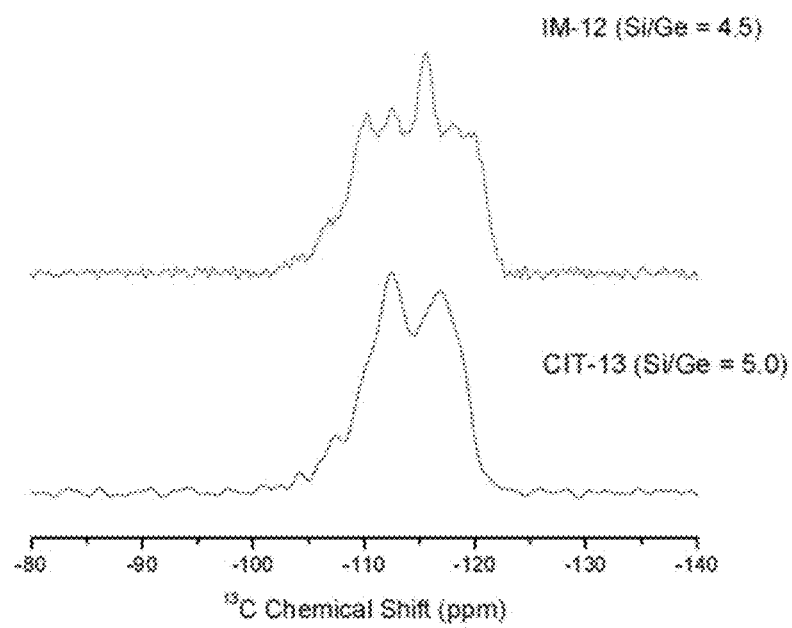
FIG. 16(A) shows $^{29}$Si 8K MAS solid-state NMR spectra of as-calcined CIT-13 (lower trace) and IM-12 (upper trace).
Figure 16B:
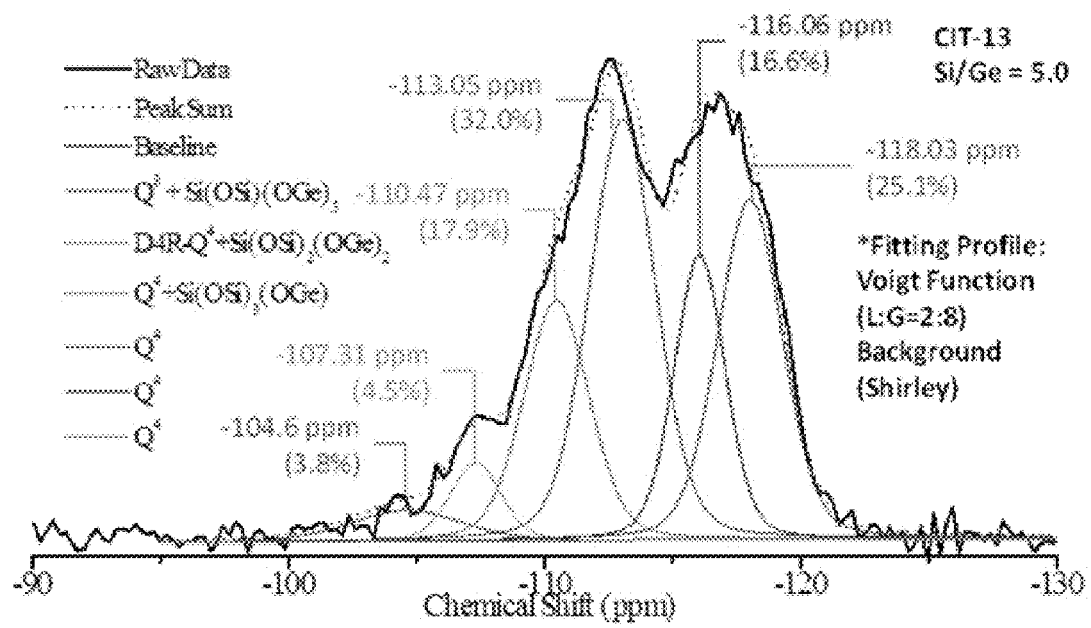
FIG. 16(B) shows the deconvoluted $^{29}$Si 8K MAS solid-state NMR spectra of as-calcined CIT-13 (Si/Ge=5.0), with chemical shifts at −104.6 ppm (3.8%), −107.31 ppm (4.5%), −110.47 ppm (17.9%), −113.05 ppm (32.0%), −116.06 ppm (16.5%), −118.03 ppm (25.1%). Solid line is actual spectrum; dotted line is sum of the indicated peaks.
Figure 17A:
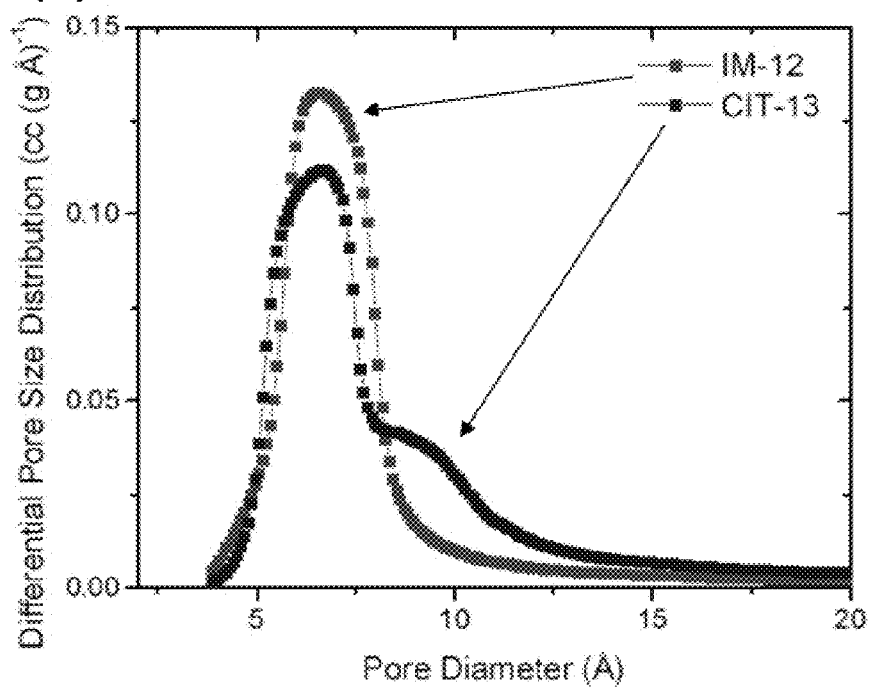
FIGS. 17(A-C) shows a comparison of differential pore size distribution for IM-12 and CIT-13.
Figure 17B:
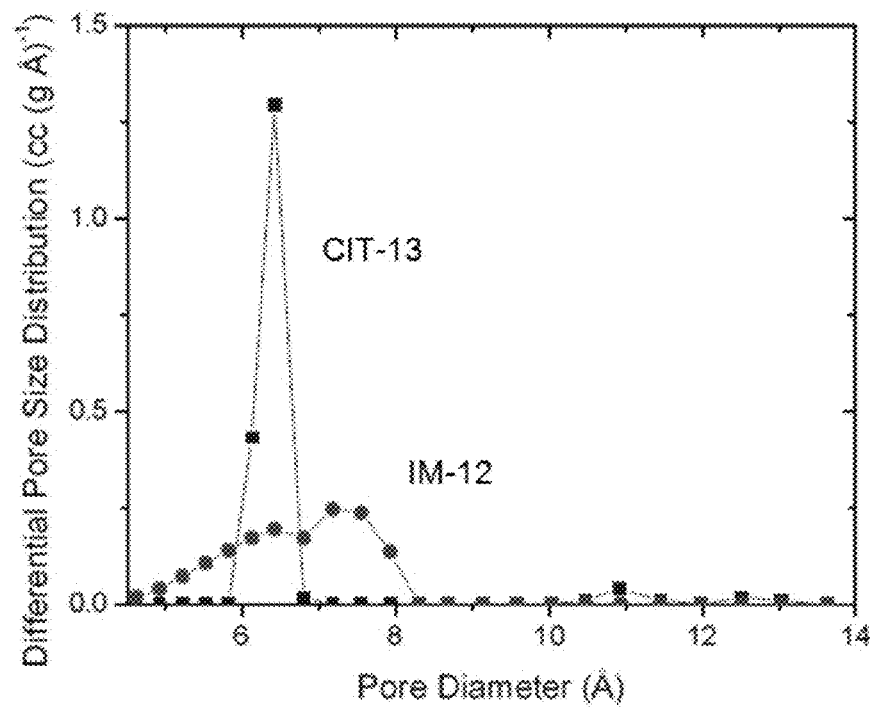
Figure 17C:
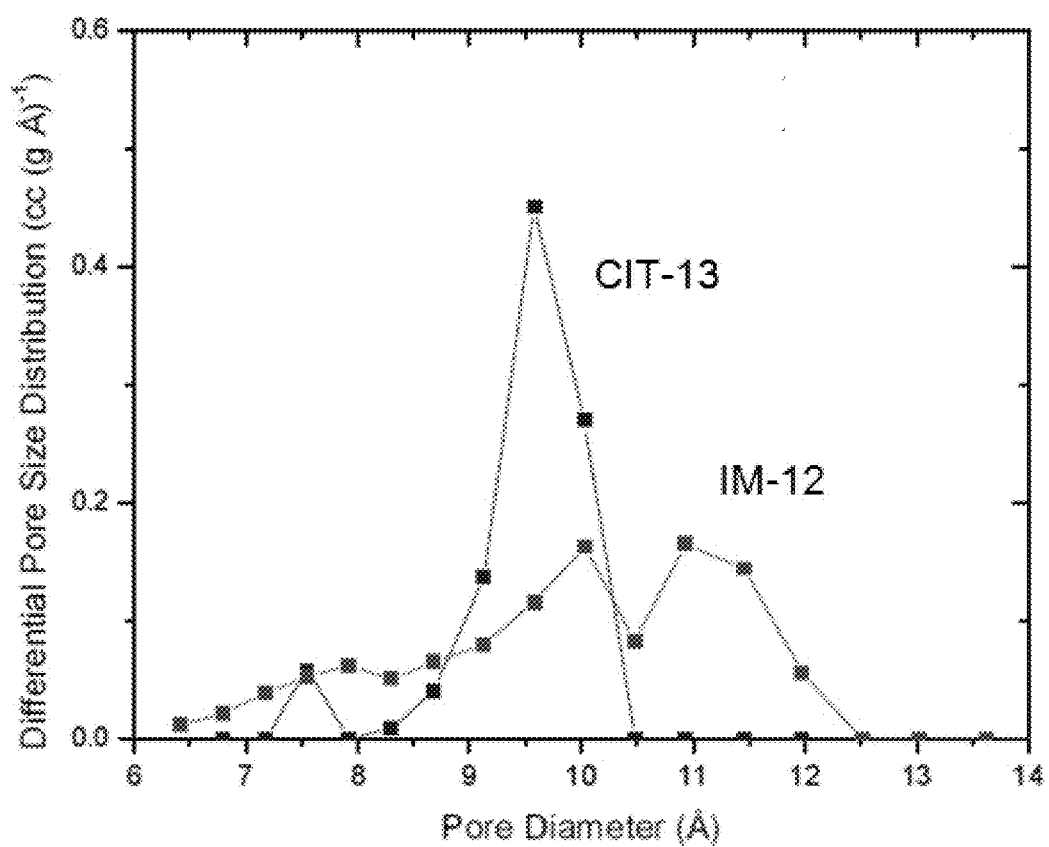
Figure 18A:
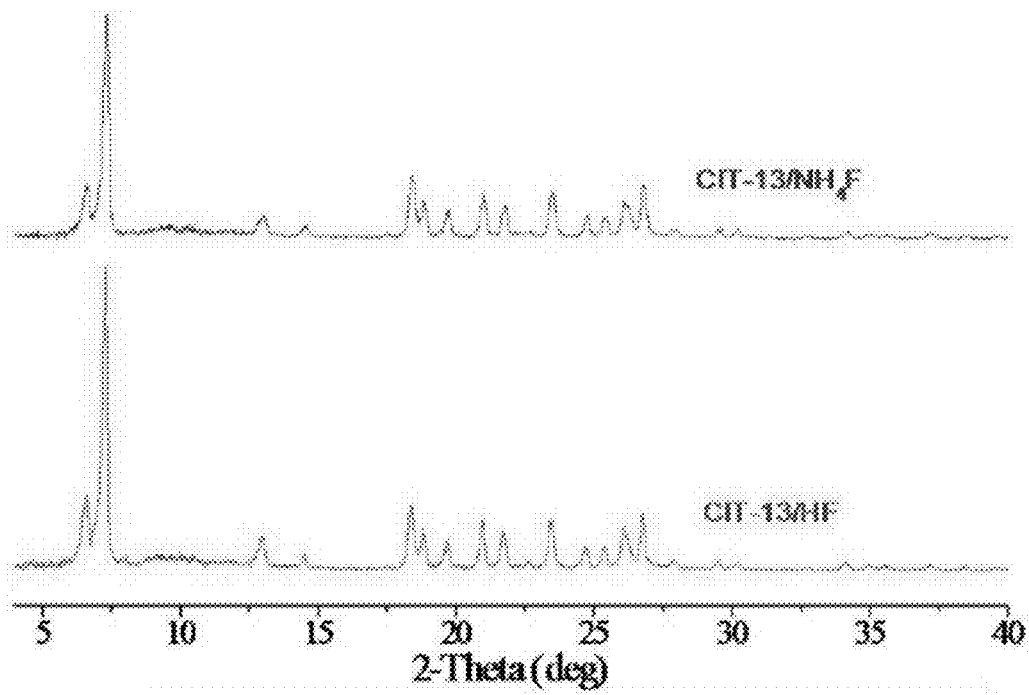
FIG. 18(A) shows powder XRD profiles of CIT-13 from HF-protocol and NH$_4$F-protocol.
Figures 18B, 18C:
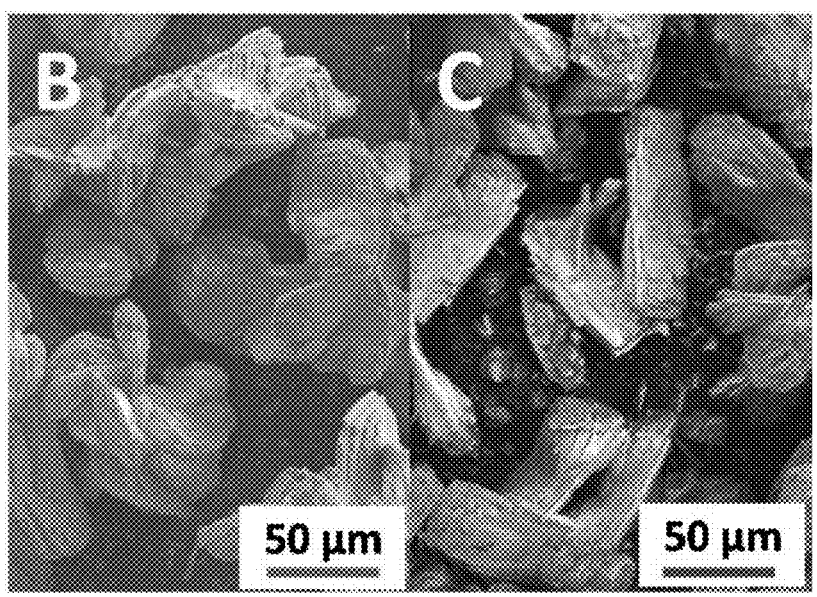
FIGS. 18(B-C) show SEM micrograph images of CIT-13 from (B) HF-protocol and (C) NH$_4$F-protocol.
FIG. 18(D) provides TGA profiles of CIT-13 from HF-protocol and NH$_4$F-protocol.
Figure 18D:
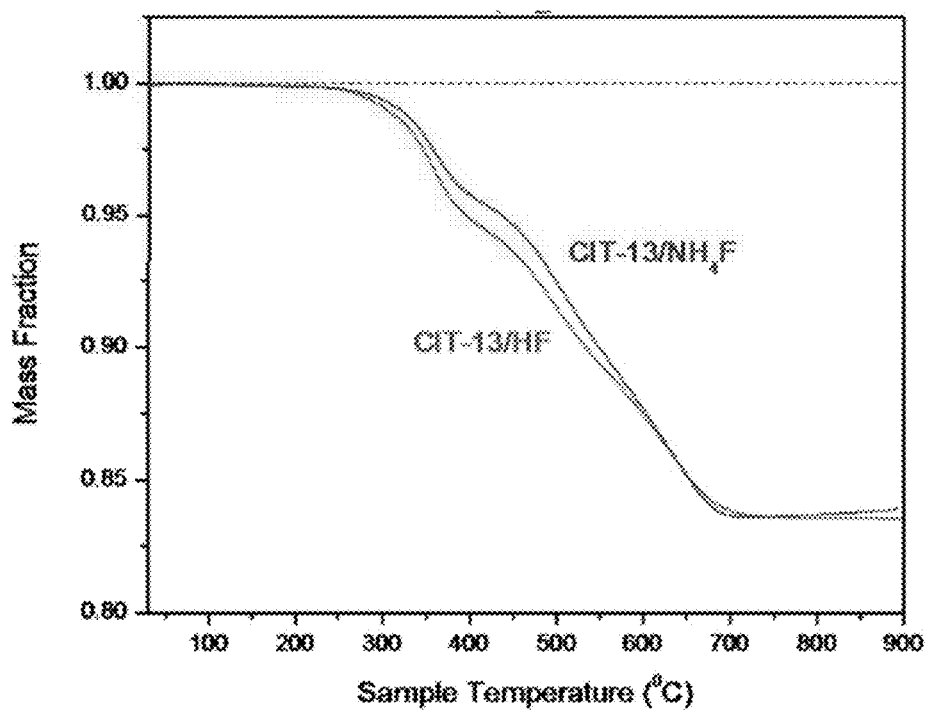
Figure 18E:
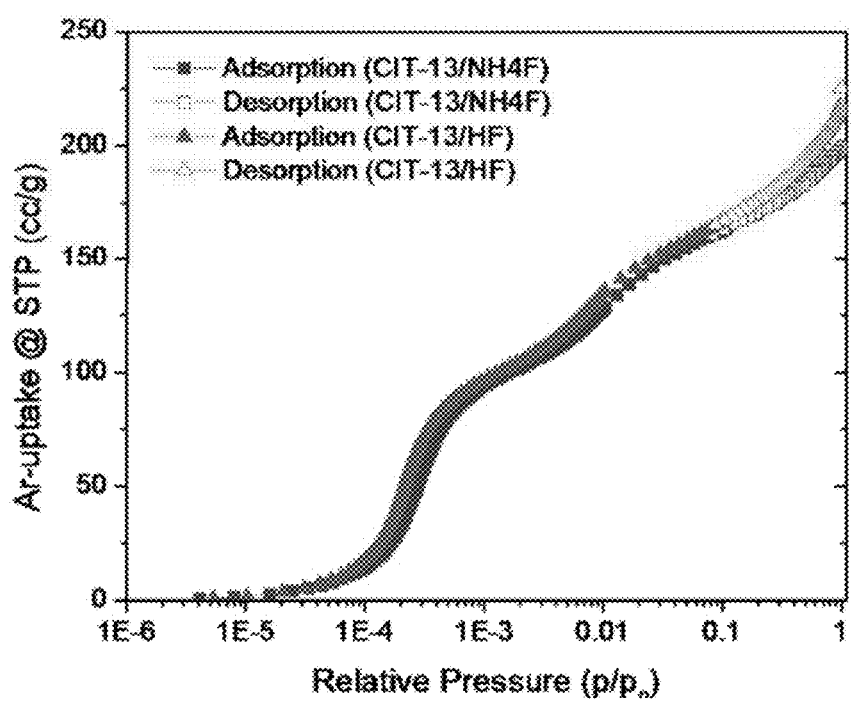

As mentioned above, the crystal structure of CIT-13 from an orthorhombic space group Cmmm was very closely related to that of UTL belonging to a monoclinic space group C2/m. To directly make comparisons between the two structures experimentally, Argon physisorption isotherms and $^{29}$Si solid-state NMR spectra were obtained for both of the two frameworks. (FIG. 16). The CIT-13 sample characterized in this part was synthesized from the reference condition. The crystal Si/Ge ratio checked using EDS of this CIT-13 was 5.0±0.5. For UTL, IM-12 was synthesized separately from a hydroxide-medium, and its Si/Ge ratio was determined to be 4.5±0.3. All samples subjected to these structural studies were freshly calcined before the measurements.

The argon cryogenic physical adsorption isotherms of CIT-13 and UTL were obtained at 87 K. (see FIG. 15) The micropore volumes of CIT-13 and UTL obtained using the t-plot methods were 0.177 cm$^3$/g and 0.182 cm$^3$/g, respectively, the latter value being consistent with previously reported results. The smaller micropore volume of CIT-13 than that of UTL was consistent with the denser framework of CIT-13; the framework density of UTL is 15.60 T-atoms nm$^{-3}$, while that of CIT-13 is 16.41 T-atoms nm$^{-3}$. These framework density values were computed from CIF files of the two frameworks using an open topological analysis tool TOTOPOL (see M. D. Foster, et al., A Database of Hypothetical Zeolite Structures, available at http://www.hypotheticalzeolites.net at the time of this writing). The calcined CIT-13 showed a two-step argon adsorption behavior at very low pressure range, indicating that the adsorption behavior inside the 10MR-channel is very different to that of the 14MR-channel in viewpoint of the micropore-filling mechanism. This eccentricity was not observed in the UTL framework. The micropore volume characterized based on the t-plot method was 0.18-0.19 cm$^3$/g. It is believed that the first pore filling at $p/p_0 \sim 10^{-4}$-$10^{-3}$ was due to the highly eccentric 10MR channels and the second one at $p/p_0=10-2$ is originated from the 14MR channels. The pore size distribution of CIT-13 according to the cylindrical Saito-Foley (SF) model shown in FIG. 17 well demonstrates these two distinct pore-filling steps. These separated pore-filling steps were not observed in the case of UTL. The physicochemical data related to the channel and pore systems of IM-12 and CIT-13 were summarized in Table 8.

The novel germanosilicate CIT-13 showed a $^{29}$Si NMR spectrum largely similar to that of IM-12, and no silanol group was detected. In the $^{29}$Si MAS NMR spectra, both of the two materials showed multiple peaks significantly overlapping one another in the region from −110 to −120 ppm, indicating that both as-calcined CIT-13 and IM-12 in this work are exclusively composed of Q4 Si and having no silanol group (see FIG. 16(B)). IM-12 apparently showed more peaks than CIT-13 in this Q4 Si-region indicating that the framework UTL has more crystallographically different T-atoms than CIT-13. This is consistent with the fact that the framework UTL has 12 T-atom sites in a unit cell, whereas CIT-13 has only 7. Also, there were shoulder-signals in the downfield region from −105 to −110 ppm that can be assigned as either Si atoms residing in the D4R units 6 or nSi-(4-n)Ge silicon atoms but making unanimous peak assignments was limited in this case.

Example 8. Use of Ammonium Fluoride (NH$_4$F) Instead of HF

CIT-13 was also prepared using NH$_4$F avoiding the use of harmful and dangerous HF. This protocol inspired the fact that NH$_4$F can do the same Brønsted acid-base neutralization reaction, as does HF, in the course of the gel preparation with quaternary amine hydroxides (OSDA+OH−) which are strong bases. A molar equivalent amount of NH$_4$F salt was used replacing HF. Ammonia was isolated and removed by drying the gel thoroughly using an air flow until the appearance of the gel became very powdery. A 160° C. static oven was used to crystallization. CIT-13 from the classic protocol from the reference condition was also synthesized and used as a comparison. For both methods, OSDA 2 was used as the structure-directing agent. These CIT-13 samples from these two methods were studied using XRD, SEM, EDS, TGA and argon adsorption at 87 K. The results were summarized in FIG. 18. The successful drying step of NH$_3$ resulted in the mixture having the same gel composition to the product from the classic HF-protocol, effectively providing the way to avoid the use of concentrated hydrogen fluoride in CIT-13 synthesis.

Consequently, CIT-13 from this NH$_4$F-protocol was essentially identical to CIT-13 from the classic HF-protocol, showing no meaningful difference between the two in physicochemical properties. This indicates that all of ammonia initially present in the system could be successfully evaporated by an extensive drying step, leaving pairs of H+ and F− behind. In powder XRD profiles, (FIG. 18(A)) both samples have shown pure CIT-13 phase with no impurity peak. The SEM images displayed in FIGS. 18(B) and 18(C) also supported the conclusion that the macroscopic morphologies of CIT-13 crystals were not so different to one another; the twinning within each crystallite was also observed in both samples. The Si/Ge ratios of CIT-13/HF and CIT-13/NH$_4$F were 5.03±0.48 and 5.19±0.15, respectively. The TGA studies also revealed that the weight loss data is very similar: 16.5% for CIT-13/HF and 16.1% for CIT-13/NH$_4$F. (FIG. 18(D)). More interestingly, according to the argon adsorption isotherms of the two CIT-13s after calcination shown in FIG. 18(E), CIT-13 from the NH$_4$F-protocol also demonstrated the characteristic two-step adsorption of extra-large-pore CIT-13 having 10MR channels of a high eccentricity shown in FIG. 15. The micropore volumes of CIT-13/NH$_4$F characterized using the t-plot method and the SF-method were 0.191 cm$^3$/g and 0.215 cm$^3$/g.

As those skilled in the art will appreciate, numerous modifications and variations of the present invention are possible in light of these teachings, and all such are contemplated hereby. All references cited herein are incorporated by reference herein, at least for their teachings in the context presented.

What is claimed:

1. A calcined crystalline microporous germanosilicate composition comprising a three-dimensional framework having pores defined by 10- and 14-membered rings and having a ratio of Si:Ge atoms in a range of from 2:1 to 16:1, wherein the calcined crystalline microporous germanosilicate composition exhibits a powder X-ray diffraction (XRD) pattern exhibiting at least five peaks at 6.45±0.2, 7.18±0.2, 12.85±0.2, 20.78±0.2, 26.01±0.2, and 26.68±0.2 degrees 2-θ.

2. A crystalline microporous germanosilicate composition comprising a three-dimensional framework having pores defined by 10- and 14-membered rings and having a ratio of Si:Ge atoms in a range of from 2:1 to 16:1, wherein the composition exhibits at least one of:
 (a) a powder X-ray diffraction (XRD) pattern exhibiting at least seven of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ;
 (b) a powder X-ray diffraction (XRD) pattern the same as shown in FIG. 1(B) or FIG. 1(C); or
 (c) representative unit cell parameters according to:

| Space group | Cmmm |
|---|---|
| a (Å) | 27.4374(5) |
| b (Å) | 13.8000(2) |
| c (Å) | 10.2910(2) |
| V (Å$^3$) | 3896.6(1) |
| Z | 8 |
| ρ (g/cm$^3$) | 2.144(2) |
| λ (Å) | 0.776381(1). |

3. The calcined crystalline microporous germanosilicate composition of claim 1, which exhibits a powder X-ray diffraction (XRD) pattern exhibiting at least seven of the characteristic peaks at 6.45±0.2, 7.18±0.2, 12.85±0.2, 18.26±0.2, 18.36±0.2, 18.63±0.2, 20.78±0.2, 21.55±0.2, 23.36±0.2, 24.55±0.2, 26.01±0.2, and 26.68±0.2 degrees 2-θ.

4. The crystalline microporous germanosilicate composition of claim 2, which exhibits a powder X-ray diffraction (XRD) pattern exhibiting at least five of the characteristic peaks at 6.45±0.2, 7.18±0.2, 12.85±0.2, 20.78±0.2, 26.01±0.2, and 26.68±0.2 degrees 2-θ.

5. The calcined crystalline microporous germanosilicate composition of claim 1 which exhibits representative unit cell parameters according to:

| Space group | Cmmm |
|---|---|
| a (Å) | 27.4374(5) |
| b (Å) | 13.8000(2) |

| Space group | Cmmm |
|---|---|
| c (Å) | 10.2910(2) |
| V (Å$^3$) | 3896.6(1) |
| Z | 8 |
| ρ (g/cm$^3$) | 2.144(2) |
| λ (Å) | 0.776381(1). |

6. The crystalline microporous germanosilicate composition of claim 2, exhibiting at least two of (a), (b), or (c).

7. The calcined crystalline microporous germanosilicate of claim 1, wherein the pore dimensions of the 10- and 14-membered rings are 6.2×4.5 Å and 9.1×7.2 Å, respectively.

8. The crystalline microporous germanosilicate composition of claim 2, comprising germanium and having a ratio of Si:Ge atoms in a range of from 2:1 to 8:1.

9. The crystalline microporous germanosilicate of claim 2, that is free of an organic structure-directing agent (OSDA).

10. The crystalline microporous germanosilicate composition of claim 2, further comprising at least one substituted benzyl-imidazolium organic structure-directing agent (OSDA).

11. The crystalline microporous germanosilicate composition of claim 10, wherein the at least one substituted benzyl-imidazolium organic structure-directing agent has a structure:

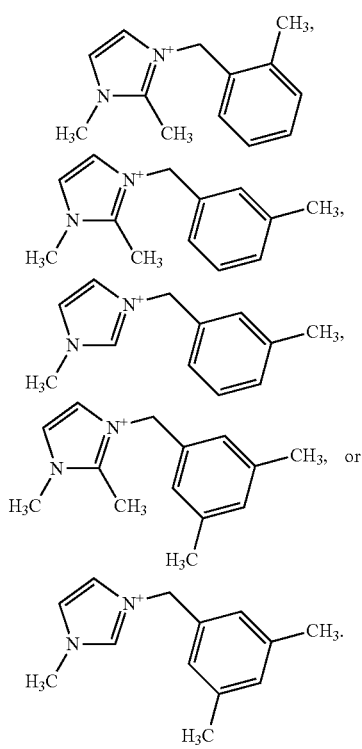

12. A method of preparing the crystalline microporous germanosilicate composition of claim 1 or claim 2, the method comprising hydrothermally treating an aqueous composition comprising:
(a) a source of silicon oxide
(b) a source of germanium oxide;
(c) a mineralizing agent; and
(d) at least one substituted benzyl-imidazolium organic structure-directing agent (OSDA) having a structure:

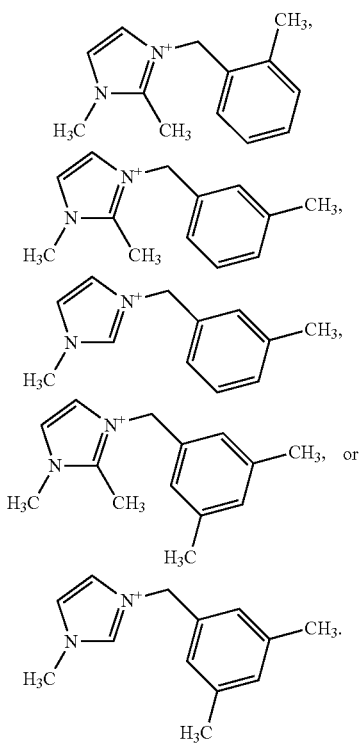

under conditions effective to crystallize a crystalline microporous germanosilicate composition of claim 1.

13. The method of claim 12, wherein:
(a) the source of silicon oxide comprises tetraethyl orthosilicate (TEOS); or
(b) the source of germanium oxide comprises GeO$_2$, or a hydrated derivative thereof or
(c) both (a) and (b).

14. The method of claim 12, wherein the source of silicon oxide and the source of germanium oxide are present in a molar ratio in a range of from about 2:1 to about 8:1.

15. The method of claim 12, wherein the mineralizing agent comprises:
(a) a fluoride source comprising hydrofluoric acid, or a salt or derivative thereof; and/or
(b) a source of hydroxide.

16. The method of claim 12, wherein the mineralizing agent comprises hydrofluoric acid or ammonium fluoride.

17. The method of claim 12, wherein the mineralizing agent comprises an alkali metal hydroxide or alkaline earth metal hydroxide, or combination thereof.

18. The method of claim 12, wherein the crystalline microporous germanosilicate has occluded within its pores at least one of the substituted benzyl-imidazolium organic structure-directing agents.

19. The method of claim 12, wherein the crystalline microporous germanosilicate is free of occluded substituted benzyl-imidazolium organic structure-directing agents.

20. The method of claim 12, wherein the composition is a suspension or a gel.

21. The method of claim 12, wherein effective crystallization conditions include a temperature of from about 140° C. to about 180° C., and a time of from about 4 days to about 4 weeks.

22. The method of claim 12, further comprising isolating a crystalline microporous germanosilicate solid product comprising a three-dimensional framework having pores defined by 10- and 14-membered rings.

23. The method of claim 22, further comprising:
(a) heating the isolated crystalline microporous solid product at a temperature in a range of from about 250° C. to about 450° C.; or
(b) contacting the isolated crystalline microporous solid product with ozone or other oxidizing agent at a temperature in a range of 25° C. to 200° C.;
for a time sufficient to form a dehydrated or an OSDA-depleted product.

24. The method of claim 23, further comprising:
(a) treating the dehydrated or OSDA-depleted product with an aqueous alkali, alkaline earth, transition metal, rare earth metal, ammonium or alkylammonium salt; and/or
(b) treating the dehydrated or OSDA-depleted product with at least one type of transition metal or transition metal oxide.

25. The method of claim 22, further comprising calcining the isolated crystalline microporous solid in air a temperature in a range of from about 500° C. to about 1200° C.

* * * * *

UNITED STATES PATENT AND TRADEMARK OFFICE
CERTIFICATE OF CORRECTION

PATENT NO. : 10,293,330 B2
APPLICATION NO. : 15/169816
DATED : May 21, 2019
INVENTOR(S) : Schmidt et al.

Page 1 of 9

It is certified that error appears in the above-identified patent and that said Letters Patent is hereby corrected as shown below:

On the Title Page

Item [56], References Cited, under heading OTHER PUBLICATIONS, Replace:
1st Column, page 2, Line 35, "Almadhoun et al, "Nanocomposites of Ferroelectric Polymers With Surface-Hydroxylated BaTiO3 Nanoparticles for Energy Storage Applications", Chem., May 2012, 22, 11196."
With:
--Almadhoun et al, "Nanocomposites of Ferroelectric Polymers With Surface-Hydroxylated BaTiO$_3$ Nanoparticles for Energy Storage Applications", Chem., May 2012, 22, 11196-11200.--

1st Column, page 2, Line 40, "Autret et al, "Synthesis and Electrochemistry of Iron (111) Corroles Containing a Nitrosyl Axial Ligand. Spectral Characterization of [(OEC)FeTII(NO)]n Where n=0, 1, 2, or -1 and OEC is the Trianion of 2,3,7,8,12,13,17,18-Octaethylcorrol", J. Am. Chem. Soc., 1994, vol. 116, 9141-9149."
With:
--Autret et al, "Synthesis and Electrochemistry of Iron (III) Corroles Containing a Nitrosyl Axial Ligand. Spectral Characterization of [(OEC)Fe$^{III}$(NO)]$^n$ Where n = 0, 1, 2, or -1 and OEC Is the Trianion of 2,3,7,8,12,13,17,18-Octaethylcorrole", J. Am. Chem. Soc., 1994, vol. 116, 9141-9149.--

1st Column, page 2, Line 53, "Barbe et al, "Metallocorroles As Sensing Components for Gas Sensors: Remarkable Affinity and Selectivity of Cobalt(III) Corroles for CO vs. O2 and N2", The Royal Society of Chemistry, Mar. 23, 2004, 1208-1214."
With:
--Barbe et al, "Metallocorroles As Sensing Components for Gas Sensors: Remarkable Affinity and Selectivity of Cobalt(III) Corroles for CO vs. $O_2$ and $N_2$", The Royal Society of Chemistry, Mar. 23, 2004, 1208-1214.--

1st Column, page 2, Line 57, "Basabe, et al., "Locattion of Extra-Framework Co2, Ni2, Cu2, and Zn2 Cations in Natural and Dealuminated Clinoptilolite", Micro and Meso Materials, 2012, vol. 155, 233-239."

Signed and Sealed this
Eighteenth Day of August, 2020

Andrei Iancu
*Director of the United States Patent and Trademark Office*

CERTIFICATE OF CORRECTION (continued)
U.S. Pat. No. 10,293,330 B2

With:
--Garcia-Basabe et al., "Location of Extra-Framework $Co^{2+}$, $Ni^{2+}$, $Cu^{2+}$, and $Zn^{2+}$ Cations in Natural and Dealuminated Clinoptilolite", Micro and Meso Materials, 2012, vol. 155, 233-239.--

$2^{nd}$ Column, page 2, Line 44, "Hong, et al., "Synthesis Structure Solution, Characterization, and Catalytic Properties of TNU-10: A High-Silica Zeolite with the STI Topology", J. Am. Chem. Soc., 2004, vol. 126, 5817-26."
With:
--Hong, et al., "Synthesis, Structure Solution, Characterization, and Catalytic Properties of TNU-10: A High-Silica Zeolite with the STI Topology", J. Am. Chem. Soc., 2004, vol. 126, 5817-26.--

$2^{nd}$ Column, page 2, Line 57, "Ikeda, et al., "Lateral Distribution of N3 Dye Molecules on TiO2 (110) Surface", Journal of Photochemistry, 2009, vol. 202, 185-190."
With:
--Ikeda, et al., "Lateral Distribution of N3 Dye Molecules on $TiO_2$ (110) Surface", Journal of Photochemistry, 2009, vol. 202, 185-190.--

$2^{nd}$ Column, page 2, Line 66, "Jaracz, et al., "Recent Advances in Tumor-Targeting Anticancer Drug Conjugates" Bioorg. Med. Chem., Dec. 2005, vol. 13(17), 5043-54."
With:
--Jaracz, et al., "Recent Advances in Tumor-Targeting Anticancer Drug Conjugates" Bioorg. Med. Chem., Sep. 2005, vol. 13(17), 5043-54.--

$1^{st}$ Column, page 3, Line 1, "Jin, et al., "Targeted Delivery System of Nanobiomaterials in Anticancer Therapy from Cells to Clinics", BioMed. Res. Inti., Feb. 2014, 24 pages."
With:
--Jin, et al., "Targeted Delivery System of Nanobiomaterials in Anticancer Therapy: From Cells to Clinics", BioMed. Res. Inti., Feb. 2014, 24 pages.--

$1^{st}$ Column, page 3, Line 4, "Kanamoril et al, "Neuroprotection Against Superoxide Anion Radical by Metallocorroles in Cellular and Murine Models of Optic Neuropathy", Journal ofNeurochemistry, 2010, vol. 114, 488-498."
With:
--Kanamori et al, "Neuroprotection Against Superoxide Anion Radical by Metallocorroles in Cellular and Murine Models of Optic Neuropathy", Journal ofNeurochemistry, 2010, vol. 114, 488-498.--

$1^{st}$ Column, page 3, Line 20, "Li, et al., "Metal Exchanged Ferrierites as Catalysts for the Selective Reduction of NO with Methane", Appl. Catal. B Environ., 1993, vol. 3, L1-L11."
With:
--Li, et al., "Metal Exchanged Ferrierites as Catalysts for the Selective Reduction of $NO_x$ with Methane", Appl. Catal. B: Environ., 1993, vol. 3, L1-L11 .--

$1^{st}$ Column, page 3, Line 32, "Mahammed et al, "Highly Selective Chlorosulfonation of Tris(Pentafluorophenyl) Corrole as a Synthetic Tool for the Preparation of Amphiphilic Corroles and Metal Complexes of Planar Chirality", Organic Letters, Nov. 1, 2001, vol. 3(22), 3443-3436."

CERTIFICATE OF CORRECTION (continued)
U.S. Pat. No. 10,293,330 B2

With:
--Mahammed et al, "Highly Selective Chlorosulfonation of Tris(Pentafluorophenyl) Corrole as a Synthetic Tool for the Preparation of Amphiphilic Corroles and Metal Complexes of Planar Chirality", Organic Letters, Nov. 1, 2001, vol. 3(22), 3443-3446.--

1st Column, page 3, Line 61, "Moliner et al., "Towards thje rational design of efficient organic structure-directing agents for zeolite synthesis", Agnew Chem International Edition, 2013, 52, 13880-13889."
With:
--Moliner et al., "Towards the rational design of efficient organic structure-directing agents for zeolite synthesis", Agnew Chem International Edition, 2013, 52, 13880-13889.--

2nd Column, page 3, Line 39, "Schmidt, et al., "Facile Preparation of Aluminosilicate RTH Across a Wide Composition Rabge Using a New Organic Structure-Directing Agent", Chem. of Materials, Nov. 18, 2014, 7 pgs."
With:
--Schmidt, et al., "Facile Preparation of Aluminosilicate RTH Across a Wide Composition Range Using a New Organic Structure-Directing Agent", Chem. of Materials, December 05, 2014, 7 pgs.--

2nd Column, page 3, Line 42, "Schreyeck, et al., "PREFER: A New Layered (Alumino) Silicate Precursor of FER-Type Zeolite", Microporous Matter, 1996, vol. 6,259-71."
With:
--Schreyeck, et al., "PREFER: A New Layered (Alumino) Silicate Precursor of FER-Type Zeolite", Microporous Materials, 1996, vol. 6, 259-71.--

1st Column, page 4, Line 25, "Wan, et al., "Three-Dimensional Rotation Electron Diffraction: Software RED for Automated Data Collection and Date Processing" J. Appl. Cryst., Dec. 2013, vol. 46, 1863-1873."
With:
--Wan, et al., "Three-Dimensional Rotation Electron Diffraction: Software RED for Automated Data Collection and Data Processing" J. Appl. Cryst., Dec. 2013, vol. 46, 1863-1873.--

1st Column, page 4, Line 34, "Wang, et al., "Synthesis and Crystal Structure of Zeolite RUB-41 Obtained as Calcination Product of a Layers Precursor: A Systematic Approach to a New Synthesis Route", Chem. Matter, 2005, vol. 17, 43-49."
With:
--Wang, et al., "Synthesis and Crystal Structure of Zeolite RUB-41 Obtained as Calcination Product of a Layered Precursor: A Systematic Approach to a New Synthesis Route", Chem. Mater., 2005, vol. 17, 43-49.--

In the Drawings

At the bottom of drawings Sheet 1 of 22, insert FIG. 1(C) as shown on the attached sheet

CERTIFICATE OF CORRECTION (continued)
U.S. Pat. No. 10,293,330 B2

In the Claims

Under Column 47, Claim no. 11, Lines 32-60, Replace:

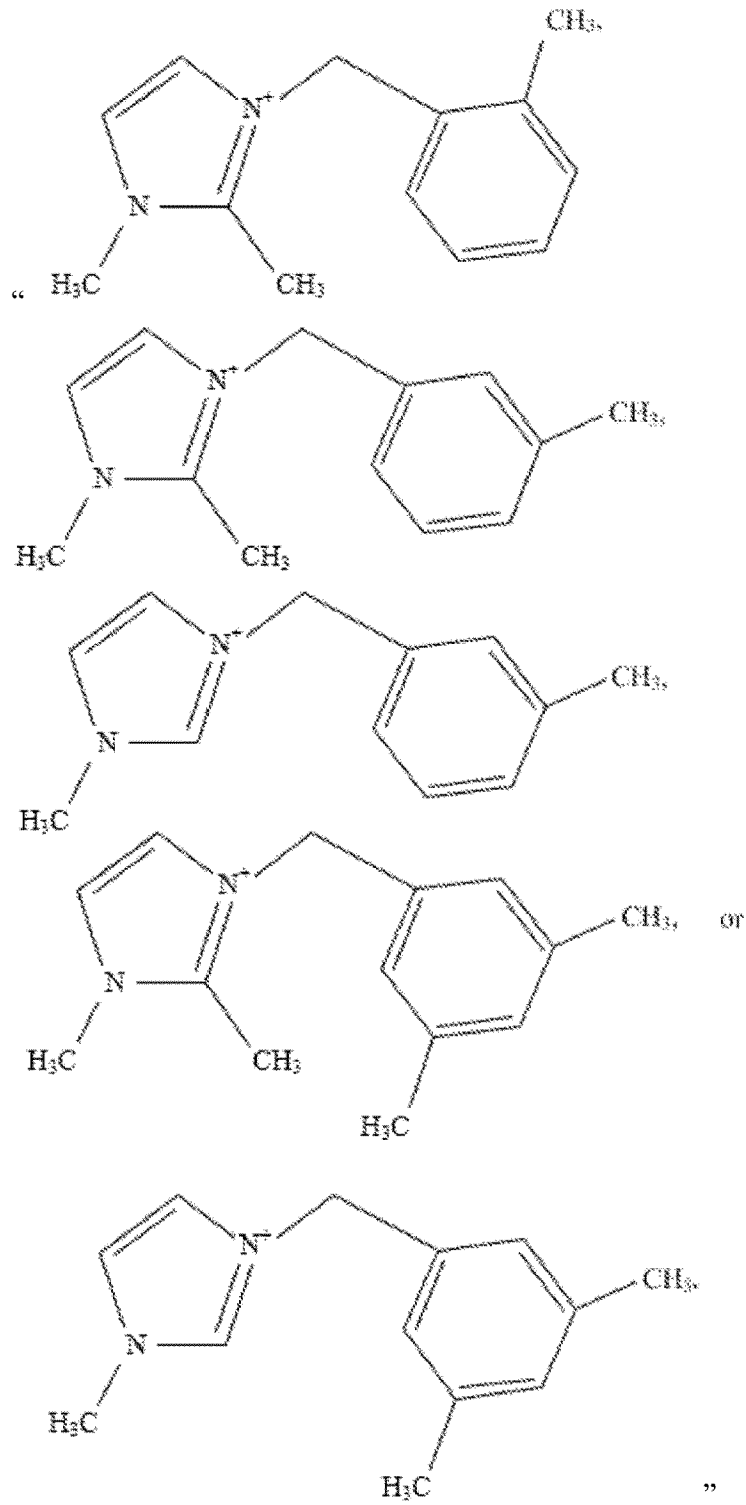

With:
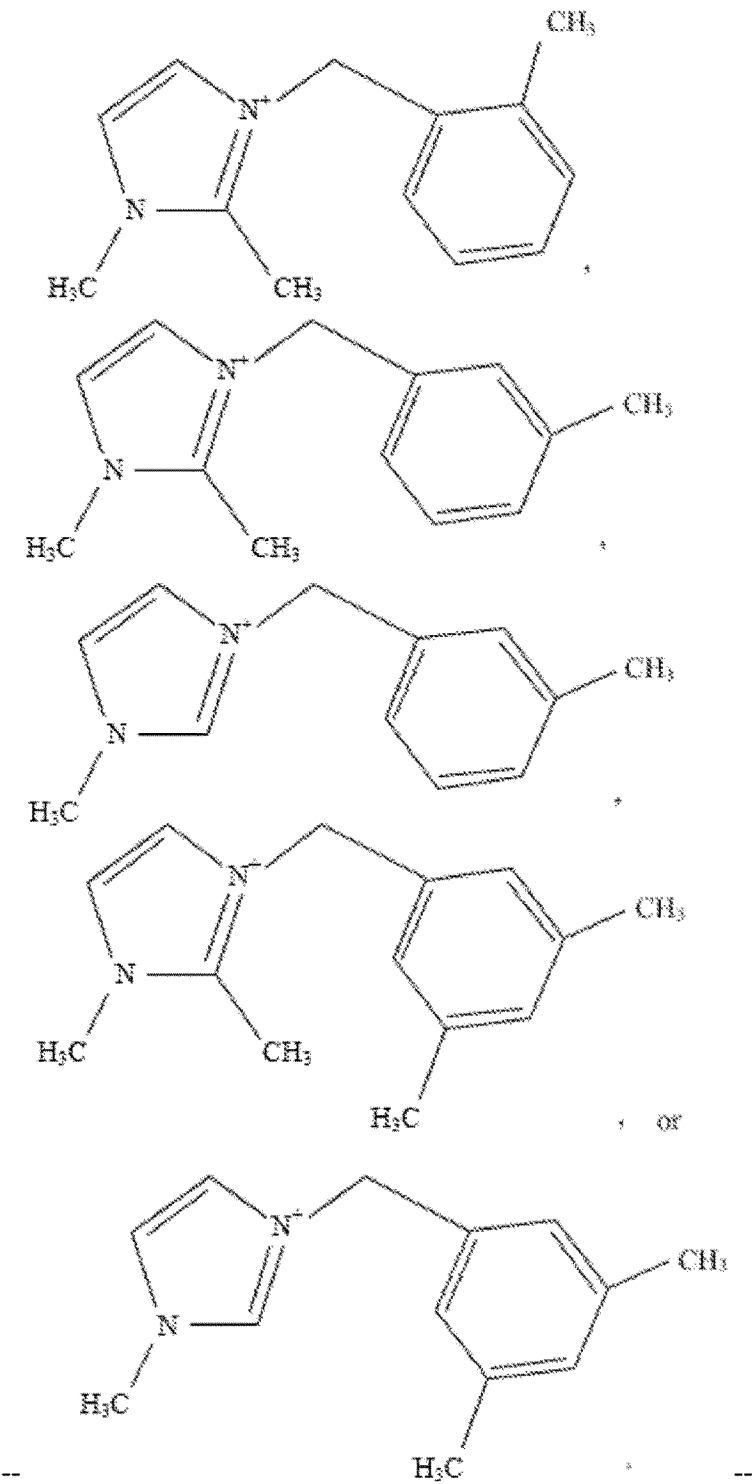
Under Column 47, Claim no. 12, Line 65, Replace:
"(a) a source of silicon oxide"
With:
--(a) a source of silicon oxide;--

Under Column 48, Claim no. 12, Lines 5-32, Replace:
" 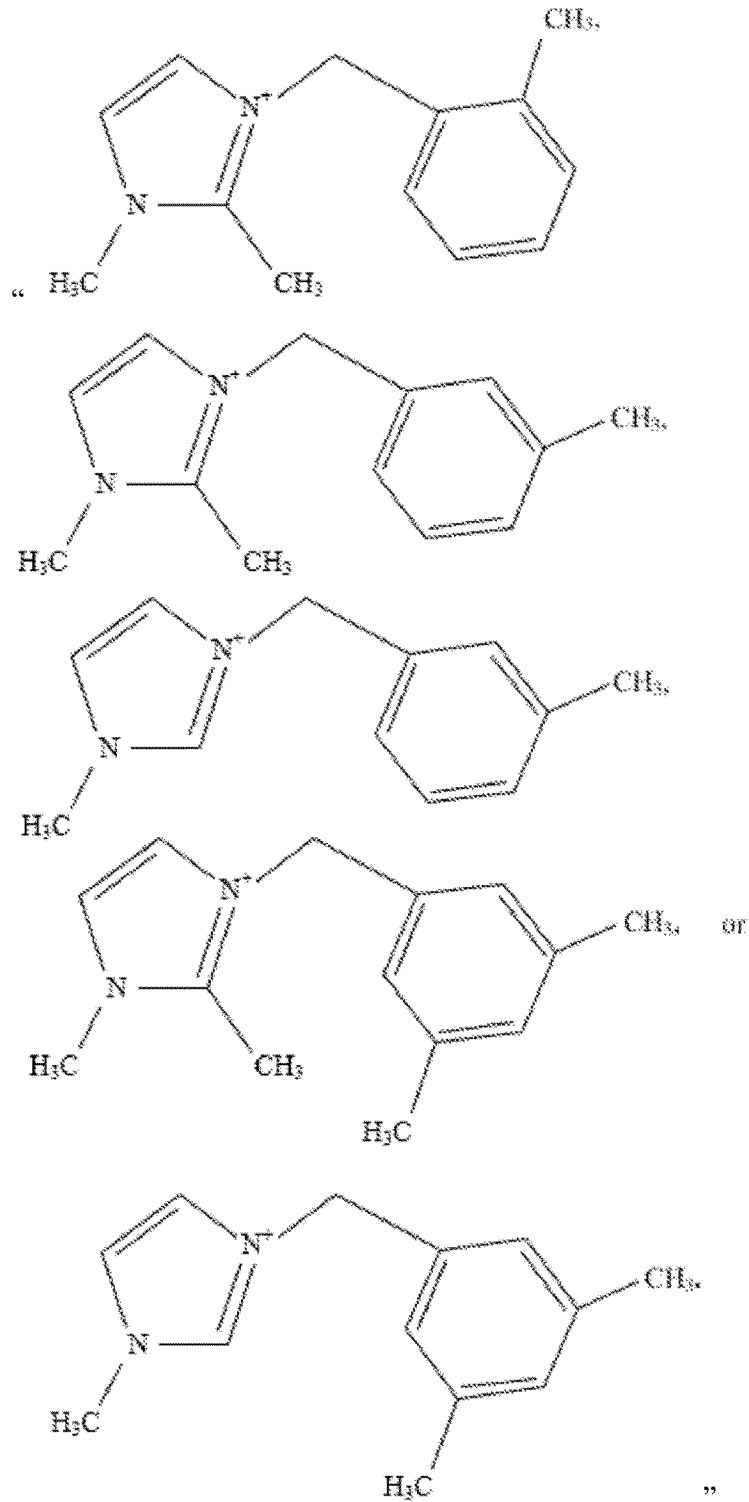  "
With:

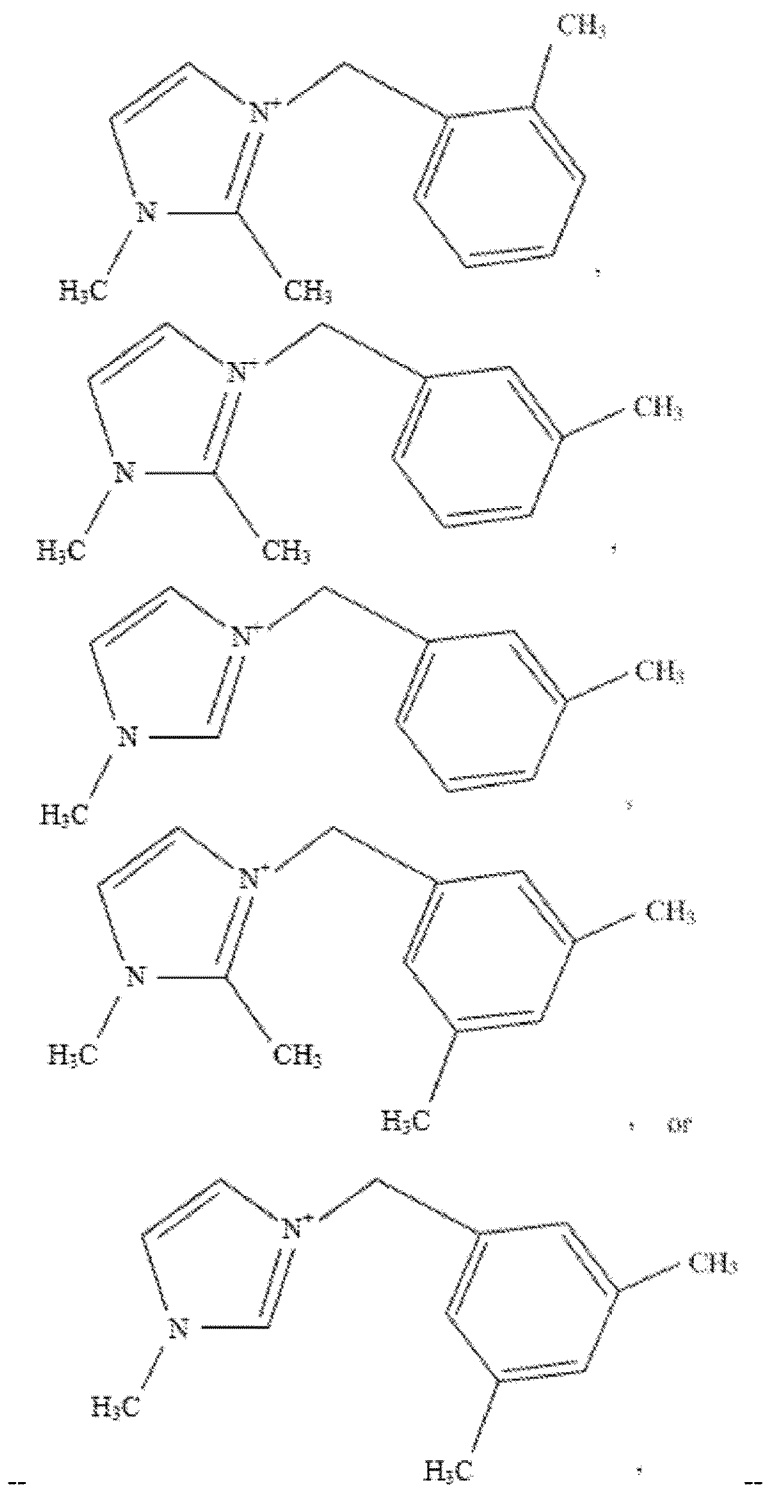
Under Column 48, Claim no. 12, Sub point (d) at Lines 26-31, in the last Figure of organic structure-directing agent, Replace:

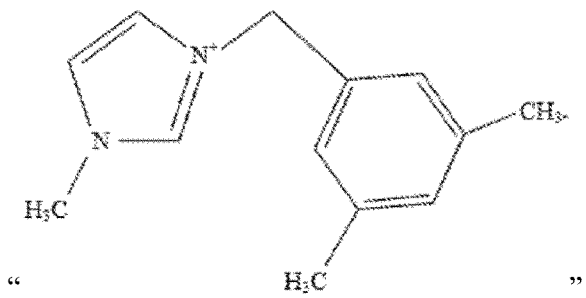
"
With:
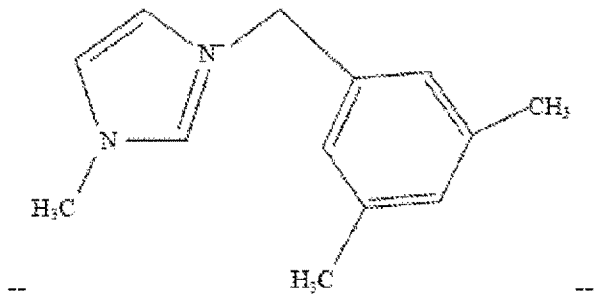
--
Under Column 48, Claim no. 13, Line 40, Replace:
"hydrated derivative thereof or"
With:
--hydrated derivative thereof; or--